(12) United States Patent
Flynn

(10) Patent No.: US 11,900,464 B1
(45) Date of Patent: *Feb. 13, 2024

(54) COMPUTER SOFTWARE, PROCESSES, ALGORITHMS AND INTELLIGENCE THAT FORECAST A SETTLEMENT PRICE AND NEGATIVE ACTIONS TAKEN BY PROVIDERS AGAINST PATIENTS, WITH DEBTS OWED, BASED ON SPECIFIC VARIABLES

(71) Applicant: Kevin Flynn, Philadelphia, PA (US)

(72) Inventor: Kevin Flynn, Philadelphia, PA (US)

( * ) Notice: Subject to any disclaimer, the term of this patent is extended or adjusted under 35 U.S.C. 154(b) by 329 days.

This patent is subject to a terminal disclaimer.

(21) Appl. No.: 16/194,810

(22) Filed: Nov. 19, 2018

Related U.S. Application Data

(60) Division of application No. 14/832,372, filed on Aug. 21, 2015, now abandoned, which is a continuation-in-part of application No. 14/257,499, filed on Apr. 21, 2014, now abandoned, and a continuation-in-part of application No. 14/257,493, filed on Apr. 21, 2014, now abandoned, which is a continuation-in-part of application No. 13/528,764, filed on Jun. 20, 2012, now Pat. No. 8,706,616, said
(Continued)

(51) Int. Cl.
*G06Q 20/42* (2012.01)
*G06Q 20/00* (2012.01)
*G06Q 40/08* (2012.01)

(52) U.S. Cl.
CPC .......... *G06Q 40/08* (2013.01); *G06Q 20/42* (2013.01)

(58) Field of Classification Search
None
See application file for complete search history.

(56) References Cited

U.S. PATENT DOCUMENTS

| 5,446,653 A | 8/1995 | Miller et al. |
| 7,774,214 B1 | 8/2010 | Lefco et al. |

(Continued)

OTHER PUBLICATIONS

"U.S. Appl. No. 13/528,764, 312 Amendment filed Feb. 18, 2014", 6 pgs.
(Continued)

*Primary Examiner* — David P Sharvin
(74) *Attorney, Agent, or Firm* — Culhane Meadows PLLC; Michael P. Dunnam

(57) ABSTRACT

An automated method for resolving a debtor's debt obligation to a creditor uses a rating algorithm that implements predictive analytics to determine an anticipated amount for which the creditor will settle the debt. A debt purchase amount to be offered to the Debtor to have a third-party entity fully assume the Debtor's debt obligation is calculated based on the anticipated amount for which the creditor will settle the debt and operating costs and profit margin of the third-party entity. An offer to the Debtor to have the third-party entity fully assume the Debtor's debt obligation for the debt purchase amount is generated and sent with a document indicating that the Debtor has agreed to transfer the Debtor's debt obligation to the third-party entity pursuant to the offer. The creditor is notified that the third-party entity has assumed responsibility for the Debtor's debt obligation and resolved the Debtor's debt obligation.

21 Claims, 81 Drawing Sheets

Related U.S. Application Data application No. 14/257,499 is a continuation-in-part of application No. 13/528,764, filed on Jun. 20, 2012, now Pat. No. 8,706,616.

(60) Provisional application No. 62/150,031, filed on Apr. 20, 2015, provisional application No. 62/043,621, filed on Aug. 29, 2014, provisional application No. 61/498,835, filed on Jun. 20, 2011.

(56) References Cited

U.S. PATENT DOCUMENTS

| | | | |
|---|---|---|---|
| 8,706,616 B1 | 4/2014 | Flynn | |
| 2002/0123946 A1* | 9/2002 | Haworth | G06Q 40/00 705/35 |
| 2003/0050795 A1 | 3/2003 | Baldwin, Jr. et al. | |
| 2004/0249666 A1 | 12/2004 | Napolitano et al. | |
| 2005/0010438 A1 | 1/2005 | York et al. | |
| 2006/0190300 A1 | 8/2006 | Drucker | |
| 2006/0190334 A1 | 8/2006 | Smith | |
| 2007/0208594 A1 | 9/2007 | Yang et al. | |
| 2009/0043697 A1* | 2/2009 | Jacobs | G06Q 20/10 705/39 |
| 2010/0076864 A1* | 3/2010 | Reynolds | G06Q 20/14 705/26.1 |
| 2010/0287093 A1 | 11/2010 | He et al. | |
| 2010/0324924 A1 | 12/2010 | Frederiksen | |
| 2011/0010189 A1 | 1/2011 | Dean et al. | |
| 2011/0035315 A1* | 2/2011 | Langley | G06Q 40/00 705/38 |
| 2011/0071860 A1 | 3/2011 | Fontenot | |

OTHER PUBLICATIONS

"U.S. Appl. No. 13/528,764, 312 Amendment filed Feb. 28, 2014", 4 pgs.

"U.S. Appl. No. 13/528,764, 312 Amendment filed Dec. 9, 2013", 11 pgs.

"U.S. Appl. No. 13/528,764, Non Final Office Action dated Jun. 6, 2013", 8 pgs.

"U.S. Appl. No. 13/528,764, Notice of Allowance dated Dec. 2, 2013", 12 pgs.

"U.S. Appl. No. 13/528,764, Preliminary Amendment filed Aug. 1, 2012", 5 pgs.

"U.S. Appl. No. 13/528,764, PTO Response to 312 Amendment dated Feb. 5, 2014", 2 pgs.

"U.S. Appl. No. 13/528,764, PTO Response to 312 Amendment dated Mar. 21, 2014", 2 pqs.

"U.S. Appl. No. 13/528,764, Response filed Sep. 6, 2013 to Non Final Office Action dated Jun. 6, 2013", 12 pgs.

"U.S. Appl. No. 14/832,372, Non Final Office Action dated Feb. 9, 2018", 16 pgs.

"U.S. Appl. No. 14/832,372, Notice of Non-Compliant Amendment dated Sep. 21, 2018", 5 pgs.

"U.S. Appl. No. 14/832,372, Response filed Jun. 8, 2018 to Non Final Office Action dated Feb. 9, 2018", 22 pgs.

"U.S. Appl. No. 14/832,372, Restriction Requirement dated Sep. 21, 2018", 5 pgs.

"ARxChange", TriCap Technology Group, [Online] Retrieved from the internet: <http://arxchange.com/>, (Nov. 14, 2013), 3 pgs.

Grow, Brian, et al., "Fresh Pain for the Uninsured", Businessweek Magazine, [Online] Retrieved from the internet: <http://www.businessweek.com/stories/2007-12-02/fresh-pain-for-the-uninsured>, (Dec. 3, 2007), 10 pgs.

Microvu, "Itemized Claim Review", [Online] Retrieved from the internet: <http://www.mvsavings.com/services/itemized-claim-review.htm>, (Nov. 14, 2013), 2 pgs.

\* cited by examiner

FIG. 1A-1

STEP 1 of 7

I. Your Contact Information

Full Name: [ ]
Address: [ ]
City, State Zip: [ ]
Tel#: [ ]
Email: [ ]

II. Please input the requested information on the bill below:

Provider Name: [ ] [ ] [ ] [ ]
　　　　　　　　　　　　Provider Address　City, State, Zip　Tax ID Patient Name: [ ]

Date of Service: [ ]

Total Amount Billed by Provider: $[ ]

Total Amount Currently Owed: $[ ] -------- 120

How much of the total amount owed is for a Deductible: $[ ]

How much of the total amount owed is for a Co-Insurance: $[ ]

If the provider already gave a discount, how much was given: $[ ] ------ 121

II. Upload Scanned Images of the Medical Bills:

Click here to locate the imaged/scanned file on your computer to upload: [Browse - File To Upload]

[Submit] [Reset]

FIG. 1A-2

STEP 2 of 7

Please answer the following questions relating to the bill:

A. Prior Financial Agreements: Please check one of boxes below:

● No, the Responsible Party has not entered into any financial agreements for the accounts described in Section II of this agreement.

○ Yes, the Responsible Party has entered into any financial agreements for the accounts described in Section II of this agreement. Please attach the agreement(s) or if it was an oral agreement(s), describe the agreement(s):

[                                                                              ]

B. Prior Efforts To Satisfy The Bill(s): Please check one of boxes below:

○ No entity (lawyer, proxy, other) representing the Responsible Party has contacted the provider to try and resolve the bill(s) described in II..

○ Yes, the Responsible Party had an entity (lawyer, proxy, other) try to resolve the bill(s) described in Section II of this Agreement. Please describe the efforts:

[                                                                              ]

[Submit] [Reset]

FIG. 1A-3

STEP 3 of 7

C. Workers Compensation: Please check one of boxes below:

○ No, none of the bill(s) listed in Section II are related to Workers Compensation insurance or a Workers Compensation claim.

○ Yes, one or more of the bill(s) listed in Section II are related to Workers Compensation insurance or a Workers Compensation claim. Please list which bill(s) are part of a Workers Compensation claim:

[ ]

D. Auto Accident: Please check one of boxes below:

○ No, none of the bill(s) listed in Section II are related to an automobile accident.

○ Yes, one or more of the bill(s) listed in Section II are related to an automobile accident. Please list which bill(s) are related to an automobile accident:

[ ]

[Submit]  [Reset]

FIG. 1A-4

STEP 4 of 7

E. Was the provider In-Network: Please check one of boxes below:

○ No.

○ Yes.

F. Did you have health insurance at the time the debt was incurred: Please check one of boxes below:

○ No.

○ Yes.

G. Was this an elective procedure: Please check one of boxes below:

○ No.

○ Yes.

H. Did a medical error occur at any time: Please check one of boxes below:

○ No.

○ Yes.

I. Was the provider a facility or a medical office: Please check one of boxes below:

○ Office, Clinic

○ Hospital

[Submit] [Reset]

FIG. 1A-5

STEP 5 of 7

J. Was the provider located in an urban area: Please check one of boxes below:

○ No.

○ Yes.

K. If you had health insurance, was the bill denied by the insurance company?

○ No.

○ Yes.

L. If you answered "yes" to the insurer denying the claim; did you complete the appeals process?

○ No.

○ Yes.

M. What is your approximate credit score?

Input credit score here: [　　　　　　]

[Submit]  [Reset]

FIG. 1A-6

STEP 6 of 7

N. Provider Type (click one)?

○ Medical

○ Dental

○ Durable medical equipment

○ Alternative medicine

○ Pharmacy

O. Are you currently in bankruptcy proceedings?

○ No.

○ Yes.

P. Is the patient deceased?

○ No.

○ Yes.

[Submit] [Reset]

FIG. 1A-7

STEP 7 of 7

III. Please answer the following questions relating to your financial status:

A. Lawsuit: Please check one of boxes below: ---------- 124

○ No, I am not seeking indemnification and a defense in the event a lawsuit is initiated against me relating to the bills listed in Section II above.

○ Yes, I am seeking indemnification and a defense in the event a lawsuit is initiated against me relating to the bills listed in Section II above.

B. Credit Repair: Please check one of boxes below: --------- 126

○ No, I am not seeking to repair my credit rating relating to the bills listed in Section II above.

○ Yes, I am seeking to repair my credit rating relating to the bills listed in Section II above.

C. Income: Please fill-out:

Annual Income: [_____] ------ 170

Number of people that live at your residence: [_____] ------- 172

Value of total assets (i.e. money in bank, property owned, cars): [_____] ---- 174

[Submit]  [Cancel]

FIG. 1B-1

STEP 1 of 7

I. Your Contact Information

- Full Name: _____
- Address: _____
- City, State Zip: _____
- Tel#: _____
- Email: _____

II. Please input the requested information on the bill below:

Provider Name: _____  _____  _____  _____
    Provider Address    City, State, Zip    Tax ID Patient Name: _____

Date of Service: _____

Total Amount Billed by Provider: $_____

Total Amount Currently Owed: $_____ -------- 120

How much of the total amount owed is for a Deductible: $_____

How much of the total amount owed is for a Co-Insurance: $_____

If the provider already gave a discount, how much was given: $_____ -------- 121

II. Upload Scanned Images of the Medical Bills:

Click here to locate the imaged/scanned file on your computer to upload: [Browse - File To Upload]

[Submit]   [Reset]

FIG. 1B-2

STEP 2 of 6

Please answer the following questions relating to the bill:

A. Prior Financial Agreements: Please check one of boxes below:

⦿ No, the Responsible Party has not entered into any financial agreements for the accounts described in Section II of this agreement.

○ Yes, the Responsible Party has entered into any financial agreements for the accounts described in Section II of this agreement. Please attach the agreement(s) or if it was an oral agreement(s), describe the agreement(s):

[                                                                        ]

B. Prior Efforts To Satisfy The Bill(s): Please check one of boxes below:

○ No entity (lawyer, proxy, other) representing the Responsible Party has contacted the provider to try and resolve the bill(s) described in II..

○ Yes, the Responsible Party had an entity (lawyer, proxy, other) try to resolve the bill(s) described in Section II of this Agreement. Please describe the efforts:

[                                                                        ]

[Submit]  [Reset]

FIG. 1B-3

STEP 3 of 7

C. Workers Compensation: Please check one of boxes below:

○ No, none of the bill(s) listed in Section II are related to Workers Compensation insurance or a Workers Compensation claim.

○ Yes, one or more of the bill(s) listed in Section II are related to Workers Compensation insurance or a Workers Compensation claim. Please list which bill(s) are part of a Workers Compensation claim:

[                                                                    ]

D. Auto Accident: Please check one of boxes below:

○ No, none of the bill(s) listed in Section II are related to an automobile accident.

○ Yes, one or more of the bill(s) listed in Section II are related to an automobile accident. Please list which bill(s) are related to an automobile accident:

[                                                                    ]

[Submit] [Reset]

FIG. 1B-4

STEP 4 of 7

E. Was the provider In-Network: Please check one of boxes below:

○ No.

○ Yes.

F. Did you have health insurance at the time the debt was incurred: Please check one of boxes below:

○ No.

○ Yes.   Estimated insurance payment: [_____] ------ 122

G. Was this an elective procedure: Please check one of boxes below:

○ No.

○ Yes.

H. Did a medical error occur at any time: Please check one of boxes below:

○ No.

○ Yes.

I. Was the provider a facility or a medical office: Please check one of boxes below:

○ Office, Clinic

○ Hospital

[Submit]   [Reset]

FIG. 1B-5

STEP 5 of 7

J. Was the provider located in an urban area: Please check one of boxes below:

○ No.

○ Yes.

K. If you had health insurance, was the bill denied by the insurance company?

○ No.

○ Yes.

L. If you answered "yes" to the insurer denying the claim; did you complete the appeals process?

○ No.

○ Yes.

M. What is your approximate credit score?

Input credit score here: [          ]

[Submit] [Reset]

FIG. 1B-6

STEP 6 of 7

N. Provider Type (click one)?

○ Medical

○ Dental

○ Durable medical equipment

○ Alternative medicine

○ Pharmacy

O. Are you currently in bankruptcy proceedings?

○ No.

○ Yes.

P. Is the patient deceased?

○ No.

○ Yes.

[Submit] [Reset]

FIG. 1B-7

STEP 7 of 7

III. Please answer the following questions relating to your financial status:

A. Lawsuit: Please check one of boxes below: ------- 124

○ No, I am not seeking indemnification and a defense in the event a lawsuit is initiated against me relating to the bills _____ listed in Section II above.

○ Yes, I am seeking indemnification and a defense in the event a lawsuit is initiated against me relating to the bills _____ listed in Section II above.

B. Credit Repair: Please check one of boxes below: ---- 126

○ No, I am not seeking to repair my credit rating relating to the bills listed in Section II above.

○ Yes, I am seeking to repair my credit rating relating to the bills listed in Section II above.

C. Income: Please fill-out:

Annual Income: [_____] ------- 180

Number of people that live at your residence: [_____] ---- 182

Value of total assets (i.e. money in bank, property owned, cars): [_____] --- 184

[Submit] [Cancel]

FIG. 3-1

Date: [Variable: date field]

[Variable: Party's Name]
[Variable: Address]
[Variable: City, State Zip code]

Re: Agreement - Transfer of Medical Debt Liability to PODS entity

Dear [Variable: Party's Name]:

Please accept agreement between [name] of [city/state] (herein referred to as "Seller") and PODS a Delaware Corporation (herein referred to as "PODS"). The basis of this Agreement is that PODS will assume by novation, and Seller transfers to PODS by novation, the debt and responsibilities for the accounts listed in Section I of this Agreement. Intending to be legally bound by this Agreement and based on the following mutually agreed upon terms:

Section I - Cost and Transfer of Debt Liability:

120
|
Seller agrees to pay PODS the sum of $[variable: Selling Price] for the medical bills outlined in the table below. In consideration of payment, Seller hereby transfers by novation the financial responsibility and all duties and obligations for these accounts with the respective creditor(s) as outlined below. PODS agrees to assume all liabilities and perform all duties and obligations of [patient name] for the care rendered. The effective date is the date this Agreement is signed.

[Variable: the table below is from the data inputted from FIG. 1A-1 thru 1A-7 or FIG. 1B-1 thru 1B-7]

| Provider Name | Patient Name | Date of Service | Total Owed | Provider Acct# |
|---|---|---|---|---|
| [variable field] | [variable field] | [variable field] | [variable field] | [variable field] |

Section II Definitions: Capitalized terms used in this Agreement shall have the meanings as ascribed to them herein.

- A "Seller" is the person who is responsible for the medical bill(s) and is the insurance beneficiary (i.e. the patient, legal guardian).
- The "Patient" is the person who received care or their legal guardian.
- The "Agreement" refers to this letter of understanding.
- The 'purchase of the debt,' 'sell your medical bill,' 'buy my medical bill' or 'purchase of your medical bill' as advertised, is in the form of a discounted payment/responsibility by Seller for the debt listed in Section I.
- An "EOB" is an insurance company's or payer's explanation of benefits.
- Workers Compensation refers to a workers' compensation insurance plan(s).

Section III – Escrow Account: Seller's payment will be deposited into an escrow account.

Section IV – Provider Billing: i) Though the debt liability has been assigned, it is likely that Patient will continue to receive bills until the account is settled. Provider software is designed in

FIG. 3-2 a specific way and it is unlikely that the provider will manually override the system to have any outstanding invoices sent to PODS. When Patient receives an invoice simply mail or fax it to PODS. ii) If a provider is mailed payment late in the month, it is doubtful that billing department will receive the check and post it to the account by the time the provider completes its next billing cycle. Based on this, there will be times when payment is made and an invoice is still sent (i.e. crossing in the mail). iii) Provider software and procedures do not lend to a receipt. Instead of a "paid in full letter" providers simply stop billing the patient. To compensate for provider practices, PODS will send notice to Seller via email that the case is settled.

Section V - Forty-Five Day Review: It is mutually agreed that PODS has forty-five days from the day the bill(s), financial agreements with provider/creditor, medical records, full health plan description and EOBs are received by PODS to review the accuracy of the information supplied by Seller and to terminate this Agreement at PODS' discretion.

Section VI – Monetary Loss: PODS may lose or gain money in this transaction depending on the settlement with the provider. It is mutually agreed that any monetary loss or gain will be PODS'.

Section VII – HIPAA Revocation: To assist in protecting the Seller and/or Patient, it is mutually agreed that if requested, Seller will have the Patient execute a HIPAA revocation form and submit same to HCA to allow HCA to submit same to the provider of services.

Section VIII – Confidentiality: With the exception of Seller's attorney or a court ordered subpoena, it is mutually agreed that this Agreement is confidential and will not be shared with or distributed to any other person or entity. Further, reasonable care shall be used to ensure others do not read or copy it.

Section IX – Transfer, Discharge and Obligations:
    A. Patient is released and discharged from further obligations, liabilities and payments with respect to each the debts owed as indicated in Section I. All remaining liabilities and obligations shall be paid and preformed by PODS in accordance with the patient-provider contract entered into for the services rendered in Section I.

124

B. If the creditor disputes the transfer of this Agreement, and PODS deems the creditor's dispute valid, then this Agreement will default to a personal guarantee of payment of the debt whereby PODS is liable for the debt and PODS will supply a legal defense for Seller if the provider/creditor initiates a lawsuit or negative mark on your credit report.

Section X - Responsibilities of Seller: In addition to its obligations under this Agreement and any other agreements between the parties, Seller is responsible for:

A. When a creditor or an agent (i.e. Collection company or law firm working on behalf of the provider) contacts Seller about the outstanding balance, Seller agrees to respond simply as follows, "please contact PODS as they are financially responsible for the bill."
    B. Within seven (7) days of the execution of this Agreement, Seller will forward the latest insurance statements (a.k.a. explanation of benefits) that relate to the bills listed in Section I.

FIG. 3-3

C. Seller will comply with all requests for information and additional materials by PODS. All questions and requests will be completed by Seller as quickly as possible. As a standard, it is reasonable to have questions answered within seven (7) days and requests for materials delivered within fourteen (14) days.

D. Seller agrees to forward copies of all bills, collection notices, legal notices and other to PODS within five (5) days of receipt by Seller until the bill(s) accepted by PODS (listed in Section I) are settled.

E. There is a possibility that the bills accepted by PODS in Section I have or will be sent to a collections company or law firm. While PODS has assumed liability for the bills, PODS cannot guarantee that the bill(s) have not or will not be sent to a collections company, law firm, reported to a collection company; or other actions taken by the provider. PODS will provide a 'notice of liability' to the Seller so that the Seller may provide the 'notice of liability' to the collection company, credit reporting company, law firm or provider. Though PODS is liable for the bill(s) that it accepted, PODS cannot guarantee that the provider, collection company or law firm will cease contacting Patient as PODS cannot control, and is not responsible for, the actions of the collections companies, credit reporting companies, law firm, provider or other third parties. Further, PODS is not a credit repair company and Seller must repair his/her own credit history.

F. Seller agrees to provide PODS with HIPAA consent forms, signed by Patient, when necessary thereby allowing PODS to obtain documents (i.e. medical records, invoices, etc) from the provider, insurer and/or third party that PODS determines necessary to satisfy the provider's claim/bill.

G. It is mutually agreed that Seller hereby assigns and transfers any and all unpaid or outstanding insurance benefits for the bill(s) described in Section I to PODS and that any money paid by an insurance company or third party for the debt will be endorsed over to PODS and mailed to PODS. Seller further agrees to if Seller or Patient does not forward said payment to PODS, that Seller will pay all legal expenses associated with PODS collecting said payment.

H. If legal action is commenced in relation to the medical bills(s) listed in Section I, Seller agrees to make reasonable efforts to assist PODS as needed during the lawsuit including but not limited to, providing documents, answering questions, participating in depositions and other things deemed necessary to support PODS' position during the legal action.

I. Seller agrees it is Patient's responsibility to notify the insurer of any adjustments to the account if notice to the insurer is required.

Section XI - Representations and Warranties of Seller:

A. The execution and delivery of this Agreement, and the performance by Seller of its obligations hereunder, have been duly authorized by all necessary parties on the part of Seller.

B. This Agreement has been duly executed and delivered by Seller and is a legal, valid and binding obligation of Seller, enforceable against Seller in accordance with its terms.

C. Seller verifies that the bills being presented are accurate and that there are no additional charges, fees or other outstanding debts in connection with the bills listed in Section I of this Agreement.

D. All documents and work product are the property of PODS and considered confidential as they contain confidential/trade secret information.

FIG. 3-4

E. Seller certifies that, to date, there has been no threat of legal action in an effort to collect on the outstanding bills described in Section I.

F. PODS may share billing data with the sales agent or third party broker for the purpose of reconciling any commissions or other financial issues. Private medical data will not be shared.

G. Insurance companies and other payers occasionally retract payment when they discover a payment was made in error. Seller agrees that any retracted payment(s) are not the responsibility of PODS and PODS is not liable for any loss or damages as a result of the retracted payment(s).

H. Seller certifies that neither the Patient nor Seller has signed any agreements with the provider or creditor regarding the bills outlined in Section I.

I. Seller certifies that the provider has not been contacted with regard with reducing, negotiating or lowering the amount due.

J. Seller certifies that the provider has not provided any discounts on the monies owed.

K. Seller certifies that Patient/guarantor has not signed a document with a non-transfer clause.

Section XII -  Indemnification:

A. Seller Indemnification Obligations: Seller shall indemnify and defend PODS, its representatives, officers, directors, employees, agents, successors and assignees (the "Seller INDEMNIFIED PARTIES") and hold the Seller INDEMNIFIED PARTIES harmless from and against any and all damages, based upon, attributable to, arising out of, or resulting from: (i)The breach by Seller of any provision of this Agreement. (ii) Promises, mis-representations and incorrect statements made by any third party, including sales agents or brokers, regarding PODS and this Agreement. (iii) Though PODS has assumed the liability of the bills described in Section I of this Agreement, there is a chance that the bills may still be sent to a collection company or be placed as a black mark on the Seller's credit history in error. In such situations, Seller will not hold PODS responsible for the actions of the creditor(s) and Seller is responsible for contacting the credit agency to have the adverse credit mark removed from the Seller's credit report.

B. PODS Indemnification Obligations: PODS shall indemnify Seller (the "PODS INDEMNIFIED PARTIES") and hold the PODS INDEMNIFIED PARTIES harmless from and against any and all damages, including, without limitation, based upon, attributable to, arising out of, or resulting from the breach of any covenant or other agreement on the part of PODS under this Agreement.

(i) Promises, mis-representations and incorrect statements made by PODS to the Seller.

130

(ii) If legal action by the provider is initiated for non-payment of the bill(s) accepted by PODS (in Section I) against Patient, PODS agrees to indemnity, defend and hold harmless ("assume the defense") Patient in the legal action. This clause is void if the legal action involves fraud, misrepresentation(s), a retracted payment by a payer, a breach of an agreement between the plaintiff and Seller, or other action that is not for the excusive reason of payment of the medical bill.

FIG. 3-5

Section XIII – Termination & Cancellation: i) Should Seller breach any of the terms contained herein or make a material misrepresentation, PODS is entitled to return the medical bill(s) and Seller's money, minus any out-of-pocket costs paid by PODS, and terminate this Agreement. ii) Should PODS breach any of the terms contained herein Seller must give PODS thirty (30) days written notice to cure and fix the breach. If the breach is not cured within 60 days, Seller may terminate this Agreement. iii) Seller has three (3) days, beginning the date this Agreement is signed, to cancel this Agreement.

Section XIV - Interpretation: The Parties hereto acknowledge and agree that (i) the rule of construction providing that any ambiguities are resolved against the drafting Party will not apply in interpreting the terms and provisions of this Agreement; and (ii) the terms and provisions of this Agreement will be construed fairly as to all Parties hereto and not in favor of or against a Party, regardless of which Party was generally responsible for the preparation of this Agreement.

Section XV - Entire Agreement: This Agreement constitutes the entire Agreement between the parties hereto with respect to the subject matter hereof and supersedes all prior agreements, either written or oral, of the parties hereto concerning the subject matter hereof.

Section XVI - Venue & Governing Law: This Agreement shall be governed by, interpreted and construed in accordance with the laws of the state of Delaware. Venue is Wilmington, DE.

Section XVII - Dispute and Arbitration: In the event the parties should have a dispute between them arising from or related to this Agreement, and which dispute cannot be resolved by mutual agreement of the parties, the parties hereby agree that Seller must file for arbitration in Wilmington, Delaware. Any such arbitration shall be determined by a panel of three arbitrators taking sworn testimony, in accordance with the Commercial Rules of the American Arbitration Association. The arbitrator shall be determined in the following manner: Within thirty (30) days from the filing for arbitration, both parties shall submit a list of three arbitrator candidates to the other party. The parties shall select from the submitted lists one candidate to be the sole arbitrator.

If within sixty (60) days from the filing for arbitration the parties can not agree on the arbitrators, then the arbitration shall be decided by a panel of three arbitrators, whereby each party shall immediately select one arbitrator and those two arbitrators shall then select a third arbitrator. The parties hereof hereby agree to accept and to abide by the arbitrator(s)' judgment of determination or award, which determination or award may be entered in any court having jurisdiction.

For purposes of this Section XVII, filing for arbitration shall be deemed to mean the delivery of notice by the filing party to the other party of the filing party's decision to seek resolution of a dispute by the means of arbitration.

FIG. 3-6

Arbitration is solely on an individual basis without the right for any claim(s) to be arbitrated on a class action basis or claim(s) brought in a representative capacity on behalf of others. The arbitrator's authority to resolve and make written awards is limited to claims between Seller and PODS alone. Claims may not be joined or consolidated unless agreed to in writing by all parties. No arbitration award or decision will have any preclusive effect as to issues or claims in any dispute with anyone who is not a named party to the arbitration. Notwithstanding any other provision in these terms and conditions, and without waiving either party's right of appeal, if any portion of this Section XVII is deemed invalid or unenforceable, then the arbitration provision shall not apply.

Section XVIII - Waiver and Amendment: No waiver or amendment of this Agreement shall be effective unless it is in writing and is signed by a duly authorized person of each respective party. The failure of either party to enforce any provision of this Agreement shall not constitute a waiver by either party of any provision. The past waiver of a provision by either party shall not constitute a course of conduct or pre-suppose a waiver in the future of that same provision.

Intending to be bound by the terms and conditions herein; I hereby consent to this debt transfer affirming that no modification of the patient-provider contract is made or intended, except that HCA is now and hereafter substituted for Patient.

By Clicking "I Accept Agreement" You Are Agreeing to this Agreement:

Enter You Name In this box as an electronic Signature [    ]

| I Accept Agreement | I Decline Agreement |

PRIMARY GUARANTOR AGREEMENT

Date: [Variable: date field]

[Variable: Party's Name]
[Variable: Address]
[Variable: City, State Zip code]

Re: Letter of Understanding

Dear [Variable: Party's Name]:

Please accept this as a letter of understanding between you (herein referred to as "Seller") and [Name of Entity], Inc (herein referred to as "HCA"). The basis of this understanding is that HCA will guarantee the debt liability listed in Section 1 of this letter of understanding based on the following mutually agreed upon terms:

1. Cost and Guarantor Status          120

Seller agrees to pay HCA the sum of $[variable: Selling Price] to become the primary guarantor for the medical bills outlined in the table below; the effective date is the date this Agreement is signed. In consideration for payment, HCA agrees to be the primary guarantor for the accounts listed below and is responsible for settling the account(s) in full with the creditor.

[Variable: the table below is from the data inputted from FIG. 1A-1 thru 1A-7 or FIG. 1B-1 thru 1B-7]

| Provider Name (city/state) | Patient Name | Date of Service | Total Owed | Provider Acct# |
|---|---|---|---|---|
| [variable field] | [variable field] | [variable field] | [variable field] | [variable field] |

2. Definitions: Capitalized terms used in this Agreement shall have the meanings as ascribed to them herein.

- A "Seller" is the person who is responsible for the medical bill(s) and is the insurance beneficiary (i.e. the patient, child's guardian).
- The "Agreement" refers to this letter of understanding.
- The "purchase of the debt" or "purchase of your medical bill" as advertised, is in the form of a discounted payment/responsibility by Seller for the debt listed in Section 1.
- An "EOB" is an insurance company's or payer's explanation of benefits.
- Workers Compensation refers to a workers' compensation insurance plan(s).

FIG 4-2

3. Forty-Five Day Review: It is mutually agreed that HCA has forty-five days from the day the bill(s), financial agreements, medical records, full health plan description and EOBs are received by HCA to review the accuracy of the information supplied by Seller and to terminate this Agreement at HCA's discretion.

4. Monetary Loss: HCA may lose or gain money in this transaction depending on the settlement with the provider. It is mutually agreed that any monetary loss or gain will be HCA's.

5. Transfer, Discharge and Obligations:
    A. Patient is released and discharged from further obligations, liabilities and payments with respect to each the debts owed as indicated in Section 1. All remaining liabilities and obligations shall be paid and preformed by HCA in accordance with the patient-provider contract entered into for the services rendered in Section 1.

B. If the creditor disputes the transfer of this Agreement, and HCA deems the creditor's dispute valid, then this Agreement will default to a personal guarantee of payment of the debt and a legal defense between HCA and Patient.

6. Responsibilities of Seller: In addition to its obligations under this Agreement and any other agreements between the parties, Seller is responsible for:

A. When a creditor or an agent (i.e. Collection company or law firm working on behalf of the provider) contacts Seller about the outstanding balance, Seller agrees to respond simply as follows, "please contact [Name of Entity], Inc as they are financially responsible for the bill."

B. Within seven (7) days of the execution of this agreement, Seller will forward the latest insurance statements (a.k.a. explanation of benefits) that relate to the bills listed in Section 1.

C. Seller will comply with all requests for information and additional materials by HCA. All questions and requests will be completed by Seller as quickly as possible. As a standard, it is reasonable to have questions answered within seven (7) days and requests for materials delivered within fourteen (14) days.

D. Seller agrees to forward copies of all bills, collection notices, legal notices and other to HCA within five (5) days of receipt by Seller until the bill(s) accepted by HCA (listed in Section 1) are settled.

E. There is a possibility that the bills accepted by HCA in Section 1 have or will be sent to a collections company or law firm. While HCA is the guarantor for the bills, HCA cannot guarantee that the bill(s) have not or will not be sent to a collections company, law firm, reported to a collection company; or other actions taken by the

FIG. 4-3 provider. Further, HCA cannot guarantee that the provider, collection company or law firm will leave you alone as HCA cannot control, and is not responsible for, the actions of the collections companies, credit reporting companies, law firm, provider or other third parties. Further, HCA is not a credit repair company and Seller must repair his/her own credit history.

F. Seller agrees to provide HCA with HIPAA consent forms when necessary thereby allowing HCA to obtain documents (i.e. medical records, invoices, etc) from the provider, insurer and/or third party that HCA determines necessary to satisfy the provider's claim/bill.

G. It is mutually agreed that Seller hereby assigns and transfers any and all insurance benefits for the bill(s) described in Section 1 to HCA and that any money paid by an insurance company or third party for the debt will be endorsed over to HCA and mailed to HCA. Seller further agrees to pay all legal expenses associated with collecting said funds if Seller fails to send payment from the insurer or third party.

H. If litigation is commenced in relation to the medical bills(s) listed in Section 1, Seller agrees to make reasonable efforts to assist HCA as needed during the lawsuit including but not limited to, providing documents, answering questions, participating in depositions and other things deemed necessary to support HCA's position during the litigation.

I. Seller will notify his/her insurance company of the total amount they paid for the medical care in the event the amount of the medical debt is applied to Seller's deductible or other.

7. Representations and Warranties of Seller:

A. The execution and delivery of this Agreement, and the performance by Seller of its obligations hereunder, have been duly authorized by all necessary parties on the part of Seller.

B. This Agreement has been duly executed and delivered by

Seller and is a legal, valid and binding obligation of Seller, enforceable against Seller in accordance with its terms.

C. Seller verifies that the bills being presented are accurate and that there are no additional charges, fees or other outstanding debts in connection with the bills listed in Section 1 of this Agreement.

D. All documents and work product are the property of HCA and considered confidential as they contain confidential/trade secret information.

FIG 4-4

E. The bills described in Section 1 of this Agreement are either not in collections or have been in collections for less than 60 days. Further, Seller certifies that there has been no threat of any legal action in an effort to collect on the outstanding bills described in Section 1.

F. HCA may share account data with the sales agent or third party broker for the purpose of reconciling any commissions or other financial issues. Private medical data will not be shared.

G. Insurance companies and other payers occasionally retract payment when they discover a payment was made in error. Seller agrees that any retracted payment(s) are not the responsibility of HCA and HCA is not liable for any loss or damages as a result of the retracted payment(s).

8. Indemnification:

A. Seller Indemnification Obligations:

Seller shall indemnify and defend HCA, its representatives, officers, directors, employees, agents, successors and assignees (the "Seller INDEMNIFIED PARTIES") and hold the Seller INDEMNIFIED PARTIES harmless from and against any and all damages, based upon, attributable to, arising out of, or resulting from:

(i) The breach by Seller of any provision of this Agreement.

(ii) Promises, mis-representations and incorrect statements made by any third party, including sales agents or brokers, regarding HCA and this Agreement.

(iii) Though HCA is the guarantor of the bills described in Section 1 of this Agreement, there is a chance that the bills may still be sent to a collection company or be placed as a black mark on the Seller's credit history in error. In such situations, Seller will not hold HCA responsible for the actions of the creditor(s) and Seller is responsible for contacting the credit agency to have the adverse credit mark removed from the Seller's credit report.

B. HCA Indemnification Obligations:

HCA shall indemnify Seller (the "HCA INDEMNIFIED PARTIES") and hold the HCA INDEMNIFIED PARTIES harmless from and against any and all damages, including, without limitation, based upon, attributable to, arising out of, or resulting from the breach of any covenant or other agreement on the part of HCA under this Agreement.

FIG 4-5

(i) Promises, mis-representations and incorrect statements made by HCA to the Seller.

130

(ii) If legal action by the provider is initiated for non-payment of the bill(s) accepted by HCA (in Section 1) against Seller, HCA agrees to indemnity, defend and hold harmless ("assume the defense") Seller in the legal action. This clause is void if the legal action involves fraud, misrepresentation(s), a retracted payment by a payer, a breach of an agreement between the plaintiff and Seller, or other action that is not for the excusive reason of payment of the medical bill.

9.      Confidential Information:

A. It is mutually agreed that this Agreement is confidential and will not be disclosed unless pursuant to a court order.

B. During the term of this Agreement, and at all times thereafter, each of the parties hereto agree: (i) not to, directly or indirectly, disclose, utilize or permit the unauthorized use or disclosure of any proprietary and/or confidential information, oral or written, with regard to its respective business, operations, methodologies, clients or other confidential information (collectively called the "CONFIDENTIAL INFORMATION"); and (ii) that each originating party's respective CONFIDENTIAL INFORMATION shall remain the sole property of such originating party. Notwithstanding the foregoing, this restriction shall not apply to information which an originating party releases to the general public or to third parties without restriction, or to information which is disclosed pursuant to judicial order or regulatory proceeding or to information that is published or becomes public knowledge through sources other than the parties listed in this Agreement. The confidentiality obligations of the parties hereof shall survive any termination of this Agreement. Further, it is agreed that all work product is confidential and property of HCA.

10.      Termination: Should Seller breach any of the terms contained herein or make a material misrepresentation, HCA is entitled to return the medical bill(s) and Seller's money and terminate this Agreement.

11.      Interpretation: The Parties hereto acknowledge and agree that (i) the rule of construction providing that any ambiguities are resolved against the drafting Party will not apply in interpreting the terms and provisions of this Agreement; and (ii) the terms and provisions of this Agreement will be construed fairly as to all Parties hereto and not in favor of or against a Party, regardless of which Party was generally responsible for the preparation of this Agreement.

12.      Entire Agreement: This Agreement constitutes the entire Agreement between the parties hereto with respect to the subject matter hereof and supersedes all prior agreements, either written or oral, of the parties hereto concerning the subject matter hereof.

FIG 4-6

13. Venue & Governing Law: This Agreement shall be governed by, interpreted and construed in accordance with the laws of the Commonwealth of Pennsylvania. Venue is Philadelphia, PA.

14. Dispute and Arbitration: In the event the parties should have a dispute between them arising from or related to this Agreement, and which dispute cannot be resolved by mutual agreement of the parties, the parties hereby agree that Seller must file for arbitration in Philadelphia, PA. Any such arbitration shall be determined by one arbitrator taking sworn testimony, in accordance with the Commercial Rules of the American Arbitration Association.

The arbitrator shall be determined in the following manner: Within thirty (30) days from the filing for arbitration, both parties shall submit a list of three arbitrator candidates to the other party. The parties shall select from the submitted lists one candidate to be the sole arbitrator. If within sixty (60) days from the filing for arbitration the parties can not agree on one arbitrator, then the arbitration shall be decided by a panel of three arbitrators, whereby each party shall immediately select one arbitrator and those two arbitrators shall then select a third arbitrator. The parties hereof hereby agree to accept and to abide by the arbitrator(s)' judgment of determination or award, which determination or award may be entered in any court having jurisdiction.

For purposes of this Section 14, filing for arbitration shall be deemed to mean the delivery of notice by the filing party to the other party of the filing party's decision to seek resolution of a dispute by the means of arbitration.

15. Waiver and Amendment: No waiver or amendment of this Agreement shall be effective unless it is in writing and is signed by a duly authorized person of each respective party. The failure of either party to enforce any provision of this Agreement shall not constitute a waiver by either party of any provision. The past waiver of a provision by either party shall not constitute a course of conduct or pre-suppose a waiver in the future of that same provision.

Clicking "I Accept Agreement" You Are Agreeing to this Agreement:

Enter You Name In this box as an electronic Signature [    ]

| I Accept Agreement | I Decline Agreement |

FIG. 5-1

STEP-IN AGREEMENT

Date: [Variable: date field]

[Variable: Party's Name]
[Variable: Address]
[Variable: City, State Zip code]

Re: Letter of Understanding

Dear [Variable: Party's Name]:

Please accept this Agreement between you (herein referred to as "Seller") and [Name of Entity], Inc (herein referred to as "HCA"). The basis of this understanding is that HCA will "Step-in" and assume the debt liability(s) listed in Section 1 of this letter of understanding based on the following mutually agreed upon terms:

1. Cost and Step-in Status            120

Seller agrees to pay HCA the sum of $[variable: Selling Price]. In consideration for payment, HCA agrees to be the guarantor and incur, assume and accept the financial responsibility and liability, for the medical bills outlined in the table below and is responsible for settling the account(s) in-full with the creditor. The effective date is the date this Agreement is signed.

[Variable: the table below is from the data inputted from FIG. 1A-1 thru 1A-7 or FIG. 1B-1 thru 1B-7]

| Provider Name (city/state) | Patient Name | Date of Service | Total Owed | Provider Acct# |
|---|---|---|---|---|
| [variable field] | [variable field] | [variable field] | [variable field] | [variable field] |

2. Definitions: Capitalized terms used in this Agreement shall have the meanings as ascribed to them herein.

- A "Seller" is the person who is responsible for the medical bill(s) and is the insurance beneficiary (i.e. the patient, child's guardian).
- The "Agreement" refers to this letter of understanding.
- The 'purchase of the debt' or 'purchase of your medical bill' as advertised, is in the form of a discounted payment/responsibility by Seller for the debt listed in Section 1.
- An "EOB" is an insurance company's or payer's explanation of benefits.
- Workers Compensation refers to a workers' compensation insurance plan(s).

FIG. 5-2

3. Forty-Five Day Review: It is mutually agreed that HCA has forty-five days from the day the bill(s), financial agreements, medical records, full health plan description and EOBs are received by HCA to review the accuracy of the information supplied by Seller and to terminate this Agreement at HCA's discretion.

4. Monetary Loss: HCA may lose or gain money in this transaction depending on the settlement with the provider. It is mutually agreed that any monetary loss or gain will be HCA's.

5. Transfer, Discharge and Obligations: Patient is released and discharged from further obligations, liabilities and payments with respect to each the debts owed as indicated in Section 1. All remaining liabilities and obligations shall be paid and preformed by HCA in accordance with the patient-provider contract entered into for the services rendered in Section 1.

6.     Responsibilities of Seller: In addition to its obligations under this Agreement and any other agreements between the parties, Seller is responsible for:

A.     When a creditor or an agent (i.e. Collection company or law firm working on behalf of the provider) contacts Seller about the outstanding balance, Seller agrees to respond simply as follows, "please contact [Name of Entity], Inc as they are financially responsible for the bill."

B.     Within seven (7) days of the execution of this agreement, Seller will forward the latest insurance statements (a.k.a. explanation of benefits) that relate to the bills listed in Section 1.

C. Seller will comply with all requests for information and additional materials by HCA. All questions and requests will be completed by Seller as quickly as possible. As a standard, it is reasonable to have questions answered within seven (7) days and requests for materials delivered within fourteen (14) days.

D. Seller agrees to forward copies of all bills, collection notices, legal notices and other to HCA within five (5) days of receipt by Seller until the bill(s) accepted by HCA (listed in Section 1) are settled.

E. There is a possibility that the bills accepted by HCA in Section 1 have or will be sent to a collections company or law firm. While HCA has accepted responsibility for the bills, HCA cannot guarantee that the bill(s) have not or will not be sent to a collections company, law firm, reported to a collection company; or other actions taken by the provider. Further, HCA cannot guarantee that the provider, collection company or law firm will leave you alone as HCA cannot

FIG 5-3 control, and is not responsible for, the actions of the collections companies, credit reporting companies, law firm, provider or other third parties. Further, HCA is not a credit repair company and Seller must repair his/her own credit history.

F. Seller agrees to provide HCA with HIPAA consent forms when necessary thereby allowing HCA to obtain documents (i.e. medical records, invoices, etc) from the provider, insurer and/or third party that HCA determines necessary to satisfy the provider's claim/bill.

G. It is mutually agreed that Seller hereby assigns and transfers any and all insurance benefits for the bill(s) described in Section 1 to HCA and that any money paid by an insurance company or third party for the debt will be endorsed over to HCA and mailed to HCA. Seller further agrees to pay all legal expenses associated with collecting said funds if Seller fails to send payment from the insurer or third party.

H. If litigation is commenced in relation to the medical bills(s) listed in Section 1, Seller agrees to make reasonable efforts to assist HCA as needed during the lawsuit including but not limited to, providing documents, answering questions, participating in depositions and other things deemed necessary to support HCA's position during the litigation.

I. Seller will notify his/her insurance company of the total amount they paid for the medical care in the event the amount of the medical debt is applied to Seller's deductible or other.

7. Representations and Warranties of Seller:

A. The execution and delivery of this Agreement, and the performance by Seller of its obligations hereunder, have been duly authorized by all necessary parties on the part of Seller.

B. This Agreement has been duly executed and delivered by

Seller and is a legal, valid and binding obligation of Seller, enforceable against Seller in accordance with its terms.

C. Seller verifies that the bills being presented are accurate and that there are no additional charges, fees or other outstanding debts in connection with the bills listed in Section 1 of this Agreement.

D. All documents and work product are the property of HCA and considered confidential as they contain confidential/trade secret information.

E. The bills described in Section 1 of this Agreement are either not in collections or have been in collections for less than 60 days. Further, Seller certifies that there has been no threat of any legal action in an effort to collect on the outstanding bills described in Section 1.

FIG 5-4

F. HCA may share account data with the sales agent or third party broker for the purpose of reconciling any commissions or other financial issues. Private medical data will not be shared.

G. Insurance companies and other payers occasionally retract payment when they discover a payment was made in error. Seller agrees that any retracted payment(s) are not the responsibility of HCA and HCA is not liable for any loss or damages as a result of the retracted payment(s).

8. Indemnification:

A. Seller Indemnification Obligations:

Seller shall indemnify and defend HCA, its representatives, officers, directors, employees, agents, successors and assignees (the "Seller INDEMNIFIED PARTIES") and hold the Seller INDEMNIFIED PARTIES harmless from and against any and all damages, based upon, attributable to, arising out of, or resulting from:

(i) The breach by Seller of any provision of this Agreement.

(ii) Promises, mis-representations and incorrect statements made by any third party, including sales agents or brokers, regarding HCA and this Agreement.

(iii) Though HCA has accepted the liability(s) for the bills described in Section 1 of this Agreement, there is a chance that the bills may still be sent to a collection company or be placed as a black mark on the Seller's credit history in error. In such situations, Seller will not hold HCA responsible for the actions of the creditor(s) and Seller is responsible for contacting the credit agency to have the adverse credit mark removed from the Seller's credit report.

B. HCA Indemnification Obligations:

HCA shall indemnify Seller (the "HCA INDEMNIFIED PARTIES") and hold the HCA INDEMNIFIED PARTIES harmless from and against any and all damages, including, without limitation, based upon, attributable to, arising out of, or resulting from the breach of any covenant or other agreement on the part of HCA under this Agreement.

(i) Promises, mis-representations and incorrect statements made by HCA to the Seller.

(ii) If legal action by the provider is initiated for non-payment of the bill(s) accepted by HCA (in Section 1) against Seller, HCA agrees to indemnity, defend and hold harmless ("assume the defense") Seller in the legal action. This clause is void if the legal action involves fraud, misrepresentation(s), a retracted payment by a payer, a breach of an agreement between the plaintiff and Seller, or other action that is not for the excusive reason of payment of the medical bill.

9. Confidential Information:

A. It is mutually agreed that this Agreement is confidential and will not be disclosed unless pursuant to a court order.

B. During the term of this Agreement, and at all times thereafter, each of the parties hereto agree: (i) not to, directly or indirectly, disclose, utilize or permit the unauthorized use or disclosure of any proprietary and/or confidential information, oral or written, with regard to its respective business, operations, methodologies, clients or other confidential information (collectively called the "CONFIDENTIAL INFORMATION"); and (ii) that each originating party's respective CONFIDENTIAL INFORMATION shall remain the sole property of such originating party. Notwithstanding the foregoing, this restriction shall not apply to information which an originating party releases to the general public or to third parties without restriction, or to information which is disclosed pursuant to judicial order or regulatory proceeding or to information that is published or becomes public knowledge through sources other than the parties listed in this Agreement. The confidentiality obligations of the parties hereof shall survive any termination of this Agreement. Further, it is agreed that all work product is confidential and property of HCA.

10. Termination: Should Seller breach any of the terms contained herein or make a material misrepresentation, HCA is entitled to return the medical bill(s) and Seller's money and terminate this Agreement.

11. Interpretation: The Parties hereto acknowledge and agree that (i) the rule of construction providing that any ambiguities are resolved against the drafting Party will not apply in interpreting the terms and provisions of this Agreement; and (ii) the terms and provisions of this Agreement will be construed fairly as to all Parties hereto and not in favor of or against a Party, regardless of which Party was generally responsible for the preparation of this Agreement.

12. Entire Agreement: This Agreement constitutes the entire Agreement between the parties hereto with respect to the subject matter hereof and supersedes all prior agreements, either written or oral, of the parties hereto concerning the subject matter hereof.

13. Venue & Governing Law: This Agreement shall be governed by, interpreted and construed in accordance with the laws of the Commonwealth of Pennsylvania. Venue is Philadelphia, PA.

FIG 5-6

14.  Dispute and Arbitration: In the event the parties should have a dispute between them arising from or related to this Agreement, and which dispute cannot be resolved by mutual agreement of the parties, the parties hereby agree that Seller must file for arbitration in Philadelphia, PA. Any such arbitration shall be determined by one arbitrator taking sworn testimony, in accordance with the Commercial Rules of the American Arbitration Association. The arbitrator shall be determined in the following manner: Within thirty (30) days from the filing for arbitration, both parties shall submit a list of three arbitrator candidates to the other party. The parties shall select from the submitted lists one candidate to be the sole arbitrator. If within sixty (60) days from the filing for arbitration the parties can not agree on one arbitrator, then the arbitration shall be decided by a panel of three arbitrators, whereby each party shall immediately select one arbitrator and those two arbitrators shall then select a third arbitrator. The parties hereof hereby agree to accept and to abide by the arbitrator(s)' judgment of determination or award, which determination or award may be entered in any court having jurisdiction.

For purposes of this Section 14, filing for arbitration shall be deemed to mean the delivery of notice by the filing party to the other party of the filing party's decision to seek resolution of a dispute by the means of arbitration.

15.  Waiver and Amendment: No waiver or amendment of this Agreement shall be effective unless it is in writing and is signed by a duly authorized person of each respective party. The failure of either party to enforce any provision of this Agreement shall not constitute a waiver by either party of any provision. The past waiver of a provision by either party shall not constitute a course of conduct or pre-suppose a waiver in the future of that same provision.

Clicking "I Accept Agreement" You Are Agreeing to this Agreement:

Enter You Name In this box as an electronic Signature [    ]

[ I Accept Agreement ]   [ I Decline Agreement ]

FIG. 6A

Date: [Variable: date field]

[Variable: Provider's/Creditor's/Credit Bureau's Name]
[Variable: Address]
[Variable: City, State Zip code]

Re: Transfer of Patient Debt Liability to ABC Company

Dear [Variable: Provider's/Creditor's/Credit Bureau's Name]:

This letter confirms that ABC Company has exected a novation agreement with [Variable: Patient's Name], and is responsible, for the outstanding debt for the claim(s) listed below. If there are any questions, please contact us directly.

ABC Company is responsible for the debts indicated below:

| Provider Name (city/state) | Patient Name | Date of Service | Total Owed | Provider Acct# |
|---|---|---|---|---|
| [variable field] | [variable field] | [variable field] | [variable field] | [variable field] |

Sincerely,

ABC Company

FIG. 6B

Date: [Variable: date field]

[Variable: Provider's Name)]
[Variable: Address]
[Variable: City, State Zip code]

Re: Transfer of Patient Debt Liability to ABC Company

Dear [Variable: Provider's Name]:

This letter confirms that ABC Company has exected a novation agreement with [Variable: Patient's Name]. The agreement between [variable: patient name] and [Variable: Provider's Name] is hereby cancelled and discharged. ABC Company agrees to be responsible for all liabilities, payments and duites that that had been [variable: patient name]'s for the claim(s) listed below. ABC Company is responsible for payment of the debts indicated below:

| Provider Name (city/state) | Patient Name | Date of Service | Total Owed | Provider Acct# |
|---|---|---|---|---|
| [variable field] | [variable field] | [variable field] | [variable field] | [variable field] |

Unless [Variable: Provider's Name] provides written notice providing the reason you object to this novation, then this new agreement between ABC Company and [Variable: Provider's Name] within ten (10) days, the novation will be deemed to be accepted by [Variable: Provider's Name]. ABC Company reserves the right to deem the novation vaild even if you provide a reason for objecting to the novation. Enclosed is a check in the amount of [Variable: $ amount] indicating good faith.

Sincerely,

ABC Company

FIG. 6C

Date: [Variable: date field]

[Variable: Provider's Name]
[Variable: Address]
[Variable: City, State Zip code]

Re: Transfer of Patient Debt Liability to ABC Company

Dear [Variable: Party's Name]:

This letter confirms that ABC Company has exected a novation agreement with [Variable: patient's name]. The agreement between [variable: patient name] and [Variable: Provider's Name] is hereby cancelled and discharged. ABC Company agrees to be responsible for all liabilities, payments and duites that that had been [variable: patient's name] for the claim(s) listed below. ABC Company is responsible for payment of the debts indicated below:

| Provider Name (city/state) | Patient Name | Date of Service | Total Owed | Provider Acct# |
|---|---|---|---|---|
| [variable field] | [variable field] | [variable field] | [variable field] | [variable field] |

Please have an authroized reperesentative of [Variable: provider/creditor name] sign and date this document below acknowledging the novation, and this new agreement between ABC Company and [Variable: Provider's Name] and return it to ABC Company via US mail, facsimilie or email.

By: _____    Date:_____
   (authroized representative of provider/creditor)

Sincerely,

ABC Company

FIG. 6D

Date: [Variable: date field]

[Variable: Provider's Name]
[Variable: Address]
[Variable: City, State Zip code]

Re: Transfer of Debt to ABC Company

Dear [Variable: Provider's Name]:

Based on [variable: payer's name]'s plan documents, the notifications made via [variable: payer's name]'s Member ID Card, and the your office's consent which became binding upon cashing [variable: payer's name]'s check, [variable: patient name] has novated and transfered the patient responsibility portion of the claim to ABC Company.

To that end, the patient/guarantor has transferd, via novation, the patient's responsibilities and liabilities to ABC Company. The agreement between [variable: patient name] and [Variable: Provider's Name] is hereby cancelled and discharged. ABC Company agrees to be responsible for all liabilities, payments and duites that that had been [variable: patient name]'s for the claim(s) listed below:

| Provider Name (city/state) | Patient Name | Date of Service | Total Owed | Provider Acct# |
|---|---|---|---|---|
| [variable field] | [variable field] | [variable field] | [variable field] | [variable field] |

Unless [Variable: Provider's Name] provides written notice providing the reason you object to this novation, and this new agreement between ABC Company and [Variable: Provider's Name] within ten (10) days, the novation will be deemed to be accepted by [Variable: Provider's Name]. ABC Company reserves the right to deem the novation vaild even if you provide a reason for objecting to the novation. Enclosed is a check in the amount of [Variable: $ amount] indicating good faith.

Sincerely,

ABC Company

FIG. 6E

Date: [Variable: date field]

[Variable: Provider's Name)]
[Variable: Address]
[Variable: City, State Zip code]

Re: Transfer of Patient Debt Liability to ABC Company

Dear [Variable: Provider's Name]:

Based on [variable: payer's name]'s plan documents, the notifications made via [variable: payer's name]'s Member ID Card, and the your office's consent which became binding upon cashing [variable: payer's name]'s check, [variable: patient name] has novated and transfered the patient responsibility portion of the claim to ABC Company.

To that end, the patient/guarantor has transferd, via novation, the patient's responsibilities and liabilities to ABC Company. The agreement between [variable: patient name] and [Variable: Provider's Name] is hereby cancelled and discharged. ABC Company agrees to be responsible for all liabilities, payments and duites that that had been [variable: patient name]'s for the claim(s) listed below:

| Provider Name (city/state) | Patient Name | Date of Service | Total Owed | Provider Acct# |
|---|---|---|---|---|
| [variable field] | [variable field] | [variable field] | [variable field] | [variable field] |

Please have an authroized reperesentative of [Variable: provider/creditor name] sign and date this document below acknowledging the novation, and this new agreement between ABC Company and [Variable: Provider's Name] and return it to ABC Company via US mail, facsimilie or email.

By: _____     Date:_____

(authroized representative of provider/creditor)

Sincerely,

ABC Company

FIG. 7A

Date: [Variable: date field]

[Variable: Provider's/Creditor's/Credit Bureau's Name]
[Variable: Address]
[Variable: City, State Zip code]

Re: Primary Guarantor for the debt

Dear [Variable: Provider's/Creditor's/Credit Bureau's Name]:

This letter confirms that ABC Company has agreed to be the primary guarantor for the debt listed below. If there are any questions, please contact us directly.

ABC Company is responsible for the debt(s) indicated below:

| Provider Name (city/state) | Patient Name | Date of Service | Total Owed | Provider Acct# |
|---|---|---|---|---|
| [variable field] | [variable field] | [variable field] | [variable field] | [variable field] |

Sincerely,

ABC Company

FIG. 7B

Date: [Variable: date field]

[Variable: Provider's Name]
[Variable: Address]
[Variable: City, State Zip code]

Re: Primary Guarantor for the debt

Dear [Variable: Provider's Name]:

This letter confirms that ABC Company has agreed to be the primary guarantor for the debt listed below. ABC Company is responsible for the debt(s) indicated below:

| Provider Name (city/state) | Patient Name | Date of Service | Total Owed | Provider Acct# |
|---|---|---|---|---|
| [variable field] | [variable field] | [variable field] | [variable field] | [variable field] |

Unless you provide written notice providing the reason you object to ABC Company acting as the guarantor for this debt to ABC Company within ten (10) days, the guaratnor status will be deemed to be accepted by [Variable: Provider's Name]. ABC Company reserves the right to deem the guarantor status valid even if [Variable: Provider's Name] provides a reason for objecting to the new guarantor status. ABC Company reserves the right to deem the guarantor status valid even if your office objects to the guaratnor status.

Enclosed is a check in the amount of [Variable: $ amount] indicating good faith.

Sincerely,

ABC Company

FIG. 7C

Date: [Variable: date field]

[Variable: Provider's Name]
[Variable: Address]
[Variable: City, State Zip code]

Re: Primary Guarantor for the debt

Dear [Variable: Provider's Name]:

This letter confirms that ABC Company has agreed to be the primary guarantor for the debt listed below:

| Provider Name (city/state) | Patient Name | Date of Service | Total Owed | Provider Acct# |
|---|---|---|---|---|
| [variable field] | [variable field] | [variable field] | [variable field] | [variable field] |

Please have an authroized reperesentative of [Variable: provider/creditor name] sign and date this document below confirming same, and return it to ABC Company via US mail, facsimilie or email.

By: _____    Date:_____
   (authroized representative of provider/creditor)

Sincerely,

ABC Company

FIG. 7D

Date: [Variable: date field]

[Variable: Provider's Name]
[Variable: Address]
[Variable: City, State Zip code]

Re: Primary Guarantor for the debt

Dear [Variable: Provider's Name]:

Based on [variable: payer's name]'s plan documents, the notifications made via [variable: payer's name]'s Member ID Card, and the your office's consent which became binding upon cashing [variable: payer's name]'s check, [variable: patient name] has transfered the patient responsibility portion of the claim to ABC Company.

This letter confirms that ABC Company has agreed to be the primary gurantor, and is responsible, for the debt listed below:

| Provider Name (city/state) | Patient Name | Date of Service | Total Owed | Provider Acct# |
|---|---|---|---|---|
| [variable field] | [variable field] | [variable field] | [variable field] | [variable field] |

Unless you provide written notice providing the reason you object to the transfer of this debt to ABC Company within ten (10) days, the transfer will be deemed to be accepted by [Variable: Provider's Name]. ABC Company reserves the right to deem the transfer vaild even if you provide a reason for objecting to the transfer. Enclosed is a check in the amount of [Variable: $ amount] indicating good faith.

Sincerely,

ABC Company

FIG. 7E

Date: [Variable: date field]

[Variable: Provider's Name]
[Variable: Address]
[Variable: City, State Zip code]

Re: Primary Guarantor for the debt

Dear [Variable: Provider's Name]:

Based on [variable: payer's name]'s plan documents, the notifications made via [variable: payer's name]'s Member ID Card, and the your office's consent which became binding upon cashing [variable: payer's name]'s check, [variable: patient name] has novated and transfered the patient responsibility portion of the claim to ABC Company.

Based on [variable: payer's name]'s plan documents, the notifications made via [variable: payer's name]'s Member ID Card, and the your office's consent which became binding upon cashing [variable: payer's name]'s check, [variable: patient name] has transfered the patient responsibility portion of the claim to ABC Company.
This letter confirms that ABC Company has agreed to be the primary gurantor, and is responsible, for the debt listed below:

| Provider Name (city/state) | Patient Name | Date of Service | Total Owed | Provider Acct# |
|---|---|---|---|---|
| [variable field] | [variable field] | [variable field] | [variable field] | [variable field] |

Please have an authroized reperesentative of [Variable: provider/creditor name] sign and date this document below confirming same, and return it to ABC Company via US mail, facsimilie or email.

By: _____    Date:_____
   (authroized representative of provider/creditor)

Sincerely,

ABC Company

FIG. 8

Date: [Variable: date field]

[Variable: Provider's/Creditor's/Credit Bureau's Name
[Variable: Address]
[Variable: City, State Zip code]

Re: Responsibility for payment

Dear [Variable: Provider's/Creditor's/Credit Bureau's Name]:

This letter confirms that ABC Company is responsible for payment of the debt listed below. If there are any questions, please have them contact us directly.

ABC Company is responsible for the debts indicated below:

| Provider Name (city/state) | Patient Name | Date of Service | Total Owed | Provider Acct# |
|---|---|---|---|---|
| [variable field] | [variable field] | [variable field] | [variable field] | [variable field] |

Sincerely,

ABC Company

FIG. 9A
ANALYSIS RESULTS FOR:

I. Seller Contact Information:

Full Name: John Doe  Tel#: 555-1212
Address: 123 East St  Email: na@na.com
City, State Zip: Orange, WI 38281

II. Details of the debt:

| Provider Name (address/city/state) | Patient Name | Date of Service | Total Owed | Provider Acct# |
|---|---|---|---|---|
| ABC Provider, York, PA | John Doe | 03/01/2011 | $3,933.22 | 47892 |

III. Post Analysis Results:

Analysis: Based On Global Variables
GA Est. Settlement: $2,432 -- 920
GA Calc. Resist. Rating: 7 --- 940
GA Cost to Work File: $272 --952
GA Risk Ratio: 62 ------- 954

Average Specific Provider
Discount: $2,322 ----------- 960

In-Network Average Insurance
Payment: $2,102 --------- 962

Out-Of-Network Average Insurance
Payment: $1,983 ------- 964

Medicare Allowed Amount Plus
Profit: $2,595 ---- 956

Medicare Rate vs. Cost-to-Charge
Ratio: $2,545 -------- 958

Charity Care: Not Available -- 970
 (bill too old)

Experience Rating Analysis
Total ERA Price: $2,697 ------- 922
Total ERA Resistance Rating: 6 -- 960
Total ERA Collection Experience:
 Law: N-137 COL:N-137
Total ERA Cost to Work File: $235 -- 942
Total ERA Risk Ratio: 37 ------ 958
 (based on 137 records)
Specific ERA Price: $2,447 -------- 924
Specific ERA Resistance Rating: 8
Specific ERA Collection Experience:
 Law: N-137 COL:N-137 ------ 932
Specific ERA Cost to Work File:$220 - 944
Specific ERA Risk Ratio: 35 ---------- 946
 (based on 44 records)
DMDRA Price: $2,543 --------- 926
DMDRA Resistance Rating 7 ------ 938
DMDRA Collection Experience:
 Law N-137 COL:N-137 -------- 934
DMDRA Cost to Work File: $254 --- 948
DMDRA Risk Ratio: 39 --------- 950
 (based on 23 records)

FIG. 9B

Example #1: Total ERA Collection Experience: ---------------- 990

*General Adverse Events Anticipated for [variable: inputted provider]*

Number of records in experience database: 137 records

No Lawsuits – 137 records searched

No Negative Credit rating – 137 records searched

No refusal of provider to treat patient

In-house Collection calls and letters begin at 120 days from DOS for amount greater then $20

Outside Collection calls and letters begin at 190 days from DOS amount greater then $200

* Law firm used for collection begins at 260 days for amount greater then $600

*Adverse Event Forecasting for Your Specific Debt with [variables: inputted provider], for the Amount of [variable: amount owed] for Date of Service [variable: DOS].*

100% chance of an in-house collections calls and letters being around [variable: date].

100% chance of an outside collections calls and letters begin around [variable: date].

0% chance of the provider refusing to treat patient again.

0% chance of a negative credit rating being filed.

0% chance of a lawsuit being filed.

Example #2: Total ERA Collection Experience: -------------- 995

*General Adverse Events Anticipated for [variable: inputted provider]*

Number of records in experience database: 137 records

Lawsuit after 410 days from DOS for amounts greater then $5,000

Refusal of provider to treat patient for amounts greater than $7,000

Negative Credit rating starting at 260 days from DOS for amounts greater then $425

In-house Collection calls and letters starting at 160 days from DOS for amounts greater then $10

Outside Collection calls and letters start at 190 days from DOS for amounts greater then $500

* Law firm used for collection starting at 260 days from DOS for amounts greater then $700

*Adverse Event Forecasting for Your Specific Debt with [variables: inputted provider], for the Amount of [variable: amount owed] for Date of Service [variable: DOS].*

100% chance of an in-house collections calls and letters being received around [variable: date].

100% chance of an outside collections calls and letters begin received around [variable: date].

64% chance of a negative credit rating being filed around [variable: date].

18% chance of a lawsuit being filed around [variable: date].

62% chance of the provider refusing to treat patient again.

Note: * = law firm used to send dunning letter, but not litigating the matter.

FIG. 9C

REPORT ON ESTIMATED SETTLEMENT PRICE WITH PROVIDER

I. Details of the debt:

| Provider Name (address/city/state) | Patient Name | Date of Service | Total Owed | Provider Acct# |
|---|---|---|---|---|
| ABC Provider, York, PA | John Doe | 03/01/2011 | $3,933.22 | 47892 |

II. Post Analysis Results:

Total ERA Price: $2,697 **
Total ERA Resistance Rating: 6
** Based on the lowest resistance rating of "6" PODS entity suggests this settlement amount GA Est. Settlement: $2,432
GA Calc. Resist. Rating: 7

DMDRA Price: $2,543
DMDRA Resistance Rating 7

Specific ERA Price: $2,447
Specific ERA Resistance Rating: 8

DMDRA Price: $2,543
DMDRA Resistance Rating 7

Average Specific Provider Discount: $2,322

In-Network Average Insurance Payment: $2,102

Out-Of-Network Average Insurance Payment: $1,983

Medicare Allowed Amount Plus Profit: $2,595

Medicare Rate vs. Cost-to-Charge Ratio: $2,545

FIG. 10

Instructions To Repair Your Credit

A "financial responsibility letter" will be emailed to you shortly. Follow the credit reporting agency's disputes process and dispute the charge(s) based on the liability being the responsibility of another party. For proof that the liability is the responsibility of a third party (a/k/a another party), attach the "financial responsibility letter" that you receive from us.

If disputing the charge is not successful at this time, please let us know so that we may update you when the account is settled in full. You may dispute that chrage at that time.

Please note: If the credit agency refuses to take the negative credit rating off your credit report, you should ask the credit bureau that the negative mark have a noatation that you have resolved the outstadning balacne with the creditor.

FIG. 11

[COMPANY LETTERHEAD]

[Date]

[Name of patient]
[Address]
[City, State Zip code]

Re: Purchase of your patient responsibility

Dear [Name of patient]:

Per the enclosed Explanation of Benefits your patient responsibility is $3,933.22. If you desire, [Name of Company] will accept liability for the "patient responsibility" portion of your debt per our standard terms and conditions for $2,130.00.

If you desire to transfer your debt you may do this online or via US. Mail. If you desire you may go to www.[url].com and enter the code [Code #]. You will then be prompted to complete the transaction.

If you desire to us the US Mail, simply check the box below and enter your credit card information or enclose a check and mail back to [Company]

-------------------------------------------------- CUT HERE --------------------------------------------------

Claim # 378943798   Patient Responsibility: $3,933.22   Accepting Amount: $2,130.00

By Signing her I agree to the terms and conditions of [Company]:_____

Type of Credit Card:_____

Card #:_____   Security Code:_____ Exp date:_____

FIG. 12

NON-CONTRACTED NEGOTIATED DISCOUNT GUIDELINES

BILLED CHARGES $5,000.00 TO $9,999.99 will be eligible for a 5% discount $10,000.00 and over will be eligible for a 10% discount Please use these guidelines for future reference.

If any questions, please contact ███████ Patient Accounting, Negotiated Discounts @ ██

Thanks

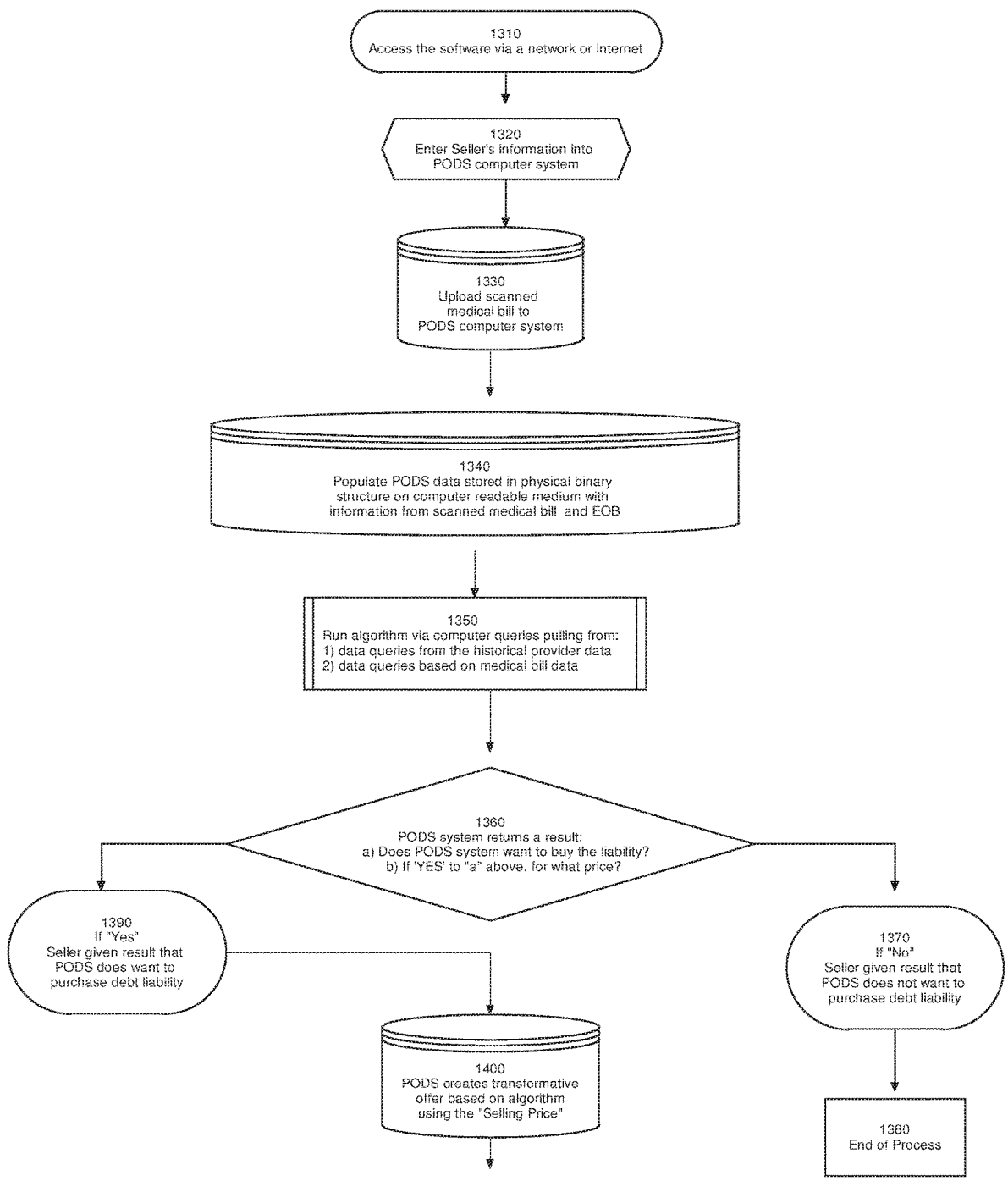

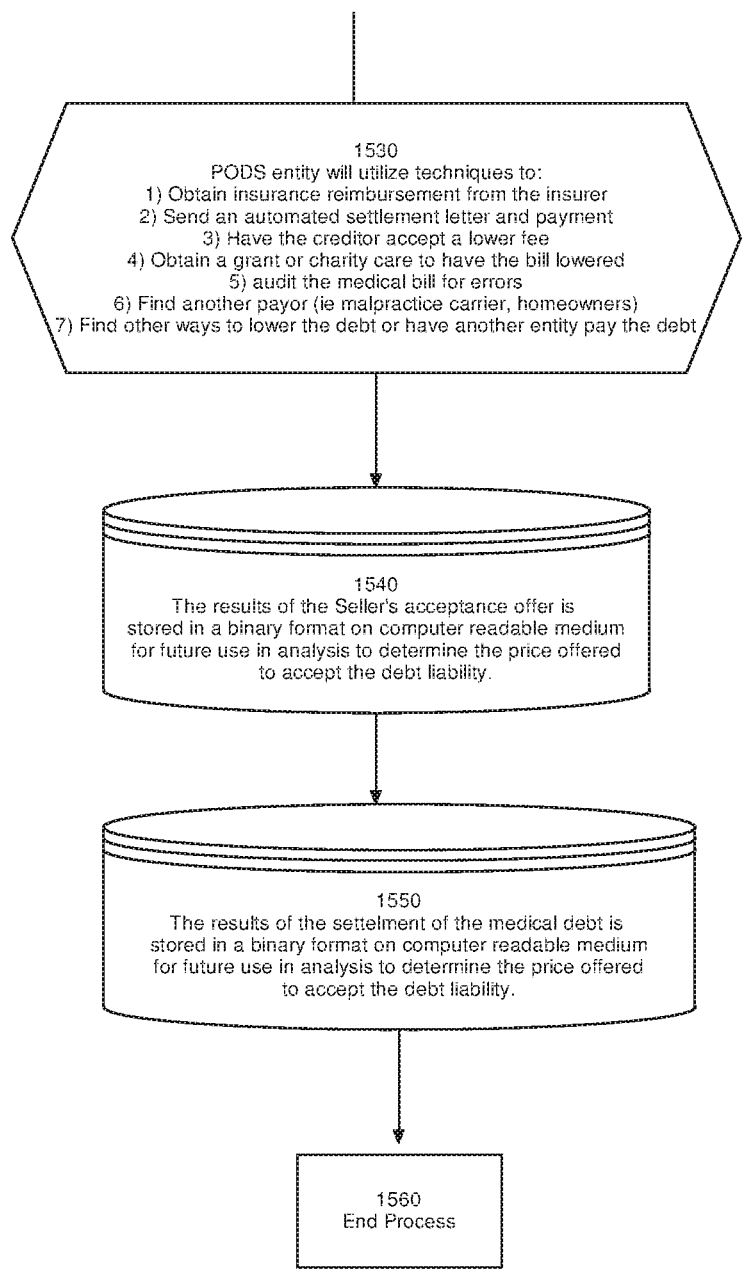

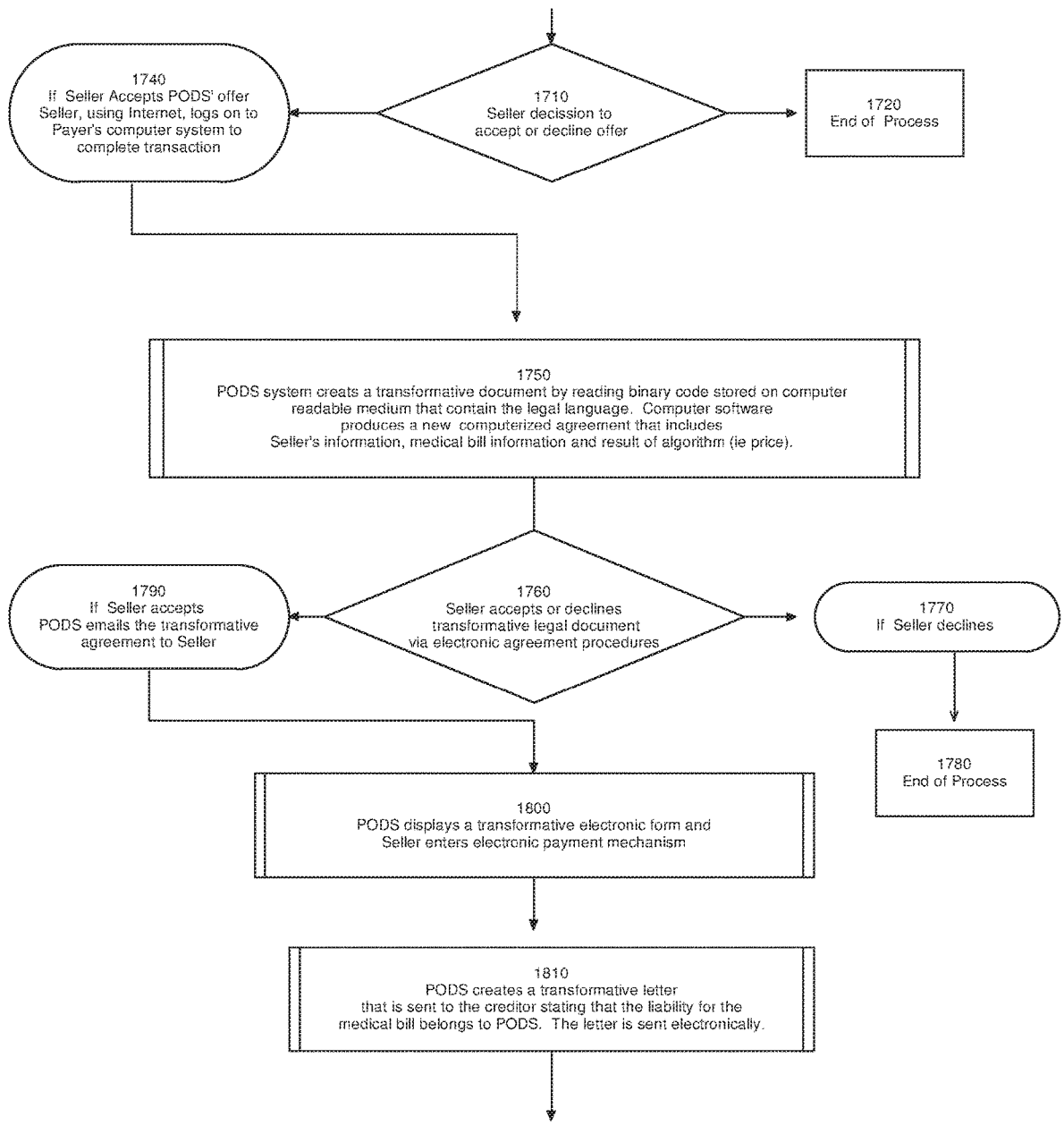

FIG. 15

OFFER TO ACCEPT DEBT LIABILITY

PODS entity will accept the liability for the account(s) listed below for $ [variable: Selling Price]

Account Information For Debt:

| Provider Name (city/state) | Patient Name | Date of Service | Total Owed | Provider Acct# |
|---|---|---|---|---|
| [variable field] | [variable field] | [variable field] | [variable field] | [variable field] |

[ I Accept Offer ]   [ I Decline Offer ]

FIG. 16

BEST WAY TO APPROACH PROVIDER FOR DISCOUNT REPORT

Provider Name: ABC Physician

Account Information For Debt:

| Provider Name (city/state) | Patient Name | Date of Service | Total Owed | Provider Acct# |
|---|---|---|---|---|
| [variable field] | [variable field] | [variable field] | [variable field] | [variable field] |

Date to approach provider for a discount:    June 1, 2012 *

* The fiscal year end is July, $31^{st}$ - approaching the facility two months in advance allows maximum leverage to obtain a lower settlement price]

Person to Approach at Provider Office/Facility:  Mary

Based on the mathematical model, Mary is the best person to contact.
Below is the average discount per staff member.

Mary – average reduction on bills: 45%
Bob  – average reduction on bills: 26%
John – average reduction on bills: 0%
Jane – average reduction on bills: 22%

Table #1

FIG. 19A

| UID - Provider | DOS | TBC | IAA | DS | BAL | RES | STL |
|---|---|---|---|---|---|---|---|
| 1-ABC Physician | 1/18/2007 | $1,234.00 | $911.00 | 3/8/2008 | $323 | 5 | $180 |
| 2-ABC Physician | 1/28/2008 | $7,652.00 | $5,109.00 | 6/8/2008 | $2,543 | 5 | $1,902 |
| 3-ABC Physician | 4/23/2007 | $4,323.00 | $3,029.00 | 7/9/2007 | $1,294 | 10 | $1,294 |
| 4-ABC Physician | 3/23/2006 | $3,832.00 | $3,036.00 | 6/29/2006 | $796 | 6 | $622 |
| 5-XYZ Hospital | 1/8/2008 | $23,211.00 | $11,980.00 | 3/8/2008 | $11,231 | 7 | $3,212 |
| 6-XYZ Hospital | 1/8/2008 | $22,633.00 | $0.00 | 6/8/2008 | $22,633 | 8 | $2,392.00 |
| 7-XYZ Hospital | 1/8/2008 | $9,222.00 | $0.00 | 9/8/2008 | $9,222 | 10 | $9,222 |
| 8-XYZ Hospital | 1/8/2008 | $28,463.00 | $16,229.00 | 1/8/2010 | $12,234 | 7 | $4,293 |
| 9-PDQ Clinic | 2/12/2007 | $1,432.00 | $889.00 | 5/4/2008 | $543 | 3 | $123 |
| 10-PDQ Clinic | 4/4/2007 | $4,547.00 | $2,313.00 | 12/6/2008 | $2,234 | 4 | $980 |
| 11- A collections | 2/3/2006 | $6,732.00 | $4,079.00 | 4/5/2007 | $2,653 | 7 | $1,272 |
| 12- A collections | 4/16/2006 | $4,623.00 | $2,991.00 | 6/5/2007 | $1,632 | 7 | $900 |
| 13- B Law Office | 6/3/2006 | $5,825.00 | $4,859.00 | 9/5/2007 | $966 | 7 | $800 |
| 14- B Law Office | 9/16/2006 | $6,354.00 | $5,531.00 | 10/5/2007 | $823 | 7 | $540 |

Note: # 11 and #12 above are records for the specific debt collection company used to collect the debt. The data structure may track by provider name and/or collection company name.
Likewise #13 and #14 above track the specific law office used to collect the debt.

FIG. 19B

| COL | LAW | IN | HI | ELEC | DED | PC | CR | M |
|---|---|---|---|---|---|---|---|---|
| Y | N | N | N | N | Y | 99291 | 620 | Mary |
| N | N | N | Y | N | N | 99372 | 700 | Bob |
| N | N | N | Y | N | N | 99363 | 720 | John |
| N | N | N | Y | N | N | 99372 | 680 | Jane |
| N | N | N | Y | N | N | 99362 | 650 | Cindy |
| N | N | N | Y | N | N | 99362 | 677 | Rick |
| Y | N | N | Y | N | N | 99163 | 712 | Paul |
| Y | N | N | Y | N | N | 99628 | 694 | Jack |
| Y | N | N | Y | N | N | 99310 | 723 | David |
| Y | N | N | Y | N | N | 99215 | 656 | Eric |
| Y | N | N | Y | N | N | 99263 | 674 | Rick |
| Y | N | N | Y | N | N | 99625 | 711 | Rick |
| | N | N | Y | N | N | 99362 | 686 | Neil |
| Y | | | Y | | Y | 99673 | 674 | Ted |

FIG. 19C

| ME | F | A | B | P | PFS | PAY | DEN | APL | Patient name & contact info | Seller name & contact info | NCR | DNCR | TYPE |
|---|---|---|---|---|---|---|---|---|---|---|---|---|---|
| N | 31-Dec | N | N | N | N | Uninsured | N | N | J Doe, NY | J Doe, NY | Y | 6/18/2007 | OUTCOL |
| N | 31-Aug | N | N | N | N | Humana | N | N | D Red, PA | D Red, PA | N | | |
| N | 31-Jul | N | N | N | N | Medicaid | N | N | K Pen, CA | K Pen, CA | N | | |
| N | 30-Nov | Y | N | N | N | Medicare | N | N | C Yu, Ca | C Yu, Ca | N | | |
| Y | 30-Jan | N | N | N | N | Aetna | N | | K Lin, NJ | K Lin, NJ | N | | |
| N | 28-Feb | N | Y | N | N | Blue Cross | N | N | L Pew, PA | L Pew, PA | N | | |
| N | 31-Dec | N | N | N | N | Humana | Y | Y | W Lag, UT | W Lag, UT | N | | |
| N | 31-Dec | N | N | N | N | Blue Cross | Y | Y | A Ait, NY | A Ait, NY | Y | 6/8/2008 | OUTCOL |
| N | 31-Dec | N | N | N | N | Aetna | N | N | P Lug, NY | P Lug, NY | Y | 9/1/2007 | OUTCOL |
| N | 28-Feb | N | N | N | N | Humana | N | N | R Bet, CA | R Bet, CA | Y | 10/15/2007 | OUTCOL |
| N | 31-Dec | Y | N | N | N | GHI | N | | M Nit, TX | M Nit, TX | Y | 10/15/2006 | OUTCOL |
| N | 31-Dec | N | N | N | N | Medicare | N | N | A Bed, TX | A Bed, TX | Y | 11/17/2006 | OUTCOL |
| N | 31-Dec | N | N | N | N | UMR | N | N | N Fel, VA | N Fel, VA | Y | 5/3/2007 | OUTCOL |
| N | 31-Dec | N | N | N | N | GHI | N | N | P, Wig, FL | P, Wig, FL | Y | 12/20/2006 | OUTCOL |

DATE: 08 XX XXXX  
ACCOUNT: XXXX XXXX  
August 16, 20XX  
BALANCE: $ XXXX

* IMPORTANT NOTICE *

XXXX XXXX  
XXXX XXX XXXX XXXX XX

Although we have made numerous attempts to collect the above outstanding debt, we still show a balance due on your account.  2000

We must receive immediate payment of your account or we will assume that you are unwilling to resolve your obligation voluntarily. If payment in full is not received, we will proceed with further collection efforts.

Please note that your account has been reported to a credit reporting agency as an unpaid collection. Assuming that you value your credit you should pay this outstanding bill immediately to improve your credit file.

When calling RRS regarding your statement please refer to this account number: XXX XX

| CREDIT FOR | AMOUNT | INTEREST | FEES | TOTAL |
|---|---|---|---|---|
|  | XXX.98 | 0.00 | 0.00 | XXX.98 |
| TOTAL | XXX.98 | 0.00 | 0.00 | XXX.98 |

To pay online visit xxxx xxxx xxxx. To pay by check or credit card, complete the boxes below and mail this letter back with your payment.

A convinence fee of $3.50 will be charged for payments made by credit card ACR or by debit card.

IF YOU WANT TO PAY BY CREDIT CARD CIRCLE ONE AND FOR THE INFORMATION BELOW

| CARD NUMBER | EXP DATE |
|---|---|
| CARD HOLDER NAME | CVV |
| DATE: XXXX   PAY THE AMOUNT XXX.XX | ACCOUNT XXXX XX |
| SIGNATURE | AMOUNT PAID |

*This communication is from a debit collector and is an attempt to collect a debt. Any information obtained will be used for that purpose.* xxxx xxxx xxxx xxxxx

[LETTERHEAD]

[date]

Mr John Doe
[address]
[city, state, zip]

Re: $4,242 outstanding debt with ABC Hospital

Dear Mr. Doe:

ABC Hospital has engaged a collection company to obtain the balance due from you; they may also take legal action against you. TO YOUR RESCUE - PODS Entity will accept liability for debts owed by people like yourself but provides you with a substantial savings. After evaluating your debt and the resistance anticipated in settling this debt with ABC Hospital, PODS Company would be willing to accept complete liability for your debt with ABC Hospital for the sum of $2,916. If this arrangement is acceptable, please fill-out the enclosed agreement and mail it back to us with payment. Alternatively, you may complete this transaction by logging into our web site at www.podsentity.com and entering the offer code #23834.

Sincerely,

[name]

------------------------------------------- PAYMENT COUPON  CUT HERE -------------------------------------------

___ Visa     ___ Mastercard     ___ American Express

PODS Entity
PO Box XXX
Philadelphia, PA 19103

Card Number:_____ Exp date:_____

Card Holder Name:_____ CVV:_____

Amount paid: $2,916     PODS Acct# 23834

Signature:_____     Date:_____

FIG. 23A

```
┌─────────────────────────────────────────────────────────┐
│                                                         │
│           New Jersey State Department of Health         │
│             Care for the Uninsured Program              │
│                                                         │
│              NEW JERSEY HOSPITAL CARE                   │
│           PAYMENT ASSISTANCE FACT SHEET                 │
│                                                         │
└─────────────────────────────────────────────────────────┘
```

WHAT IS THE HOSPITAL CARE PAYMENT ASSISTANCE PROGRAM?

The New Jersey Hospital Care Payment Assistance Program (Charity Care Assistance) is free or reduced charge care which is provided to patients who received inpatient and outpatient services at acute care hospitals throughout the State of New Jersey. Hospital assistance and reduced charge care are available only for necessary hospital care. Some services such as physician fees, anesthesiology fees, radiology interpretation, and outpatient prescriptions are separate from hospital charges and may not be eligible for reduction.

WHERE DOES FUNDING FOR HOSPITAL CARE PAYMENT ASSISTANCE COME FROM?

The source of funding for hospital care payment assistance is through the Health Care Subsidy Fund administrated under Public Law 1997, Chapter 263.

WHO IS ELIGIBLE FOR HOSPITAL CARE PAYMENT ASSISTANCE?

Hospital care payment assistance is available to New Jersey residents who:

1. Have no health coverage or have coverage that pays only for part of the bill; and
2. Are ineligible for any private or governmental sponsored coverage (such as Medicaid); and
3. Meet both the income and assets eligibility criteria listed below.

Hospital assistance is also available to non-New Jersey residents, subject to specific provisions.

Income Criteria

| Income as a Percentage of HHS Poverty Income Guidelines | Percentage of Charge Paid by Patient |
|---|---|
| Less than or equal to 200% | 0% |
| Greater than 200% but less than or equal to 225% | 20% |
| Greater than 225% but less than or equal to 250% | 40% |
| Greater than 250% but less than or equal to 275% | 60% |
| Greater than 275% but less than or equal to 300% | 80% |
| Greater than 300% | 100% |

If patients on the 20% or 80% sliding fee scale are responsible for qualified out-of-pocket paid medical expenses in excess of 30% of their gross annual income (i.e. bills unpaid by other parties), then the amount in excess of 30% is considered hospital care payment assistance.

FIG. 23B

<u>Assets Criteria</u>

Individual assets cannot exceed $7,500 and family assets cannot exceed $15,000. Should an applicant's assets exceed these limits, he/she may 'send down' the assets to the eligible limits through payment of the excess toward the hospital bill and other approved out-of-pocket medical expenses.

HOW ARE INDIVIDUALS MADE AWARE OF THE AVAILABILITY OF HOSPITAL CARE PAYMENT ASSISTANCE?

Hospitals post signs in English, Spanish and any language which is spoken by 10% or more of the population in the hospital's service area. These signs are posted in appropriate areas of the facility such as the admission area, the business office, outpatient clinic areas, and the emergency room. The sign informs patients of the availability of hospital assistance and reduced charge care, gives a brief description of the eligibility criteria, and directs the patient to the business office or admissions office of the hospital. Every patient should receive a written notice of the availability of hospital care payment assistance and medical assistance.

WHAT ARE THE SCREENING PROCEDURES FOR THIRD PARTY PAYERS AND MEDICAID?

All charity care applicants must be screened to determine the potential eligibility for any third party insurance benefits or medical assistance programs that might pay towards the hospital bill.

Patients may not be eligible for the hospital care payment assistance program until they are determined to be eligible for any other medical assistance programs.

Patients are responsible to obtain a financial screening from the hospital in a timely manner. Usually, a patient must apply for Medicaid within 3 month from the date of hospital services.

Once the hospital has informed the patient about medical assistance and/or makes the referral properly, if the patient fails to cooperate or does not go for screening in a timely manner, the hospital has the option to bill the patient and pursue collection efforts, regardless of eligibility for hospital care payment assistance.

HOW DOES SOMEONE APPLY FOR HOSPITAL CARE PAYMENT ASSISTANCE?

The patient or prospective patient must apply for hospital care payment assistance at the hospital from which he/she plans to obtain or has obtained services. The patient should apply at the business office or admissions office of the hospital. The patient or responsible party must answer questions related to his/her income and assets, as well as provide documentation of the income and assets. The hospital will make a determination of whether the applicant is eligible as soon as possible, but no more than ten working days from the time a complete application is submitted. If the request does not include adequate documentation to make a determination, the request shall be denied. The applicant will then be allowed to present additional documentation to the hospital. The applicant has up to one year from the date of service to apply for hospital assistance and provide the hospital with a completed application. Applicants found ineligible may reapply at a future time when they present themselves for services and believe their financial circumstances have changed.

The Department of Health has a toll-free number to assist with any questions or concerns. Please call the Health Care for the Uninsured Program during business hours at 1-866-588-XXXX.

FIG. 24

Expedited Agreement

To:
Fax #:
From: Fee Negotiation Department, (866) 568-XXXX - Phone
Date:

Patient:                              Acc #:                    UNAVAILABLE
Date of Service:                      Multi Plan Claim #:
Payer: Cigna                          Payer Claim #:

Cigna Healthcare has contacted with XXXX to facilitate resolution of the above referenced services because the patient has gone "out of work". This agreement may expedite payment and decrease the patient's responsibility.

We are asking that [Provider] agree to accept the Expedited Price listed below (less deductible, co-insurance, or co-payment) as the full payment for services rendered on the following date(s):

| Date of Service | Billed charges | Expedited Price |
|---|---|---|
| 01/01/2017 | $414.54 | $257.01 |

Upon our receipt of this agreement executed by you, payment will be issued within 10 business days.

Your signature below indicates your acceptance of the Expedited Price and your agreement not to bill the patient (or other financially responsible party) for the difference between the Billed Charge and the Expedited Price. You retain the right to bill the patient (or other financially responsible party) for items not covered under the patient's benefit plan and for any patient-responsible amounts such as applicable deductibles, co-insurance or co-payments.

XXXX is not financially responsible for any payments due to the Provider. Payment of benefits, if any, is subject to the terms and conditions of the patient's policy. Therefore, this letter of agreement does not constitute, nor should it be construed as a guarantee of benefit payment by the Payer. Please feel free to contact us if you have any questions or concerns.

Thanks,
XXXXX's Fee Negotiation Department, (866) 568-XXXX.

PLEASE SIGN BELOW AND FAX BACK PROMPTLY TO:
 DO NOT SEND COVER SHEET

[ ] Check here if you are interested in receiving additional information regarding a Global Agreement that will eliminate case by case faxes, and expedite handing for all future claims. You may also contact us for additional information at (866) 568-XXXX.

_____            _____
Authorized Representative's Signature / Date           Print Name / Title

*Immediate Return Requested*

DDD: November

To:  From:

Provider:  Phone:

Phone:  Fax:

Fax:  Alt. Fax:

Patient:  GCS #:

Pat Acct#:  Claim ID:

Client: Aetna

Provider agrees to accept the "Adjusted List Price" set forth below, less any deductible, co-pay, coinsurance, usual and customary reductions, and charges for non-covered items/services, if applicable, as payment in full for the following services that have been provided to the above referenced patient.

| Date of Service | Provider's List Price | Adjusted List Price |
|---|---|---|
|  | $1,200.00 | $960.00 |

Upon Provider's execution and return of this agreement, Payer agrees to release payment to Provider within a timely manner after the receipt of this signed agreement.

Provider agrees not to balance bill the patient or patient's family (except for deductible, co-pay, coinsurance, usual and customary reductions, and charges for non-covered items/services, if applicable). Provider further agrees that any late charges that are not included in the aforementioned "Provider's List Price" relating to this claim may be adjusted by the same percentage reduction. To our knowledge, no managed care discounts apply to this account.

Provider acknowledges and agrees that (1) _____, is not liable for any payments due Provider for any fee or charge whatsoever relating in any way to the aforementioned claims, (2) that this agreement does not constitute, nor shall it be construed as, a guarantee of Payer's payment, (3) all applicable benefits to be paid by Payer are subject to Payer's policy terms and conditions, and (4) this memorandum will be null and void if Payer determines that no benefit is payable for such claim.

_____  _____
Authorized Provider Signature  Date

_____  _____
Print Name  Title

All disclosure personal health information is handled in accordance with HIPAA provisions.

Problem: The medical loss ratio instituted by the Affordable Care Act is causing financial stress on health insurance companies. To alleviate this, insurance companies are looking at alternative revenue sources including offering employee assistance program and wellness programs.

Solution: The current disclosure is a service offering that is easily implemented, maintains the core competencies of a payer and can produce revenue as indicated below:

Market Segment #1 includes: Out-of-network claims and claim denials

Market Segment #2 includes: Non-covered benefits (dental, elective procedures, etc)

Financial Assumptions For Aetna – Market Segment #1:
These projections do not include the self funded plans that Aetna administers.
These projections do not include in-network patient responsibilities bills Aetna's Annual Claims Payout (2009): $11.9B
Percent out-of-network and denied care (estimated): 18%
Average reduction of a medical bill: 50%

---

Total Claims Universe for this invention: $2,142,000,000
    Above based on ($11.9B * 18%)
Applying 33% reduction on the universe based on insurance payment: $706,860,000
    Above based on ($2,142,000,000 - 33%)
Aetna Gross Annual Profits =
  (Total paid to Aetna by patient - ((monies paid to provider) + operating costs)))

FIG. 26B

Market Segment #1

- If Aetna provides a 20% discount to the patient

| | |
|---|---|
| Total Claims | $706,860,000 |
| Income from Patient (20% of total) | $565,488,000 |
| Provider Payment | $353,430,000 |
| Aetna Annual Profit at 20% Discount | $212,058,000 minus operating costs |

- If Aetna provides a 30% discount to the patient

| | |
|---|---|
| Total Claims | $706,860,000 |
| Income from Patient (30% of total) | $494,802,000 |
| Provider Payment + Cots (50%) | $353,430,000 |
| Aetna Annual Profit at 30% Discount | $141,372,000 minus operating costs |

Financial Assumptions – Market Segment #2:
Total Claims Universe (best guess): $2,000,000,000
Projected Aetna Profit: $25,000,000

Total Financial Assumptions:
Market Segment #1 (at 20%) + Market Segment #2 = ≈ $237,058,000/yr in revenue to
Projected Annual Aetna Revenue: $237,058,000/yr medical loss ratio information

The Affordable Care Act requires health insurers in the individual and small group markets to spend at least 80% of the premiums they receive on heathcare services and activities to improve healthcare quality (in the large group market, the amount is 85%). This is referred to as the medical loss ratio (MLR) rule or the 80/20 rule. If a health insurer does not spend at least 80% of the premiums it receives on healthcare services and activities to improve health care quality, the insurer must rebate the difference.

A health insurer's medical loss ratio is determined separately for each state's individual, small group, and large group markets in which the health insurer offers health insurance. In some states, health insurers must meet a higher or lower medical loss ratio. No later than August 1, 2012 health insurers must send any rebates due for 2011 and information to employers and individuals regarding any rebates due for 2011.

You are receiving this notice because Blue Shield of California and Blue Shield of California Life and Health Insurance Company had a medical loss ratio for 2011 that met or exceeded the required medical loss ratio. For more information on medical loss ratio, visit blueshieldca.com/MLRinfo or www.healthcare.gov.

EXPLANATION OF BENEFITS
NEED HELP? CALL XXX-XXXX

THIS IS NOT A BILL

CHECK IS ENCLOSED

| PAYMENT SUMMARY ||
|---|---|
| We Sent Check To: | |
| Check Number: | Check Amount: $ 3,320.50 |
| Claim Number: | Payment Amount: $ 3,320.50 |

| |
|---|
| Contract holder Name: |
| Member ID: |
| Group Name: |
| Group ID: |
| Claim activity: |
| Claim Number: |

| EXPLANATION AT A GLANCE |
|---|
| Date Of Service: |
| Provider: |
| We Sent Check To: |
| Check Number: |
| Provider May Bill You (If Not Already Paid): $ 4,262.43 |

| MEMBER RESPONSIBILITY | | | | | | |
|---|---|---|---|---|---|---|
| Provider Date Of Service Type Of Service Service Code (Number Of Services) | Provider's Charge | Non Covered Charges | Plan Allowance (Covered Charges) | Health Plan Pays You | Amount You Owe Provider (Total Of Shsded Columns) | See Remarks |
| THERAPEUTIC INJECTION J1745 (50) | 4262.43 | 941.93 J4053 | 3320.50 | 3320.50 | 942.93 | |
| TOTALS | 4262.43 | 941.93 | 3320.50 | 3320.50 | 941.93 | J1034 |

| Explanation of Remark Codes |
|---|
| J1034 – your provider is out of network. If you have not yet paid the provider, you are responsible to pay the amount the provider may bill you. |
| J4053 – this is the difference between the provider's charge and our allowance. |

FIG. 28

ABC PAYER COMPANY - EXPLANATION OF BENEFITS

Date: [Variable: date field]

Insured: [Variable: Insured's Name]
[Variable: Address]
[Variable: City, State Zip code]

Insured's ID# [variable field]

Claim# [variable field]

| Provider Name | Patient Name | Date of Service | Total Billed | Non-Allowed Charges | Insurance Paid | Patient Responsibility | Notes | ABC Payer Offer* |
|---|---|---|---|---|---|---|---|---|
| [variable field] | [variable field] | [variable field] | [variable field] | [variable field] | [variable field] | [variable field] | [variable field] | [variable field] |

Notes: [variable field to incorporate notes on the processing of this claim]

- ABC Payer will assume full liability for the [variable field for amount owed] owed to the [variable provider name], as outlined above in the "patient responsibility" section in exchange for a payment of [variable field for ABC Payer Offer]. To accept this offer go to www.abcpayer.com and input the claim number listed above. You will be prompted to pay by credit card. You may also mail the enclosed offer with payment to ABC Payer Company.

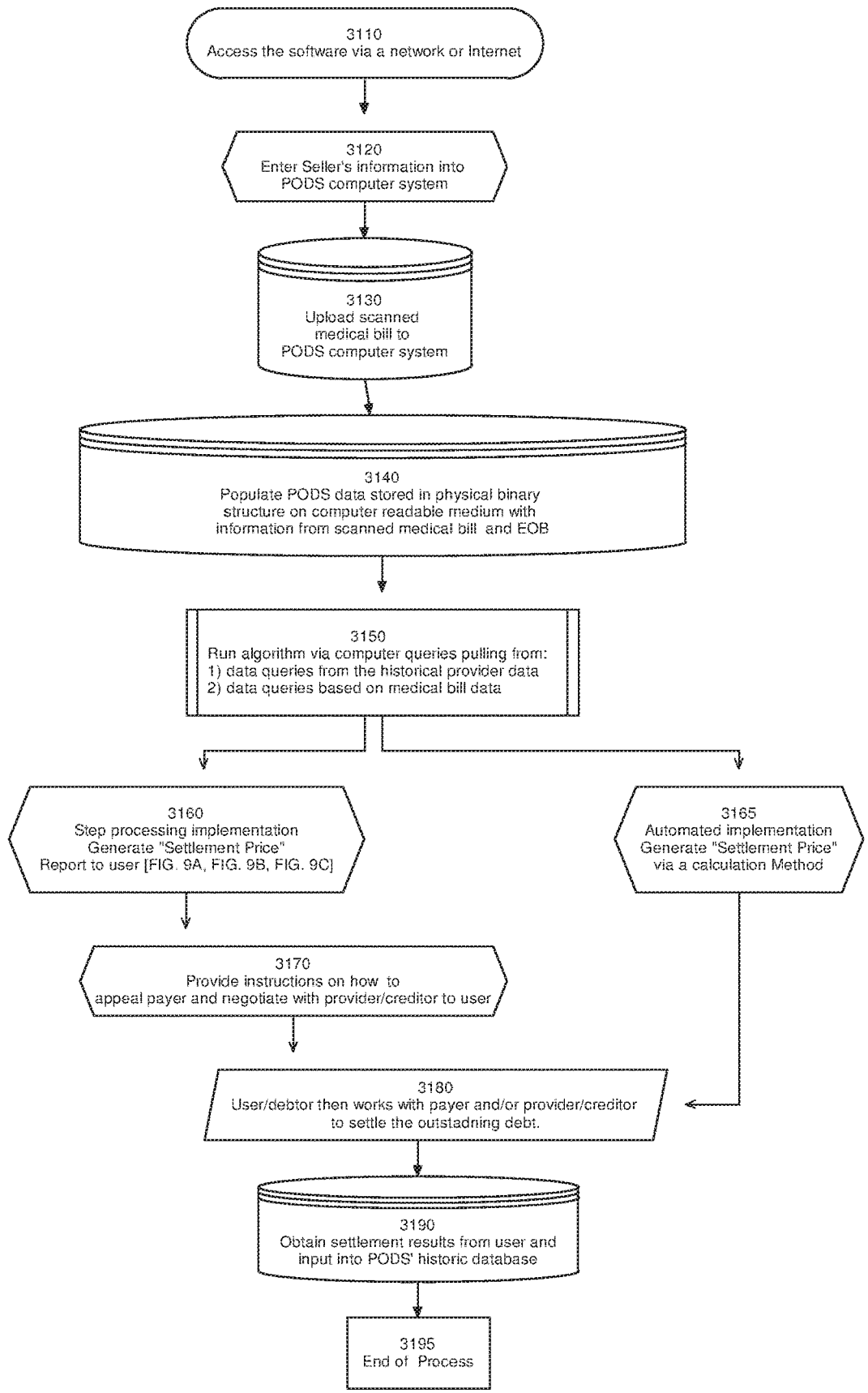

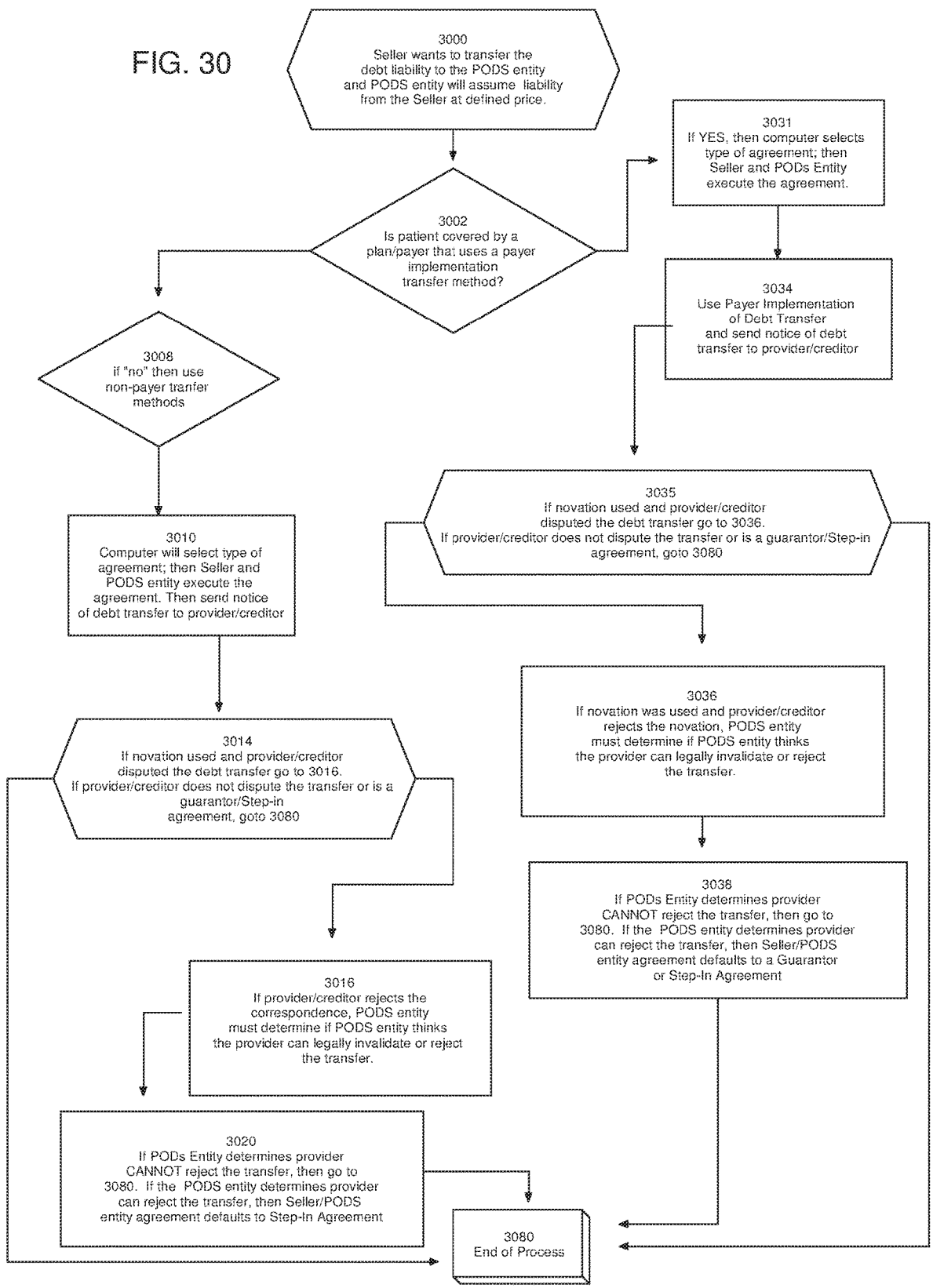

FIG. 32A

Quick Quote

First Information

How many bills do you have?  [ 1 ]

In what state was the care provided?  [ Pennsylvania ]

Your Contact Information

First Name :  [ Robert ]

Your Zip Code :  [ 19104 ]

Email address (we email you the quotation):  [ your_address_here@gmail.com ]

NEXT STEP --- # 3201

FIG. 32B

Quick Quote

Bill Details: 1 of 1          Previous Bill     Enter Next Bill

Provider Name :                   3B Orthopedics

Date of Service (date of admission):     4  ▾  2  ▾  2015  ▾

Total amount of bill :            8000

Total outstanding balance :       8000

Was the care in/out of network :  Out of Network  ▾

Amount you owe for deducible:     0

Insurance Company:                CIGNA

Have you completed the appeals process?     I'm Not Appealing This  ▾

Agreements and Efforts:

Did you enter into a monthly a payment agreement for this bill?     No  ▾

Has the provider been requested to lower the bill?     No  ▾

Is the provider a hospital or medical office?     Hospital  ▾

Significant events about which you feel we should know

Previous Bill     Enter Next Bill

GET QUOTE --- # 3210

FIG. 33

From: "PODS entity"
To: <user@nowhere.net>
Sent: Monday, April 13, 2015 7:20 PM
Subject: Fw: Quick Quote

Your Quotation

Medical Bills PODS entity Will Buy:

| Provider Name | Date of Service | Outstanding Balance |
|---|---|---|
| 3B Orthopedics | 4/2/2015 | $ 8000.00 |

$ 5308.95 - is PODS entity's price to assume liability for the bill(s) listed above. records.

If you would like to continue to the next step, please forward copies of the provider's itemized bill (or CMS 1500 form or UB-04 form), the insurance company's explanation of benefits and any collection letters. We may request the medical records at a future date.

Thank you,
The PODS entity

COMPUTER SOFTWARE, PROCESSES, ALGORITHMS AND INTELLIGENCE THAT FORECAST A SETTLEMENT PRICE AND NEGATIVE ACTIONS TAKEN BY PROVIDERS AGAINST PATIENTS, WITH DEBTS OWED, BASED ON SPECIFIC VARIABLES

CROSS REFERENCE TO RELATED APPLICATION

This application is a Divisional of U.S. patent application Ser. No. 14/832,372 filed Aug. 21, 2015, which claims priority to U.S. Provisional Patent Application Ser. No. 62/150,031 filed Apr. 20, 2015 entitled "Computer software, processes and algorithms that automate and solve problems in the field of profiting from the purchase of debt liability."

This application further claims priority to, and is a nonprovisional of U.S. Patent Application Ser. No. 62/043,621 filed Aug. 29, 2014 entitled "Computer implemented process for calculating and communicating offers to a Debtor to eliminate a Debtor's debt obligation to a creditor by having a third party entity pay the debt purchase amount to fully assume the Debtor's debt obligation, including novation."

This application further claims priority to, and is a continuation-in-part of U.S. patent application Ser. No. 14/257,499 filed Apr. 21, 2014 entitled "Computer-implemented method for calculating and communicating to a Debtor the anticipated amount for which a creditor wili settle the Debtor's debt and instructions on how to interface with the creditor to settle the debt".

This application further claims priority to, and is a continuation-in-part of U.S. patent application Ser. No. 14/257,493 filed Apr. 21, 2014 entitled "Computer-implemented method for calculating and communicating offers to a Debtor to eliminate a Debtor's debt obligation to a creditor by having a third party entity pay the debt purchase amount to fully assume the Debtor's debt obligation".

This application, and application Ser. Nos. 14/257,499 and 14/257,493 further claim priority to, and are a continuation-part of U.S. patent application Ser. No. 13/528,764, filed Jun. 20, 2012 which has matured into U.S. Pat. No. 8,706,616 on Apr. 22, 2014 entitled "SYSTEM ANTI METHOD TO PROFIT BY PURCHASING UNSECURED DEBT AND NEGOTIATING REDUCTION IN AMOUNT DUE"

This patent application, and each of the above-listed U.S. patents and patent applications further claim priority to U.S. Provisional Patent Application Ser. No. 61/498,835 filed on Jun. 20, 2011.

COPYRIGHT NOTICE AND AUTHORIZATION

Portions of the documentation in this patent document contain materials that are subject to copyright protection. The copyright owner has no objection to the facsimile reproduction by anyone of the patent document or the patent disclosure as it appears in the Patent and Trademark Office file or records, but otherwise reserves all copyrights whatsoever.

BACKGROUND OF THE INVENTION

When patient accounts are not paid, providers take action (negative actions) against the patients including demand letters, sending the account to a collection company, effecting the patients' credit rating and suing the patient, and/or guarantor, for payment. Of course, different providers take different actions and at different time periods. Some providers will sue patients at one year, other providers will sue a patient at 2 years; some providers will not sue patients. Further, various methods to collect payment (the "negative actions") are used differently by providers based on variables like the age of the bill and the amount of the bill.

The present disclosure is software, system and process that will forecast the negative actions taken by a specific provider, based on specific variables associated with the medical bill. This information may be used by a Seller or entity using the PODS system to decide how and when to settle the medical bill with the provider. Further, the disclosure will forecast the provider's anticipated settlement amount based on specific variables.

Among the technical innovations and the advancements to the art disclosed in this invention is the fact that this implementation must be computerized as many payers are forcing members to receive EOBs electronically as they are stopping paper communications. Because of that, the PODS system could not be attempted by humans. Furthering this point, when the PODS system is used by a payer, it is being processed in the computer environment of a payer's claims and EOB system.

Another technical advancement is the immediate decision by the PODS system (within seconds) to purchase, or not purchase, the medical debt.

The PODS system cannot be implemented via humans because, amongst other reasons, there would be a delay in working files and there would be rejections with payer appeals and grievances, and with negative actions taken by providers.

This invention and implementation, complete with error checking algorithms, is a technical advancement as it eliminates human error, bias and potential manipulation. Such errs, bias and manipulations can cause economic harm in purchasing debt. Such problems are averted by the PODS implementation of the invention.

Prior to this disclosure, Sellers could not rid themselves of a provider's debt liability by paying a third party. The best a Seller/patient could do was to hire a patient advocate, medical claims advocate, lawyer or debt settlement company to negotiate a settlement for them. This advancement allows Sellers to avoid negative actions that occur when working with a claims advocate, lawyer, debt settlement company while still benefiting from a reduced debt liability.

Prior to this disclosure, Sellers had no way to know that exact Settlement Price for their medical bill as a claims advocate, lawyer or debt settlement company could only negotiate the settlement and the Settlement Price was given after the work was completed. This disclosure allows for a Seller/patient to know the exact price for which the Seller/patient will settle the debt (Settlement Price) from the onset of the engagement which solves a technical problem and is advancement in the art of settling medical debt at a reduced price.

An advancement in the art, and the technology thereof, is profiting from buying unsecured debt liability for less than the billed charges (a/k/a debt owed) by applying technology.

A technical advancement in the art is using the PODS system as a debt collection company. Never before has this been done. Debt collection companies work by threats; the PODS system when used in the debt collection industry offer a different approach to collecting on medical debt.

Prior to this disclosure, a Seller or other entity could only guess when the next negative action a provider would occur and what the negative action would be. This disclosure forecasts when a negative action will occur and what the action will be based on specific data variables and predictive analytics.

Prior to this disclosure, a medical claims advocate, debt settlement company or other could only provide a general estimated reduction based on an averaging of reductions; specificity was lacking. The POD system may provide very accurate data on the Settlement Price based on the name of the provider, age of the bill and amount owed. This is a technical improvement because while a provider may offer a 60% reduction on a $20,000 debt, a provider likely will not do the same for a $100 debt. Forecasting a Settlement Price with accuracy is a technological advancement.

The collecting, selection and arrangement of data elements in the databases [FIG. 2 element 126, FIG. 2 element 120] used by the PODS system are unique and a technological advancement in the field.

Prior to this disclosure, settling medical bills at a reduced price was a manual process. Because the entire process is automated, as disclosed herein, there is a significant technical advancement.

An advancement in the art goes to the fact that some providers will not work with third-party companies like claims advocates or debt settlement companies. Because the PODS system purchases the liability, the provider must work with an entity other than the Seller/patient.

SUMMARY OF THE INVENTION

1. Summary of a First Preferred Embodiment

Software, system and process ("PODS") are disclosed that allows a debtor and entity using the system to financially benefit. The system includes estimating the reduced-price the debtor is willing to pay to offload the total debt liability (Selling Price); estimating the creditor's price to settle the debt and the resistance the creditor will give in settling the debt. Based in the PODS' system ability to accept liability for a debt at a lower price than is owed, the debtor financially benefits. Then by exploiting inaccuracies, errors, up-coding, over charging, over treating and other issues that cause inflated medical bills, the PODS entity is able to settle the outstanding balance with the creditor (i.e., provider) for a fee lower that that paid by the debtor, resulting in a profit to the PODS entity.

The PODS system may be fully automated with the software where the Selling Price is calculated and offered, then if accepted by the Seller, the PODS system determines a payment amount to send the provider/creditor and automatically sends a legal agreement transferring debt liability to the PODS entity then automatically sends payment and settlement terms to the provider/creditor. An alternative embodiment is to flag specific medical bills for review by an expert (i.e. medical doctor looking at a medical error or medical necessity) based on error checking algorithms that are run over the data.

Patient advocacy companies or patient billing companies (often referred to as advocates in the health care industry) work to lower the patient's responsibility (i.e., the cost) of medical bills on a contingency fee, for a percentage of the savings, or flat fee basis. The present invention recognizes that if the medical debt is purchased the revenue margins increase dramatically. First, there is profit made due to auditing charges and obtaining a lower outstanding amount. Second, the advocacy company also may seek reimbursement from the insurance company(s) allowing a 2× (two fold) return on the investment when compared to strictly working the claim on a contingency fee basis. For example:

Mary has a $40,000 bill from a medical procedure that was denied by the insurance company. An advocacy company that fought the insurance company for reimbursement and won full reimbursement ($40K) would be paid 30% of the savings equaling, $12,000. If an entity using the system of the invention purchased the debt liability at a reduced cost (reduced cost to debtor) for $25,000, and fought the insurance company for the full $40,000 and won, and settled the bill with the provider for $20,000, the profit would be $45,000. Additional value to the patient/debtor is that once they novated liability to the PODS entity, they had no more financial exposure, potential bad credit ratings, pending lawsuits or other.

The present invention is different than the flat fee or contingency fee methods described above in that the person who owes the debt (herein "Debtor") is paying the person or entity implementing the purchase of debt system of the invention (herein "PODS" and also referred to herein as a "third party entity") a reduced fee to accept novation/transfer of the total liability, or to be the primary guarantor of the debt owed, or act as the step-in entity for the Debtor. The transferred entity, guarantor, or the step-in entity then applies the PODS system to obtain money from the payer and to reduce the debt liability to an amount that is lower than the amount the PODS entity received from Debtor (Selling Price). The result is a financial gain for both the Debtor and the PODS entity. Moreover, since the transferee, guarantor, or the step-in entity (PODS entity) owns the debt, this approach overcomes a provider's policies of not working with a third party to negotiate resolution of a debt. PODS (third party entity) is now the Debtor or creditor.

In an exemplary embodiment, the invention includes computer implemented process, mathematical models and algorithms, computer systems, and computer readable storage media including instructions that when processed by a processor enable the processor to implement methods for an entity using the PODS system to realize a financial gain by purchasing debt at specific price and/or obtaining insurance reimbursement and/or obtaining a lower settlement amount with the creditor. This embodiment may be completely automated requiring minimal human interaction for the purposes of error correction, data validation, transformative document processing, electronic computer-to-computer communications, and similar validating purposes. En an alternative embodiment, this process may be partially automated but human interaction required for the purposes of error correction, data validation, human investigation for medical errors when indicted by the computer system, human investigation for billing errors when indicated by the computer system, human negotiating with a Seller for a final price for which to accept the debt, human interacting with a provider if the automated process fails to achieve a settlement with the provider/creditor, and similar situations:

In exemplary embodiments, such method includes the steps of:

the Seller accesses the software via the Internet or PODS network by having the Seller's computer electronically establish a communication between the Seller's computer and the PODS system;

the Seller enters information into software via a novel application programming interface;

the novel application programming interface is linked the a keyboard, or computerized surface (touch-screen like an IPad® screen) that acts like a keyboard and the Seller physically presses keys or buttons that populates the data fields in the application programming interface;

the Seller uploads a scanned image of the medical bill and insurance statement (EOB) to the PODS computer system via a computer-to-computer electronic communications protocol;

the PODS computer system stores the entered information in a physical binary structure that is stored on a computer readable storage medium (a PODS database);

the PODS computer system then scans the medical bill and EOB and populates the PODS database with this data;

the PODS computer system executes queries that search for billing errors or medical errors that may result in reducing the medical debt.

the PODS computer system executes queries that contain mathematical models and algorithms that are run over the data stored in the PODS database and potential Settlement Prices and purchase prices (a/k/a Selling Price) are produced;

the PODS entity makes an offer to the Seller and the Seller then accepts or declines the offer via the application programming interface by physically clicking a mouse button or physically pushing a button on a touch-screen (i.e. Wad screen) indicating acceptance or decline;

the PODS entity works the new case if it is accepted;

the PODS entity determines the method to settle the outstanding balance with the provider;

and the PODS entity determines a final price to pay the provider and send an automated settlement letter and payment.

In the exemplary embodiment, execution of the mathematical models and algorithms includes executing computer code that processes historical data of past settlements, error checking algorithms, and calculations based on individual elements of the medical bill in order to predict the provider's Settlement Price. This query returns a few different results (each based on a different mathematical model) so that the PODS computer system may evaluate the predicted Settlement Price in different ways. Execution of the mathematical models and algorithms also includes executing computer code that processes the data inputted by the Seller to predict the provider's Settlement Price without the use of historic data. This other method is strictly a mathematical model based in the Seller's inputted data. Based on the processing of the computer algorithms, a mathematical model and result is determined. The mathematical result is compared to pre-determined criteria to determine if the PODS computer system desires to purchase the debt liability based on pre-established criteria.

The PODS computer system returns a result to the Seller stating whether or not the user of the PODS computer system wants to purchase the debt or not. If the user of the PODS computer system does not want to make an offer to purchase the debt, it will state this on the computer display screen and the process ends. However, if the user of the PODS computer system does want to make an offer to purchase the debt, an appropriate indication will be displayed on the computer display screen. The Seller may then choose to accept or decline the offer. If the Seller declines the offer, then that is the end of the process. If the Seller chooses to accept the offer, then the PODS computer system Will query the physical PODS database for the legal language and then create a transformative document inputting the Seller's information, the medical bill information, and the Selling Price that was determined by the mathematical models. The transformative document will be displayed via a computer display and the Seller must decide whether he/she wants to decline or accept the offer to purchase the debt made by the PODS computer system. If the Seller declines the offer (as offered via the transformative documents containing legal language), then that is the end of the process. If the Seller does accept the offer made by the PODS computer system, then the PODS computer system will display payment information. This will be a software display where the Seller may enter his/her credit card or electronic checking information.

After payment is made by the Seller, the PODS computer system will create a transformative letter that will be sent electronically (or via US mail) to the creditor or Seller stating that the user of the PODS computer system has assumed the liability for the debt. If the Seller's credit rating was affected by the outstanding medical bill [FIG. 20 item 2000], then the PODS computer system will generate a transformative letter by inputting transformative data specific to the Seller's information and medical bill details, and legal language, then email (or send via US mail) this letter to the Seller, or to the credit bureau (i.e., TransUnion, Equifax, Experian) [FIG. 6A, FIG. 7A, FIG. 8]. The user of the PODS computer system will utilize i) use the automated process described in this disclosure or ii) in an alternative embodiment, when and if possible, use his/her skill to seek reimbursement from a payer, negotiate with the creditor to accept a lower offer, obtain a grant or charity care to help lower or pay the medical bill, audit the medical bill for errors, identify another payer (i.e., malpractice carrier, homeowners), and/or find other ways to lower the debt. The results of the Seller's payment price and demographic details are entered into the PODS database. The results of the settlement of the medical debt are entered into the PODS database and the process is then complete.

2. Summary of a Second Preferred Embodiment

This embodiment relates to software, system and process for healthcare claims payers, or companies that provide explanation of benefits statements to end users, to create a new revenue stream based on their current operating model.

Healthcare claims payers issue explanation of benefits statements (EOBs) to their covered members and this reporting requirement is a fixed cost. Further, payers pay companies like MultiPlan® and GlobalClaim Service to negotiate out-of-network claims to control both the payer's and member's costs for services rendered by a provider. These negotiating services are an additional cost. The present invention is able to convert these cost centers into a profit center by using the payer's reporting process as a communications platform to purchase the member's responsibility portion of the bill and profit from it by settling the outstanding amount due at a lower price. Additionally, the implementation of purchasing the debt liability then profiting on it may replace the fees paid to companies like MultiPlan and GlobalClaim Service thereby saving money.

In its simplest form, when the payer notifies the patient/member of the patient responsibility portion of the medical bill, the payer will also notify the patient that the patient may pay the payer, or entity using the payer's system to communicate the offer, which is a discounted fee in exchange for assuming the liability for the outstanding medical bill. By doing this, the payer does not incur any significant costs as it uses its current correspondence processes as a communications means. Further, this invention allows the payer an opportunity to profit by i) accepting the debt liability from the patient/member, then settling the outstanding debt for a lesser amount accepted from the patient/member. ii) By converting cost centers like MultiPlan's services into profit centers. iii) Because the current invention lay outside the minimum Medical Loss Ratio regulations, it allows for an unregulated profit channel.

Healthcare payers have identifiable problems. One problem is that the natural progression of a company states that at some point, the company stops growing in terms of revenue and must find additional sources of revenue. Failure to identify new sources of revenue means the company can no longer continue to grow unless it decides to acquire other companies.

The second problem payers face is the medical loss ratio (MLR) implemented under the Affordable Care Act. This government describes the MLR as:

"A basic financial measurement used in the Affordable Care Act to encourage health plans to provide value to enrollees. If an insurer uses 80 cents out of every premium dollar to pay its customers' medical claims and activities that improve the quality of care, the company has a medical loss ratio of 80%. A medical loss ratio of 80% indicates that the insurer is using the remaining 20 cents of each premium dollar to pay overhead expenses, such as marketing, profits, salaries, administrative costs, and agent commissions. The Affordable Care Act sets minimum medical loss ratios for different markets, as do some state laws."

The problem is that the implementation of the MLR chokes profits. The present disclosure is software, system and method to allow healthcare claims payers to implement a new invention that allows the payer to profit off the "patient responsibility portion" of a claim and to do so with minimal changes to the healthcare payer's operating processes and methods. Further, the healthcare payer will also benefit from increased member and provider satisfaction.

The third problem is that patients go out-of-network and payers pay third party companies like MultiPlan and GlobalClaim Services to negotiate down the out-of-network claims. The problem is that payers must pay these third party payers and the current invention allows payers to turn this operating cost into a profit center.

The member satisfaction comes from the member's being able to pay their "patient responsibility portion" of the bill at a lower price. The provider satisfaction comes from an increase on collecting receivables that would have otherwise gone unpaid. This last statement is based on the fact that providers are often never paid the patient responsibility portion of the bill by the patient and so, this current invention helps to obtain a partial payment for the provider when many of the outstanding invoices would have otherwise gone unpaid.

Healthcare payers have not monetized their reporting obligations; specifically the explanation of benefits statements, denial letters, appeals responses, etc. The current disclosure allows a healthcare payer to utilize their correspondence as part of an advertisement to purchase the patient responsibility portion of a debt and profit from that by settling the debt for less than is owed.

In addition to the above, healthcare payers are burdened with two things. First, their members become angry when they go out-of-network, or receive a coverage denial, and incur a large balance bill from the provider (balance bills also come in the way of denied care and elective care). Second, when members do go out-of-network, healthcare payers engage and pay companies like MultiPlan and GlobalClaim Service to negotiate a reduced rate for the out-of-network care. These payments to MultiPlan and GlobalClaim Service are a cost center.

The current disclosure allows the payer to profit by purchasing the patient responsibility portion of the bill at a reduced rate to the patient/member, then settle the outstanding amount due to the provider for a lesser amount than paid by the patient/member thereby realizing a profit.

All products and services are plagued with advertising costs and that cost center is generally a significant expenditure. The current invention makes use of the payer's current reporting system—via an EOB—as its advertising means and because this is already a fixed cost, there is little to no need for additional advertising dollars. Further, because payers generally have a significant number of members, United Healthcare reported 70 million members in 2013, there are a significant number of opportunities to convert a prospect into a client.

FIG. 26A and FIG. 26B contains exemplary financial projections if Aetna® insurance company was to implement the current disclosure. This illustrates an advancement in the art.

3. Summary of a Third Preferred Embodiment

Collection companies have existed for a long period of time. There are three basic types of collection companies. They are, the in-house collection companies; outside collection companies and the law firms that act as collection companies. This embodiment is to assist as an alterative collection method.

The basic premise of different types of collection companies is to scare and pressure debtors into paying their debts. In order to achieve this, collections companies will threaten lawsuits, wage garnishment, affect the patient's credit rating, make payment arrangements, and/or try other tactics in order to obtain payment on the outstanding amounts due.

Collections companies face a few problems in operating their companies. First, they are subject to regulations. Second, they are subject to federal and state laws. Third, they must strike a delicate balance for their clients. Often, clients want the collection companies to pursue monies but in a kind way because the creditor company wants to keep the debtor as a returning customer. To that end, the collections company must be aggressive and forceful, yet refrain from scaring the customer away to the point where the customer ceases to use the creditor's products/services.

This embodiment implements an effective collections campaign that meets regulatory requirements, allows for the collections of monies due, yet is not threatening to the end user/customer. In short, it may be considered "soft collections."

Creditors use collections companies to obtain outstanding monies from debtors. The problem is that creditors want these debtors to continue to use the creditors' products/services and collections companies often scare debtors. The current disclosure allows for the collection from debtors in a "friendly" manner by purchasing the debt from the debtor at a reduced price. Further this implementation may be implemented in tandem with traditional collections companies to increase the number of debtors from whom money was collected and/or the total amount collected from debtors.

The invention consists of an entity purchasing the debt owed by the debtor then settling the debt with the creditor for an amount less than paid by the debtor. Further, for greater effect, this "soft collections" approach may be used in conjunction with the efforts of a standard outside collections company or a law firm that acts as a collections company. What this does is to have the actions of the traditional collection company drive debtors to utilize the offer from an entity employing this invention (PODS entity) as the PODS entity offers both relief and an alternative to the standard "hard collections practice."

An additional benefit to the PODS entity is customer satisfaction. Often creditors need to utilize collections companies based on legal requirements, company policies and common business practices. But these same creditors know that sending a collections company after their customer to recover debts owed, will dissuade a customer from using the creditor again.

EXAMPLE

A patient owes a provider $2,000 for an operation. The provider employs a collections company that sends threatening letters, makes phones calls and, in the mind of the patient (i.e., the debtor) harasses the patient.

In such cases, patients will often not utilize the services of this provider again because i) they fear the provider will give lesser care. ii) they fear the provider will not treat the patient. iii) the patient is fearful of the interaction with the provider for fear of embarrassment, asking for payment or other.

If a creditor employs a company implementing the PODS system, the creditor has a greater chance of obtaining payment from the debtor while maintaining a good relationship with the debtor.

In an alternative embodiment, the creditor may send their debtors to a collections company to begin "hard" collections activities. Once hard collection activities have begun the creditor may employ a company utilizing the PODS system when it deems maximum effect will be obtained. By having the PODS entity implement its offer to buy the debt at a reduced price at the same time "hard" collections activities are occurring, the creditor can maximize its financial recovery.

4. Summary of a Fourth Preferred Embodiment

A system, process and software is provided to novate or otherwise transfer the patient responsibility portion of a medical bill to a third-party for a reduced price, in a healthcare environment. The purpose of the transfer of the debt liability is that a professional third-party will have the resources to audit the medical bill for billing errors, overbilling, overtreating, medical errors, fraud, medical necessity, and more, allowing the third-party the opportunity to profit from accepting the debt liability for a lesser amount than is owed. The patient/Debtor benefits from the transfer by paying a lesser amount while being protected from adverse negative events like a bad credit rating.

The complexities involved and issues to be traversed include transferring debt liability in a manner that offers the greatest monetary gain to the PODS Entity (novation vs. guarantor vs. step-in entity); transferring the debt in a manner that avoids the legal tort of tortious interference; transferring the debt without the provider/creditor having to proactively, while consuming provider resources, acknowledge the transfer in order for the transfer to be binding; and other associated issues. These problems are overcome by the system, method and process described herein.

This premise of this embodiment, namely, transferring the debt liability in exchange for a reduced fee, is supported by the federal government which states that a shortcoming of the Affordable Care Act was the lack of cost control forcing patients into bankruptcy even though they have health insurance. This embodiment assists patients in paying their bills but also assists in avoiding financial ruin due to overbilling, billing errors, up-coding and other issues as described herein.

5. Summary of a Fifth Preferred Embodiment

This embodiment relates to software, system and process that forecasts the negative actions that will be taken by a provider to collect a debt owed. The negative actions include, but are not limited to, calls from collection companies, letters from collection companies, effecting the debtor's credit rating, lawsuits, not treating the patient and a provider's internal efforts at contacting the patient/guarantor. The negative consequences are based on a specific provider, the age of the medical bill and the age of the medical bill.

The steps taken include

In exemplary embodiments, such method includes the steps of:
the PODS entity accesses the software via the Internet or PODS network via a computer-to-computer electronic communications protocol;
the PODS entity enters information into software via a novel application programming interface;
the programming interface is linked the a keyboard, or computerized surface (touch-screen like an IPad® screen) that acts like a keyboard and the PODS entity physically presses keys or buttons that populates the data fields in the application programming interface;
the computer system runs algorithms [FIG. 2 element 130] over the databases(s) storing historical collections data [FIG. 19A, FIG. 1913, FIG. 19C, FIG. 2 element 126].
the result of the algorithms are a report on what negative actions will be taken by the provider and approximately when the negative action will be taken by the provider [FIG. 9B]. Additionally, the system will anticipate how difficult it will be to settle a debt (resistance rating) with a provider. This information is identified by the "Resistance Ratings" displayed in FIG. 9C.
additional data on providers is updated in the database as medical bill settlements occur.

BRIEF DESCRIPTION OF THE DRAWINGS

FIG. 1A-1 through FIG. 1A-7 is a sample computer display where a Debtor would input their contact information, answer relevant questions, and upload a scanned image of the invoice or information on the outstanding debt.

FIG. 1B-1 through FIG. 1B-7 is a sample computer display like in FIG. 1A-1 through 1A-7 except that it allows the Debtor to include an estimated payment by a payer. This is used if Debtor/Seller wants to sell the medical bill prior to payments being made by the payer (i.e., at the time of service).

FIG. 2 is a system level diagram illustrating how the PODS computing environment is implemented.

FIG. 3-1 through FIG. 3-6 is a sample computer display that illustrates a sample end user agreement, utilizing novation in the process that has been transformed based on the information entered, mathematical modeling and computer implement processing.

FIG. 4-1 through FIG. 4-6 is a sample computer display that illustrates a sample end user agreement, utilizing a guarantor (i.e., surety) in the process that has been transformed based on the information entered, mathematical modeling and computer implement processing.

FIG. 5-1 through FIG. 5-6 is a sample computer display that illustrates a sample end user agreement, utilizing a step-in entity in the process that has been transformed based on the information entered, mathematical modeling and computer implement processing.

FIG. 6A is a sample financial responsibility letter, transformed based on the inputted data in FIG. 1A-1 through FIG. 1A-7 or FIG. 1B-1 through FIG. 1B-7, sent to the Debtor via electronic means for use to repair credit history and for presentation to the creditor or the creditor's agent(s). This process is used when the debt is accepted by the PODS entity via novation.

FIG. 6B and FIG. 6C are sample financial responsibility letters, transformed based on the inputted data in FIG. 1A-1 through FIG. 1A-7 or FIG. 1B-1 through FIG. 1B-7, sent to the creditor or the creditor's agent(s). This process is used when the debt is accepted by the PODS entity via novation.

FIG. 6D and FIG. 6E are sample financial responsibility letters, transformed based on the inputted data in FIG. 1A-1 through FIG. 1A-7 or FIG. 1B-1 through FIG. 1B-7, sent to the creditor or the creditor's agent(s). This process is used when the debt is accepted by the PODS entity, via novation, when the payer implementation is being used/implemented.

FIG. 7A is a sample financial responsibility letters, transformed based on the inputted data in FIG. 1A-1 through FIG. 1A-7 or FIG. 1B-1 through FIG. 1B-7, sent to the Debtor via electronic means for use to repair credit history and for presentation to the creditor or the creditor's agent(s). This process is used when the PODS entity is acting as the guarantor of the debt.

FIG. 7B and FIG. 7C are sample financial responsibility letters, transformed based on the inputted data in FIG. 1A-1 through FIG. 1A-7 or FIG. 1B-1 through FIG. 1B-7, sent to the creditor or the creditor's agent(s). This process is used when the PODS entity is acting as the guarantor of the debt.

FIG. 7D and FIG. 7E are sample financial responsibility letters, transformed based on the inputted data in FIG. 1A-1 through FIG. 1A-7 or FIG. 1B-1 through FIG. 1B-7, sent to the creditor or the creditor's agent(s). This process is used when the debt is accepted by the PODS entity, as the guarantor, when the payer implementation is being used/implemented.

FIG. 8 is a sample financial responsibility letter, transformed based on the inputted data in FIG. 1A-1 through FIG. 1A-7 or FIG. 1B-1 through FIG. 1B-7, sent to the Debtor via electronic means for use to repair credit history and for presentation to the creditor or the creditor's agent(s). This process is used when the PODS entity has utilized the "step-in" agreement and process.

FIG. 9A is a sample report of the estimated settlement amount.

FIG. 9B is an exemplary detailed report of estimated negative consequences based on the Total ERA Collection Experience.

FIG. 9C is an exemplary report made under a service bureau implementation.

FIG. 10 is a sample computer display indicating that the Debtor must repair his/her own credit and that the financial responsibility letter will be forthcoming.

FIG. 11 is a sample form that an insurance company using PODS would send to a Debtor to transfer the debt.

FIG. 12 is a sample provider policy on providing negotiated discounts for patients whose insurance company does not contract with the provider.

FIGS. 13A-13C, taken together, constitute a flowchart illustrating how the PODS process is used by a Debtor.

FIGS. 14A-14C, taken together, constitute a flowchart on how the PODS computer system is incorporated and used by a payer (i.e., health insurance company, Medicare, a TPA).

FIG. 15 is a sample computerized display of an offer made to a Seller for the Seller to accept or decline the offer.

FIG. 16 is a sample computerized display of a report made to the PODS entity telling the best date to begin interactions with the provider and who, at the provider's office, to contact for the best result.

FIGS. 19A-19C, taken together, is a sample computer database structure. It is composed of a physical binary structure stored on computer readable medium.

FIG. 20 is an exemplary letter used by collection companies to scare debtors into paying their debts and stating that the person's credit rating had been affected.

FIG. 21 is an exemplary letter from an entity using the PODS system to purchase the outstanding debt.

FIG. 23A and FIG. 23B, taken together, create an exemplary charity care guideline.

FIG. 24 is an agreement from Multiplan to negotiate the out-of-network cost for a patient on behalf of CIGNA®.

FIG. 25 is an agreement from GlobalClaim Services negotiate the out-of-network care for a patient on behalf of Aetna®.

FIG. 26A, FIG. 26B and FIG. 26C, taken together, create an exemplary high-level financial projections based on Aetna implementing the current invention.

FIG. 27 is a standard explanation of benefits from a payer.

FIG. 28 is an exemplary explanation of benefits statement that incorporates an offer to buy the Debt.

FIG. 29 is a flowchart illustrating how the PODS process is implemented as a service bureau.

FIG. 30 is an exemplary diagram on how to implement the transferring of the debt obligation.

FIG. FIG. 32A and FIG. 32B are exemplary computerized user interfaces for the Seller to enter data to determine a Selling Price.

FIG. 33 is an exemplary Selling Price emailed to the Seller, by the PODS entity, based on the data physically entered by the Seller in FIG. 32A and FIG. 32B and calculated by the source code in the accompanying Appendix C.

DETAILED DESCRIPTION OF THE INVENTION

Figure 2:
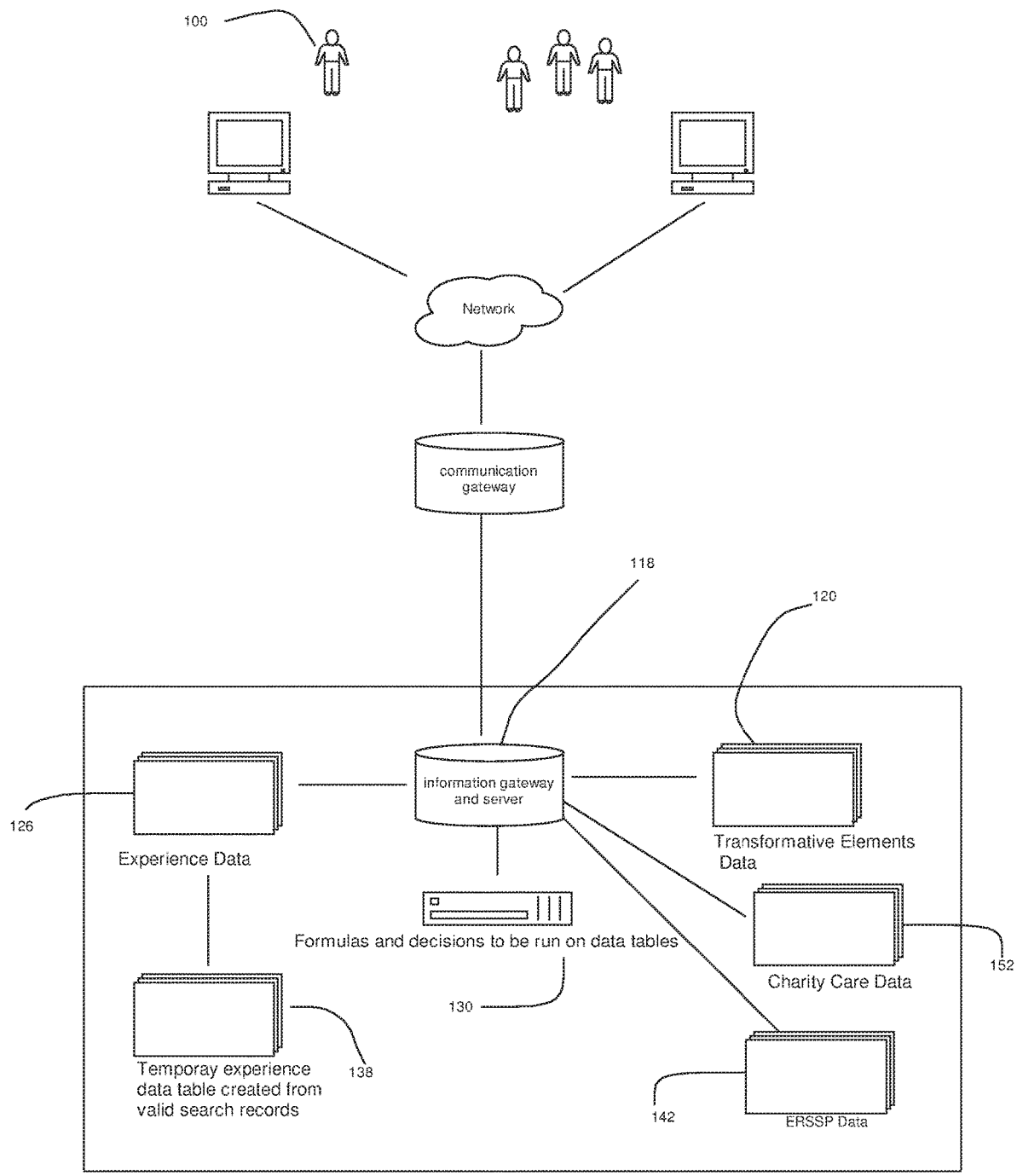

This disclosure includes an Appendix A, Appendix B, Appendix C and Appendix D. The Appendix A, Appendix B, Appendix C and Appendix D are incorporated by reference into the present patent application. One preferred embodiment of the present invention is implemented via the source code in Appendix C and Appendix D. Appendix A, Appendix B, Appendix C and Appendix D are subject to the "Copyright Notice and Authorization" stated above.

A detailed description of illustrative embodiments of the present invention will now be described with reference to FIGS. 1A-1 through FIG. 33. Although this description provides a detailed example of possible implementations of the present invention, it should be noted that these details are intended to be exemplary and in no way delimit the scope of the invention.

Definitions

When used herein, the following terms will have the following meanings unless indicated otherwise:

A "provider" is a doctor, nurse, therapist, dentist, hospital, health clinic or any other person/entity that provides healthcare. For the purpose of this disclosure, the provider is also the creditor.

A "Debtor" is the person who owes the unsecured debt.

A "PODS entity" is the person or entity implementing the Purchase of Debt System ("PODS") described herein.

A "Seller" is the person selling the medical debt to the PODS entity.

The "Selling Price" is the price the Debtor is willing to pay the PODS entity to accept responsibility for the debt owed. "Selling Price" is also a computer variable when used in calculations, software and database structures.

The "Settlement Price" refers to the estimated or actual price the provider/creditor is willing to accept to settle the debt. "Settlement Price" is also a computer variable.

"EOB" an industry term for a payer's explanation of benefits statement [FIG. 27]. The EOB may be paper or electronic.

A "payer" is an insurance company, third party administrator ("TPA"), Medicare, Medicaid, a plan fiduciary or entity that is responsible for processing and paying healthcare claims.

The "outstanding balance," "debt," "amount due," and "amount owed" are used interchangeably to refer to the "patient responsibility" portion of the medical bill.

A "member" is a member person who is covered by the payer's entity. Example: people enrolled with Aetna are called plan members.

"date of service" is an industry term describing when the episode of care took place. The acronym DOS is often used for this.

"negative consequence(s)" refers to actions taken by providers in collecting a debt owed by a patient. Such action include, but are not limited to, calls from collection companies, letters from collections companies, lawsuits, negative credit rating marks, and not treating the patient. "Negative consequences" and "negative actions" are synonymous and used interchangeably.

"selling," 'sell,' "selling the bill" or "sell the debt" means transferring the debt liability in exchange for payment by the Seller.

"purchase debt," "purchase bill," "buy the debt" or "buy the bill" and similar phrases means accept liability for the debt via acting as guarantor, novation or acting as a step-in entity in exchange for payment being made to the PODS entity as described in this disclosure.

"HIPAA" is the Health insurance Portability and Accountability Act.

"transferee" is an entity that accepts the debt liability. This acceptance is often through novation, but may also be through acting as the guarantor or step-in entity.

"novated" is the act of transferring the debt via novation.

"CMS" refers to the Centers for Medicare and Medicaid Services.

For the purposes of this disclosure, it will be assumed that the "patient" is also the guarantor.

For the purposes of this disclosure, "transfer" of the debt will include novating the debt to the PODS Entity, the PODS Entity acting as the guarantor of the debt or acting as a step-in entity for the debt liability.

Various calculations throughout this disclosure refer to "AVG" or an average. An average, or averaging, refers to the basic mathematical operation of averaging. That is, a computer will add each result for a dataset and then divide that result by the number of records used in the dataset.

Example for The formula to calculate the average number of days for Savg_days_negative_action is:

Step A: for each record in the data table described in FIG. 19A through FIG. 19C:

Step 1 convert variables DOS and DNCR in each records to their Julian day values.

Step 2 run the following formula (DNCR-DOS). This will result in a specific number for days for each record. Note: DNCR and DOS are each columns in the data table in FIG. 19A through FIG. 19C.

Step B: sum all the results from Step A above

Step C: divide the result in Step B above by the total number of data records used in Step A. This result is the average for Savg_days_negative_action and is an exemplary embodiment on how to calculate the average of something.

Combater Variables:

The following variables will have the following meanings unless indicated otherwise:

"UID" refers to the provider's unique identification number in the data table.

"Provider" refers to the name of the provider and is identified by a unique number in the event there is more than one provider with the same name.

"DOS" refers to the "date of service" for the debt.

"DS" refers to the date the debt was settled.

"BAL" refers to the original outstanding balance of the bill.

"RES" refers to the difficulty or resistance the creditor gave in trying to settle the debt. In this instance, a rating system of 1 to 10 is used but any scale will work.

"STL" refers to the amount for which the creditor settled the debt.

"COL" refers to whether or not the provider used a collection company to call, fax, email or send a dunning notice to the Seller/patient. Note: more than one outside collection company may be used and law firms are often used like collection companies in that they seek repayment of the debt but they do not file lawsuits or take legal action.

"LAW" refers to whether or not legal action was initiated.

"IN" refers to whether or not the provider was in-network with the insurance company.

"HI" refers to whether or not the patient (i.e., Debtor) had insurance at the time the debt was incurred.

"ELEC" refers to whether or not the procedure was an elective procedure.

"DED" refers to whether or not the balance was part of a deductible or co-insurance.

"PC" refers to the major billing code associated with the care provided. The PC codes may be based on CPT codes, HCPCS codes or other system where a coding system is used to describe the care provided.

"CR" refers to the Debtor's credit rating (i.e., TransUnion®, Experian®, Equifax®, FICO® score).

"NCR" refers to a negative credit mark being placed on a patient/guarantor's credit rating as a result of not paying a medical bill.

"DNCR" refers to the date the negative action was taken by the provider or the date the Seller/patient was made award of a negative action via a communication.

"TYPE" means the type of negative action taken by a provider. If "LAW" is placed in this database filed, that means a lawsuit was filed. If "OUTCOL" is placed in this field, it means an out-side collection company was used to contacted the Seller/patient. If "INCOL" is placed in this database field, it means an in-side collection company was used to contact the Seller/patient. If "CREDIT" is placed in this database field, it means the person's credit rating was affected. If "NOTREAT" is placed in this database field, it means the provider refuses to continue to treat the Seller/patient.

"M" refers to the name of the person at the facility with whom the debt was negotiated.

"ME" refers to whether or not the debt was related to a medical error.

"F" refers to the date of the provider's fiscal year end (accounting purposes).

"A" refers to whether or not the provider checked the "accept assignment" box on the claims form that was submitted to the payer.

"B" refers to whether or not the Debtor was in bankruptcy proceedings.

"P" refers to whether or not the Debtor was dead.

"PFS" refers to "potential for subrogation."

"PAY" refers to the payer.

"PDAG" refers to a provider discount that has already been applied to the patient's account.

"IAA" refers to the provider's allowed amount for the claim (i.e., how much the provider would allow as payment)

"TBC" refers to the provider's total billed charges (i.e., the total amount billed).

The variables above are related to the Debtor's debt obligation and characteristics of the provider/creditor and payer. Note: In practicing the invention there will be many instances where certain variables (i.e., data) will be missing because the Seller/Debtor was not able to obtain the data or for some other reason. In such cases, the variables with missing data will not be used in the algorithms and calculations; the algorithms and calculations will then be based on the best set of data available.

Variables Used in Algorithms:

"Fixed Cost" is determined by the PODS entity and are the fixed costs associated with working the file. The fixed cost is an operating cost of the PODS entity.

"Average Cost to Work File" is determined by the PODS entity and is the average labor cost associated with working the file. The average cost to work a file is also an operating cost of the PODS entity.

"money to compensate for error margin" means a small amount of money that helps correct for any error margins in calculations. The amount is determined by the PODS entity so that the value may conform with the PODS entity's business practices.

"Risk %" is the amount the PODS entity should set aside to cover legal costs and transactions when lawsuits are filed or other costs are incurred. The Risk % is pooled over all transactions and is determined by the PODS entity based on the historical interactions in the database, there is no fixed amount for all entities.

Note: All Risk % money will be placed in an account that will be referred to as "Risk Pool Account" for the purpose of this disclosure. An entity using the PODS system will likely place a maximum dollar amount on the Risk Pool Account and once the Risk Pool Account reached the maximum value, the Risk % may be lowered or dropped based not on the provider's historical transactions, but on the fact that the Risk Pool Account is has reached a maximum amount as determined by the PODS entity.

FURTHER DEFINITIONS

"software"—a collection of compiled machine-readable code stored in physical memory which is read in order to cause a tangible and physical hardware processor to carry out instructions and produce an tangible output in the form of new data stored or transmitted via network nodes and/or (where "and/or" is inclusive in this disclosure of either or both terms separated thereby) to a newly created physical medium.

"sequence"—an order of steps beginning at successively in time but which can overlap or be separate in time as they are carried out.

"automatically"—as a function of completion and/or partial-completion and/or beginning a previous action.

"processor"—a hardware device which carries out instructions and produces a new output from an input provided "physical memory"—a hardware device with parts which are movable, magnetic, or otherwise physically altered to store data which can be later retrieved "packet switched"—a form of transferring data between two network nodes in packetized form, each packet having a destination header and the pipeline for such data able to handle multiple senders and recipients of data based on the destination header "circuit switched"—a form of transferring data between two network nodes where the entire pipeline is used to transfer data solely between the two network nodes "network nodes"—place where a network connection begins and/or terminates Overview of the Process Step 1—The Debtor/Seller [FIG. 2 item 100] accesses the system and inputs data [FIG. 1A-1 through FIG. 1A-7 or FIG. 1B-1 through FIG. 1B-7] and that data is transmitted over a network to the information server [FIG. 2 element 118]. Data may also be stored in an electronic file and imported/transferred to the information server [FIG. 2 element 118] via computer readable storage medium. At this time the Debtor/Seller will be offered financial protections as described in Section XI, entitled "Financial Protections" below.

Step 2—The information server [FIG. 2 element 118] will then execute computer code [FIG. 2 element 130] to process the data inputted by the Debtor/Seller in accordance with predetermined algorithms and mathematical equations as described in Section IV, entitled "Transformative Analysis of the Data."

Step 3—Offer to buy debt from the Debtor/Seller:
If the Debtor/Seller entered the data and the transaction is via a computer system only, go to Step 3A.
If the Debtor/Seller provided the data and is working with a natural person at the entity using the PODS system, go to Step 3B.

Step 3A—The Post Analysis Reporting per Section V will be executed. The results for the calculated variables will populate the offer to sell the debt and populate the agreement [FIG. 3-1 through FIG. 3-6—alternative embodiments in FIG. 4-1 through FIG. 4-6 and FIG. 5-1 through FIG. 5-6]. The Debtor/Seller will then accept or decline the offer to sell the debt. In an alternative embodiment, the entity using the PODS system ("PODS entity") could request that the provider (i.e., creditor) authorize the transfer of the debt (i.e., novation) from the Debtor/Seller to the PODS entity. Another alternative embodiment is to allow the Debtor/Seller to input the total amount due and a price he/she is willing to pay to transfer the debt liability. Then, the PODS system would do the mathematical modeling and accept or decline the amount offered by the Debtor/Seller.

Step 3B—The Post Analysis Reporting per Section V will be executed. The natural person using the PODS system will be presented with the anticipated settlement amount of the debt [FIG. 9A]. Knowing the anticipated settlement amount, the person using the PODS system may then engage in an offer and acceptance discussion (or communication via IM, email, etc.) and determine a final amount for which the debt will be sold to the PODS entity. The Debtor/Seller will then accept or decline the offer to sell the debt. In an alternative embodiment, the PODS entity could request that the provider (i.e., creditor) authorize the transfer of the debt from Debtor/Seller to the PODS entity. This complies with the legal concept of novation.

Step 4—Acceptance of offer by Debtor/Seller. If the Selling Price is accepted by the Debtor/Seller, the offer and terms of the agreement [FIG. 3-1 through FIG. 3-6, FIG. 4-1 through FIG. 4-6 or FIG. 5-1 through FIG. 5-6] will be presented and the Debtor/Seller may "Accept" or "Decline" the offer [FIG. 15]. If the Debtor/Seller is not present, then the terms of the agreement [FIG. 3-1 through FIG. 3-6, FIG. 4-1 through FIG. 4-6 or FIG. 5-1 through FIG. 5-6] may be sent via US Mail, facsimile, emailed or conveyed over the phone. The Debtor/Seller would then agree to the terms of the agreement [FIG. 3-6 item 128, FIG. 4-6 item 128 or FIG. 5-6 item 128] or decline the offer. If the offer was accepted, then the entity using the PODS system would collect payment via a credit card, check, Paypal, distribution from a Flexible Spending Account (industry acronym "FSA"), distribution from a Healthcare Reimbursement Account (industry acronym "HAS"), or similar payment method and then continue to Step 5. Also, at this time the provider/creditor would be notified that the PODS entity is responsible for the debt. A financial responsibility letter [FIG. 6B, FIG. 6C, FIG. 6D, FIG. 6E, FIG. 7B, FIG. 7C, FIG. 7D or FIG. 7E] would be used for this purpose. If the Debtor/Seller did not accept the offer, the process would terminate at this time. Note: the preferred embodiment is to have the provider/creditor provide authorization for the transfer of novation, guarantor status or step-in status with a signature [FIG. 6C or FIG. 7C] or via email, fax or other. By receiving an acknowledgement from the provider/creditor, the Debtor/patient is protected from all lawsuits, negative credit ratings and negative consequences if novation is used.

Step 5—Working the Debt. Per Section VII, entitled "Working the Debt," the debt will be worked after all insurance(s) have met (paid out or denied) their obligations in an effort to obtain a settlement and all charities and grants have been tried. An alternative embodiment includes accepting payment from the Debtor/Seller prior to the insurance paying. In such an embodiment, the estimated insurance payment [FIG. 1B-4 item 122] would be calculated into the price accepted by the PODS entity in order to accept the liability of the debt.

Step 6—Settling the Outstanding Debt Owed to the provider/Creditor. The PODS entity will use an automated calculation method as described in Section IV. Entitled "Transformative Analysis of the data" to determine the Settlement Price. Payment and a settlement letter (settlement letter is described in Section VIII entitled Methods to Settle the Outstanding Balance Owed to the Provider/Creditor) will then be sent to the provider/creditor. An alternative embodiment is to have the PODS entity will work with the provider to structure a settlement acceptable to the provider and the PODS entity. If this is not successful, a "take it or leave it" approach will be taken with the provider/creditor.

Step 7 Post Settlement Data. Per Section X entitled "Post Settlement Data," all of the variables in the experience data table [FIG. 2 element 126] will be updated after the debt has been settled. This updated information may then be used for new transactions.

Collection of the Debtor's Data

The data needed from the Debtor may be obtained using a paper process or a computer implemented process.

The Paper Process

The Debtor/Seller, or their loved ones on their behalf, who have a debt will be interviewed and the variable fields in FIG. 1A-1 through FIG. 1A-7 or FIG. 1B-1 through FIG. 1B-7 will be filled in with the relevant information. After the data is inputted on paper, the information will be entered into the PODS system where the transformative analysis will be performed on the data resulting in the final price (Selling Price) that the entity utilizing the PODS system would be willing to accept from the Debtor/Seller for the outstanding debt. This final dollar amount will then be filled in on the paper agreement; the bill and EOB will be sent to the PODS entity shortly thereafter.

The Process as Implemented by Computer Software

Software will present data like that illustrated in FIG. 1A-1 through FIG. 1A-7 or FIG. 1B-1 through FIG. 1B-7. The Debtor/Seller will input the data requested, answer the questions asked, and upload an image of the invoice/bill or information on the outstanding debt. The information will be transmitted over a computer network to the PODS system where the transformative analysis will occur. Once the transformative analysis has occurred, software will present an appropriate agreement to the Debtor/Seller via user interface as illustrated in FIG. 3-1 thru FIG. 3-6, FIG. 4-1 thru FIG. 4-6, or FIG. 5-1 thru FIG. 5-6. The agreement will be presented with all of the variable fields FIG. 2 element 120 filled out with post analysis results.

Note: An alternative implementation is the image of the invoice and EOB may be emailed, sent via facsimile or other transmission mechanism, and the PODS entity would attach the image to the data received via FIG. 1A-1 through FIG. 1A-7 or FIG. 1B-1 through FIG. 1B-7.

III. Creation of the Experience Data on a Readable Computer Medium

The experience data table [FIG. 2 element 126] will be stored in a physical binary structure that is stored on a computer readable storage medium. Each time a debt is settled, the experience data table [FIG. 2 element 126] will be populated with the results. This is how the experience data will be created and/or updated. Additionally, experience data may be acquired and merged into the experience data table [FIG. 2 element 126] in a physical binary structure that is stored on the computer readable storage medium from data gathered by other organizations (like a credit reporting bureau, Westlaw or Lexus-Nexus) or is inputted from information gathered from providers' written policies. Note: data gathered from written policies is not as valid is data collected from debtors and others as providers do not always follow their own policies.

IV. Transformative Analysis of the Data

Algorithms created and used by the PODS entity are designed to minimize CPU usage, minimize random access memory needs, and increase the speed of transformative data.

Determining the final price to accept from the Debtor/Seller (Selling Price) for an outstanding debt is comprised of the processes and computer implemented algorithms described in this section.

Figure 31:
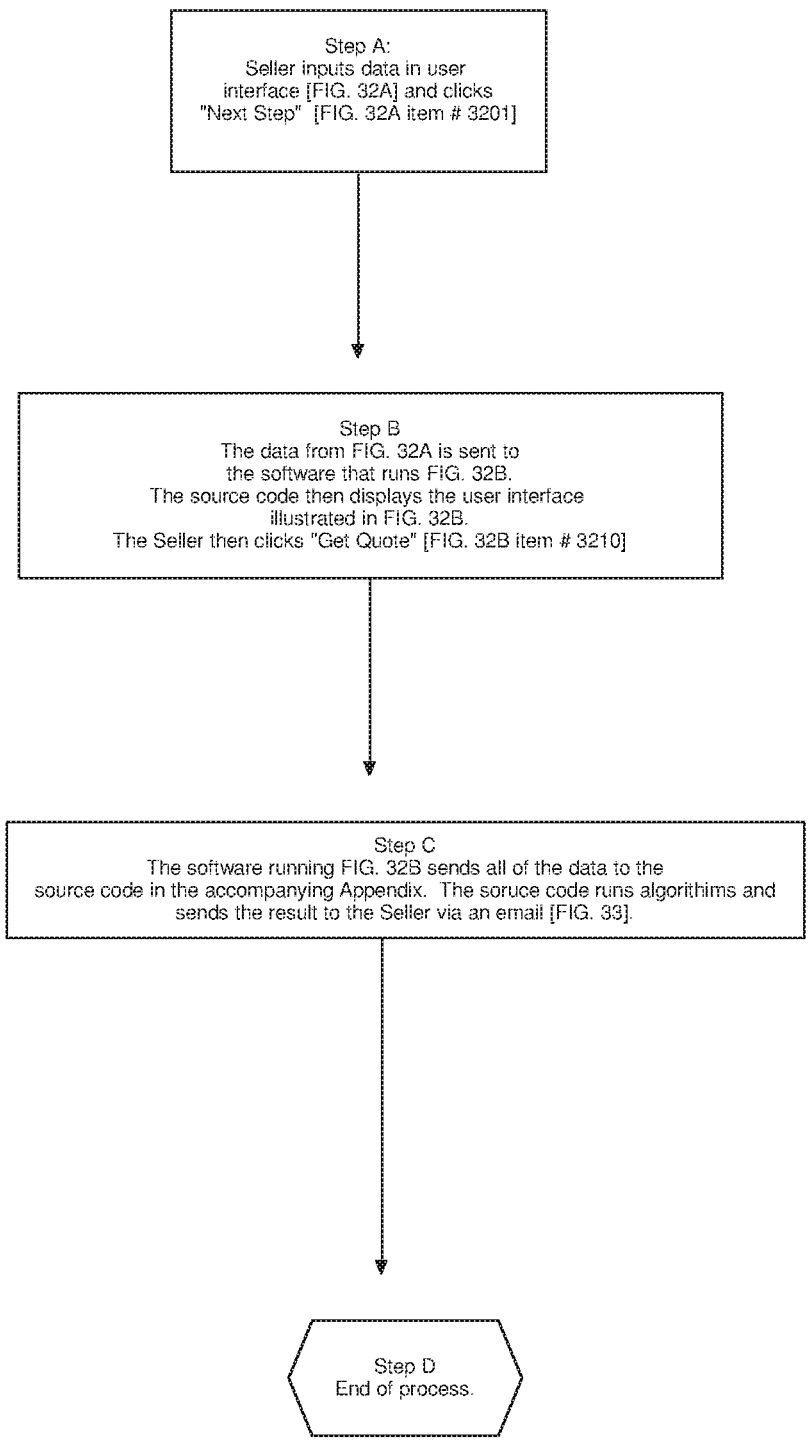
FIG. 31 is an exemplary flowchart for the transfer process.

One embodiment in determining a Selling Price is using the user interface illustrated in FIG. 32A, FIG. 32B and Appendix C. It is comprised of the following steps as outlined in FIG. 31:

FIG. 31—Step A: The Seller physically inputs data, via an input device like a keyboard, into the unique user interface as described in FIG. 32A. The data requested in FIG. 32A is readily identifiable because the user interface asks specific questions.

Once the Seller has inputted the data, the Seller click the link entitled "Next Step" [FIG. 32A item #3201. Upon clicking the link, the data is electronically passed to the software that runs the user interface for FIG. 3213.

FIG. 31—Step B: The software running FIG. 32B is electronically passed the data from the software running FIG. 32A and that data is stored in an array holding the data values. The software then presents the Seller with a user interface to obtain additional data.

The Seller physically inputs data, via an input device like a keyboard, into the unique user interface as described in FIG. 3213. The data requested in FIG. 32B is readily identifiable because the user interface asks specific questions.

Once the Seller has inputted the data, the Seller click the link entitled "Get Quote" [FIG. 32B item #3210. Upon clicking the link, all data that was entered in FIG. 32A and FIG. 32B is electronically passed to the software contained in the accompanying Appendix C.

FIG. 31—Step C: The data from FIG. 32A and FIG. 3213 is then processed by the source code contained in the accompanying Appendix C. The software then processes algorithms, using the data inputted by the Seller, and a Selling Price is emailed to the Seller [FIG. 33]. The Seller would then contact the PODS entity to complete the interaction as described below. An alternative embodiment to this Step C is to click a link located in the email to a pre-populated agreement [FIG. 30 and Appendix D, FIG. 3-1 through FIG. 3-6, FIG. 4-1 through FIG. 4-6 or FIG. 5-1 through FIG. 5-6] and continue with the process as described below in this disclosure. The preceding was a process to obtain data and create a Selling Price based on the inputted data that is transformed, only. Note: Appendix D is software that automates the decision on what type of agreement to use: novation [FIG. 3-1 through FIG. 3-6] vs guarantor [FIG. 4-1 through FIG. 4-6] vs. step-in entity [FIG. 5-1 through FIG. 5-6].

FIG. 31—Step D: This is the end of the process. If the Seller engages the PODS entity, the PODS entity would then begin by executing an agreement [FIG. 3-1 through FIG. 3-6, FIG. 4-1 through FIG. 4-6 or FIG. 5-1 through FIG. 5-6] and then working the debt as described in this disclosure. An alternative embodiment to this Step D is to click a link located in the email to a pre-populated agreement [FIG. 3-1 through FIG. 3-6, FIG. 4-1 through FIG. 4-6 or FIG. 5-1 through FIG. 5-6] and continue with the process as described below in this disclosure.

Alternatively, more complex and precise embodiments follow a process: Once the EOB, UB-04, CMS1500 and/or medical bill are uploaded onto the PODS data system, the materials will be scanned and data fields populated. The data fields include, but are not limited to: location of service, length of stay, CPT codes, Rev Codes, HCPCS codes, diagnosis codes, total charges, insurance adjustments, insurance payments, patient payments, deductible, co-insurance, copayments, non-covered charges, denied charges, etc.

Once the data is populated the PODS entity will run computer algorithms over this data, automating the process for checking for medical errors and billing errors. Each of the calculations, Error Calculation #1, Error Calculation #2 and Error Calculation #3 will be run over the data. If these algorithms indicate an error, the case/file is flagged for review by a human to investigate if a medical error or billing error occurred that may result in a reduction to the outstanding balance of the bill. Please note, that other error checking algorithms may be used in addition to these three:

Error Checking Variables:
 i) $LOS: is the length of stay reported on the medical bill or UB-04
 ii) $Guidelines: is the number of days of care allowed per guidelines like the Milliman® Care Guidelines.
 iii) $flag_this_case_for_error: when this is marked as "true" it means that this case should be reviewed by a person because the length of stay was too long compared to the diagnosis so there may be a billing error or medical error.
 iv) $Patient_reports_error: is a record in a database and when marked as "true" the PODS system will flag the case for the identified error and a person will follow up on the inquiry.

Error Calculation #1—Ask the Patient

The easiest way to determine if a medical error occurred or if there is a charge for a procedure that was not performed is to ask the patient. This may be conducted electronically when the Seller enters the data to sell the medical bill or via a phone call at any point during the interaction.

If the Seller inputted this information or if PODS entity called and made an inquiry, the data field in the PODS' entity's database would be check so that a
 if ($Patient_reports_error="True")
 {
 $flag_this_case_for_error="True":
 }

Error Calculation #2—Length of Stay

A length of stay refers to how long the patient was hospitalized. A simple software algorithm to determine if there is an error is to match the diagnosis code from the ICD-9 or ICD-10 (herein Dx) to the number of days the patient was in the hospital. Examples: a vaginal birth is generally a 48 hour hospitalization; a cesarean birth is generally a 72 hour hospitalization. Therefore, if the patient is hospitalized for more than 72 hours, there is a potential problem that may lead to a reduction in the outstanding bill.

Resources like Milliman® Care Guidelines provide details on the average length of stay. In the software calculation below, the variable Variables:

$LOS: is the length of stay reported on the medical bill or UB-04

$Guidelines: is the number of days of care allowed per guidelines like the Milliman® Care Guidelines for a specific procedure.

$flag_this_case_for_error: means that this case should be reviewed by a person because the length of stay was too long compared to the diagnosis so there may be a billing error or medical error.

if ($LOS>$Guidelines)
{
$flag_this_case_for_error="True";
}

Error Calculation #3—Matching of Dx Codes to Rev Codes and/or CPT Codes

Resources exist that match Dx codes to Rev Codes, HCPCs code and/or CPT codes. Companies like Milliman and QualCare make such resources available. In such a case; if the Rev code, HCPCs code and/or CPT code (procedure codes and durable medical device codes) reported on the medical bill, UB-04, CMS1500 or other, the reported code will be match with the reported Dx code reported. If the Dx code(s) do not match the Rev code(s), HCPCS code(s) and/or CPT code(s) the case will be flagged for a review by a person.

In a simple form, a software array running in random access memory will be made for each Dx code. The array will contain the values of acceptable CPT codes, Rev codes and HCPCS code that are associated with the Dx code. If the reported CPT codes, Rev Codes or HCPC codes are not in the Dx code array, the case will be flagged for review by a human.

```
                my @dx_code_836-2 = valid_CPT
                    Codes("CPT#222", "CPT#444", "CPT#555");
                $Dx_reported = 836-2;
                $CPT_reported = 987;
        my %h = map {$_ = > 1 } @dx_code_836-2;
        my $count = -3;
        my $r = cmpthese($count, {
           'grep' => sub {
            if (scalar grep $$CPT_reported eq $_, @ dx_code_836-2)
            {
                    $flag_this_case_for_error = "False";
            }
            else
            {
                    $flag_this_case_for_error = "True";
            }
           },
        });
```

Based on the input received from the user inputs in FIG. 1A-1 through FIG. 1A-7 or FIG. 1B-1 through FIG. 1B-7, the name and address of the provider [FIG. 1A-1 item 100 or FIG. 1B-1 item 100] is inputted into the system along with the other information and transmitted to the information gateway and server [FIG. 2 element 118]. Data matching is conducted to match the provider information sent, with the unique provider identification (herein "UID") number in the experience database that is stored in a physical binary structure on computer readable memory [FIG. 2 element 126]. The variables may be matched based on the provider's Tax ID number, the provider's name and address, the provider's National Provider Identifier number (their NPI number), or other ways.

Once the UID is identified, computer code is executed and a data analysis (via an algorithm) [FIG. 2 element 130] is performed using and algorithm and mathematical model (described below) on the experience data table [FIG. 2 element 126] and all the experience records for the UID are collected. Based on this information, additional data analysis is performed utilizing the data that was returned and stored in a temporary database structure [FIG. 2 element 138]. First, the data associated with the UID [FIG. 2 element 138] is analyzed for the experience rating on all of the records for a given period of time (e.g., the past three (3) years) along with the number of records in the data table. Second, the data is analyzed based on a specific data set based on the amount of the debt. In this second analysis, the results will be based on the amount of the debt, plus and minus (+/−) a monetary variable given by the entity utilizing the PODS computer system [FIG. 2], along with the number of records in the temporary data table [FIG. 2 element 138].

Example: The debt is $3,000. The monetary variable for the second data analysis is determined to be $500. In this case, the second data analysis will provide results for every experience data table record between $2,500 and $3,500 for that UID.

Calculation Methods to Determine an Estimated Settlement Price:

Third, the data is analyzed using the following analysis/algorithms/mathematical models, all of which are explained below:

i) Total Experience Rating Analysis ("Total ERA") and the Total ERA Risk Ratio;
ii) The Specific ERA and Specific ERA Risk Ratio;
iii) Direct Match Debt Amount Rating Analysis ("DMDRA") analysis and DMDRA Risk Ratio;
iv) The Global Analysis ("GA") and GA Risk Ratio;
v) Total ERA Collection Experience Results
vi) Medicare Allowable Amount Plus Profit
vii) Medicare Allowable Amount vs Cost-to-Charge Ratio
viii) Average PODS Entity Discount Analysis
ix) Average Insurance Payment
x) Leverage Settlement Method
xi) Charity Care Method
xii) Provider Already Discounted Method The point of each calculation method (also referred to herein as a "rating algorithm") below is to calculate an estimated Settlement Price, each method using a different algorithm and/or specification. The calculation results are all possible Settlement Prices and the PODS entity will chose to implement the calculation method (or combination thereof) it deems the best fit for its purposes.

Calculation Method #1—Total Experience Rating Analysis:

The basic premise of this calculation method is to identify an acceptable Settlement Price based on an experience rating. This experience rating is the average historical reduction given by a specific provider.

Based on the data inputted in FIG. 1A-1 through FIG. 1A-7 or FIG. 1B-1 through FIG. 1B-7, the data variables described above will be used to develop the Total Experience Rating Analysis (herein "Total ERA"). Table #1 [FIG. 19A through FIG. 19C], which is stored in a physical binary structure on computer readable storage medium (a computer database), contains data elements and records over which the first software data algorithm(s) [PG. 2 element 130] is executed. The first software data algorithm extracts all records for the specific provider, via UID (variable "UID" in the data table below) from the experience data table [FIG. 2 element 126]. The results of the data analysis by the algorithm are then written to a new, temporary, table [FIG. 2 element 138] that is stored on a computer readable storage medium.

The second software data algorithm is then run over the new, temporary, data table [FIG. 2 element 138]. The data analysis by this algorithm provides two results. Procedure #1,which will be herein referred to as "Total ERA" [FIG. 9A item 922], is an experience rating based on the results of every data record in the new, temporary, table [FIG. 2 element 138]. Specifically, for each record in the new table, the following mathematical model embodied in computer code will be run over the record and the result stored in computer memory:

Total $ERA\ RES$=(Sum of all $RES$ records based on criteria)/(number of records)

Procedure #1—Result for each specific record

Procedure #1 Result=$(STL/BAL)*100$

Procedure 2—Compute the average for each record

Total $ERA$=(add all Procedure #1 Results together)/ (Total number of records)

In short, Procedure #1 takes the average reduction of the debt in percent for every record for the specific provider (specific UID). Each result is then stored in computer random access memory. Procedure #2 takes the average of all the results for each record stored in memory and produces the "Total ERA" [FIG. 9A item 922]. That variable, "Total ERA," is then stored in the computer's random access memory for use by the Post Analysis Reporting as described in Section V below.

While calculating the results for Total ERA, the computer code will also calculate the Total ERA Risk Ratio ("Total ERA RES") by averaging the RES results [FIG. 9A item 960]. After the Total ERA RES is calculated, the Total ERA Cost to Work File [FIG. 9A item 942] and the Total ERA Risk Ratio [FIG. 9A item 958] will be determined.

Total $ERA\ RES$=(Sum of all $RES$ records based on criteria)/(number of records)

Total $ERA$ Cost to Work File=(((Total $ERA\ RES$ in decimal form)*(average cost to work file))+ (fixed costs+Risk %)

Total $ERA$ Risk Ratio=(Total $ERA\ RES$/100)

It is noted that the "[Specific Calculation: Total ERA, Specific ERA, DMDRA, etc.] Cost To Work File" are mathematical algorithms that predicts how much it will cost the PODS entity to obtain a settlement, while the "[Specific Calculation: Total ERA, Specific ERA, DMDRA, etc.] Risk Ratio" are mathematical algorithms that predicts the chances that purchasing the debt will result in a monetary loss to the PODS entity.

If the Total. ERA Cost to Work File [FIG. 9A item 942] is greater than the Selling Price, where the Selling Price means the price the Debtor/Seller would pay for the PODS system to accept the debt liability, minus the Total ERA price [FIG. 9A item 922], then no offer to purchase the debt will be made (said another way, the Selling Price must be greater than the Total ERA Price+Total ERA Cost to Work File). Further, if the Total ERA Risk Ratio [FIG. 9A item 958] is too high, as predetermined by the PODS entity, then no offer to purchase the debt will be made. The reason is the risk of losing money is too high.

Calculation Method #2—Specific ERA:

The basic premise of this calculation method is to identify an acceptable Settlement Price based on an experience rating. This experience rating is the amount of the debt, plus and minus a delta variable amount inputted by the PODS entity for all historic records. The result is the historical reduction, for a given dollar amount+/–a given dollar amount. Note: this calculation is not "provider specific" but specific to the dollar amount+/–a delta for all records in the database.

Example: If the debt owed is $2,000 and the delta variable amount inputted was $500, then all historical settlements where the amount owed was between $1,500 and $2,500 would be searched and the average discounted would be the result given to the end user at the PODS entity.

The second result, which will be referred to as "Specific ERA" [FIG. 9A item 924], is based on a mathematical model embodied in computer code for each data record where the debt amount in the new data table is equal to the debt amount inputted [FIG. 1A-1 item 120 or FIG. 1B-1 item 120], plus and minus, a dollar amount that was predefined by the entity using the PODS system. The same steps used to determine the "Total ERA" are used, the only difference being that the records analyzed are limited by the debt amount (variable BAL, below in Table #1), plus and minus, a predetermined amount identified by the entity using the PODS system. That variable, "Specific ERA," is then stored in computer random access memory, or on computer readable storage medium, for use by the Post Analysis Reporting as described in Section V, below. A Post Analysis report is used since large debts often get a bigger reduction than small debts.

While calculating the results for Specific ERA, the computer code will also calculate the Specific ERA RES (i.e., Specific ERA resistance) by averaging the RES results [FIG. 9A]. After the Specific ERA RES is calculated, the Specific ERA Cost to Work File [FIG. 9A item 944] and the Specific ERA Risk Ratio [FIG. 9A item 946] will be determined, Specific $ERA\ RES$=(Sum of all $RES$ records base on criteria)/(number of records)

Specific $ERA$ Cost to Work File=((Specific $ERA\ RES$ in decimal form)*(average cost to work file))+ (fixed costs+Risk %)

Specific ERA Risk Railo=(Specific ERA RES/100)

If the Specific ERA Cost to Work File [FIG. 9A item 944] is greater than Selling Price minus the Specific ERA [FIG. 9A item 924], then no offer to purchase the debt will be accepted (said another way, the Selling Price must be greater than the Specific ERA+Specific ERA Cost to Work File). Further, if the Specific ERA Risk Ratio [FIG. 9A item 946] is too high, as determined by the PODS entity, then no offer to purchase the debt will be made.

It is noted that the experience data should have enough records in it to develop a true statistical sampling. Further, records over 3 years, provided there are a sufficient number of records for a statistical sampling, should be deleted. The reason is because a provider's practices will change with new management and the best way to have analytical results reflect the way the creditor reacts to the PODS system is to use current data records only. This way, the experience data table is reflective of the creditor's actions at any given period in time.

Table #1:

Table #1 is found in FIG. 19A through FIG. 19C. Table #1 is element 126 in FIG. 2.

Table #1 and the other databases [FIG. 2 element 126, FIG. 2 element 130, FIG. 2 element 142, FIG. 2 element 152, FIG. 2 element 120] created for the PODS entity databases are designed based on the collection, selection, accessing of, and arrangement of data elements. The design and implementation was structured in a manner as to save CPU processing resources; save processing time associated with accessing the data elements stored in the database; limit the amount of space needed to store the database; improve the accessibility of the data by third-party computers and communications requests seeking to access the databases and elements therein.

Calculation Method #3—Direct Match Debt Amount Rating Analysis:

The basic premise of this calculation method is to identify an acceptable Settlement Price based on an experience rating. This experience rating is the amount of the debt, plus and minus a delta variable amount inputted by the PODS entity and is based on a specific provider's historic settlement data. The result is the historical reduction, for a given dollar amount; for a specific provider.

Example: If the debt owed is $2,000 for ABC Hospital. All historical settlements where the amount owed was approximately $2,000 and the LAD was for ABC Hospital would be searched and the average discounted would be the result given to the end user at the PODS entity.

The mathematical model embodied in computer code for the Direct Match Debt Amount Rating Analysis (herein "DMDRA") is determined through the following process. After verifying that the LIDS match, the following steps will occur. Each record in the experience data table [FIG. 2 element 126] where the variables listed below in Table #2 match the inputted variables in [FIG. 1A-1 through FIG. 1A-7 or FIG. 1B-1 through FIG. 1B-7], will be determined to be a valid record and all the records will make a new, temporary, experience data table for this analysis [FIG. 2 element 138].

Example:

If the following fields match, then the record is inserted into the new, temporary, experience data table [FIG. 2 element 138]:

TABLE #2

Inputted BAL = (BAL) +/- (a predefined variable in the new experience table).
Inputted COL = COL variable in the new experience table.
Inputted LAW = LAW variable in the new experience table.
Inputted IN = IN variable in the new experience table.
Inputted HI = HI variable in the new experience table.
Inputted DED = DED variable in the new experience table.
Inputted ME = ME variable in the new experience table.
Inputted A = A variable in the new experience table.

Once the new, temporary experience database [FIG. 2 element 138] is created, computer code with a mathematical model embodied in computer code [FIG. 2 element 130] in it will be run over the new experience data table. The code that will be run is the same as described in the Experience Rating Analysis (ERA) section above, the only difference being that valid records are determined if the variables listed in Table #2 described above match. The execution of this code will result with the variable DMDRA. That variable, "DMDRA", is then stored in computer RAM memory, or on a computer readable storage medium, for use by the Post Analysis Reporting as described in Section V, below.

While calculating the results for DMDRA, the computer code will also calculate the DMDRA RES by averaging the RES results [FIG. 9A item 938]. After the DMDRA RES is calculated the DMDRA Cost to Work File [FIG. 9A item 948] and the DMDRA Risk Ratio [FIG. 9A item 950] will be determined.

$$\text{DMDRA } RES = (\text{Sum of all } RES \text{ records based on criteria})/(\text{number of records})$$

$$\text{DMDRA Cost to Work File} = ((\text{DMDRA } RES \text{ in decimal form})^*(\text{average cost to work file})) + (\text{fixed costs} + \text{Risk \%}))$$

$$\text{DMDRA Risk Ratio} = (\text{DMDRA } RES/100)$$

If the DMDRA Cost to Work File [FIG. 9A item 948] is greater than the Selling Price minus the DMDRA price [FIG. 9A item 926], then no offer to purchase the debt will be made (said another way, the Selling Price must be greater than the DMDRA Price+DMDRA Cost to Work File). Further, if the DMDRA Risk Ratio [FIG. 9A item 950] is too high, as determined by the PODS entity, then no offer to purchase the debt will be made.

Calculation Method #4—Global Analysis:

The basic premise of this calculation method is to identify an acceptable Settlement Price based on the attributes of a claim (i.e., in-network or out-of-network; how much owed is deductible vs balance billing; etc.). Each claim variable is assigned a weighted value to prioritize or minimize the variable's importance in the equation and final result.

Based on the data inputted in [FIG. 1A-I through FIG. 1A-7 or FIG. 1B-I through FIG. 1B-7], the variables described above and in Table #3 below will be used to develop the Global Analysis. The mathematical model embodied in computer code for the Global Analysis (herein referred to as "GA") is:

TABLE #3

Whereas WV represents a weight variable. The weighted variable (WV) may be changed by the entity using the PODS system to meet their specific requirements for each variable - this goes to prioritizing or minimizing a variable's importance in the algorithm. For ease of reading the variable WV is used. WV will be specific to each variable, the same WV variable value will not be used for each variable.
Whereas AG is the age of the debt. AG is calculated by subtracting the current date from the date of service.
Whereas FAC indicates if the provider is a facility (i.e., hospital), a medical provider office (i.e., doctor, physical therapist, speech therapist, dentist, durable medical equipment vendor, alternative medicine provider, etc.).
Whereas GEO indicates the geographical region of the provider.
Whereas LIB indicates if there is another payer that should pay the bill (i.e., worker's compensation, an auto insurance plan, home owner's plan or other).
Whereas DEN indicates whether or not the insurance company denied the claim(s).
Whereas APL indicates whether or not the Debtor completed the insurance company's appeal and grievances process.

TABLE #3-continued

Whereas EP is the estimated insurance(s) payment [FIG. 1B-4 item 122].
Whereas NCB is a non-covered benefit and is converted to a numeric value for the purposes of use by the formula. This may be an elective surgery, policy exclusion, denied coverage or other.

If FIG. 1A-1 through FIG. 1A-7 is used:

$$GA=(DED*(WV_1))+((BAL-DED)*((AG*(WV_2))*(HI*(WV_3))*(FAC*(WV_4))*(ELEC*(WV_5))*(IN*(WV_6))*(GEO*(WV_7))*(COL*(WV_8))*(LAW*(WV_9))*(LIB*(WV_{10}))*(ME*(WV_{11}))*(A*(WV_{12}))*(DEN*(WV_{13}))*(APL*(WV_{14}))*(CR*(WV_{15}))*(B*(WV_{16}))*(P*(WV_{17}))*NCB*(PAY*(WV_{18}))$$

Notes:
a) The subscripts denote that the value for the variable WV is different for each instance of WV.
b) The WV variables are in decimal format and the intention for the formulas is to take each attribute of a bill and either multiple it by 1 so the bill remains at full balance (based on the specific bill attribute) or decrease the amount of the bill based on the bill's attribute. In the later example the WV would cause a reduction on the bill and the amount applied to the WV variable would determine the decrease price base on that specific variable.

An alternative embodiment for out-of-network providers is:

$$GA=BAL*((AG*(WV_{20}))*(DEL)*(WV_{21}))*(HI*(WV_{22}))*(FAC*(WV_{23}))*(ELEC*(WV_{24}))*(IN*(WV_{25}))*(GEO*(WV_{26}))*(COL*(WV_{27}))*(LAW*(WV_{28}))*(LIB*(WV_{29}))*(ME*(WV_{30}))*(A*(WV_{31}))*(DEN*(WV_{32}))*(APL*(WV_{33}))*(CR*(WV_{34}))*(B*(WV_{35}))(P*(WV_{36})))*NCB*(PAY*(WV_{37}))$$

Note: NCB is defined later in the disclosure.

If FIG. 1B-1 through FIG. 1B-7 is used as the input mechanism the mathematical model embodied in the software would be:

$$GA=(DED*(WV_{40}))+((BAL-(EP-DED))*((AG*(WV_{41}))*(HI*(WV_{42}))*(FAC*WV_{43}))*(ELEC*(WV_{44}))*(IN*(WV_{45}))*(GEO*(WV_{46}))*(COL*(WV_{47}))*(LAW*(WV_{48}))*(LIB*(WV_{49}))*(ME*(WV_{50}))*(A*(WV_{51}))*(DEN*(WV_{52}))*(APL*(WV_{53}))*(CR*(WV_{54}))*(B*(WV_{55}))*(P*(WV_{56}))*(NCB*(WV_{57}))*(PAY*(WV_{58}))$$

An alternative embodiment for out-of-network providers is:

$$GA=(BAL-EP)*((AG*(WV_{60}))*(DED*(WV_{61})*(HI*(WV_{62}))*(FAC*(WV_{63}))*(ELEC*(WV_{64}))*(IN*(WV_{65}))*(GEO*(WV_{66}))*(COL*(WV_{67}))*(LAW*(WV_{68}))*(LIB*(WV_{69}))*(ME*(WV_{70}))*(A*(WV_{71}))*(DEN*(WV_{72}))*(APL*(WV_{73}))*(CR*(WV_{74}))*(B*(WV_{75}))*(P*(WV_{76})))*(NCB*(WV_{77}))*(PAY*(WV_{78}))$$

It is noted that while the variables are multiplied to determine a final value, the mathematical operator which in the multiplication symbol in this implementation, may be substituted with other mathematical operators ("+", "−", "/", etc.).

Each of the data elements listed above are weighted and based on them, an estimated Settlement Price is determined. The PODS entity will then add a multiplier for profit margins and the Debtor/Seller may accept or decline the offer to sell the debt.

Transforming the age of the debt into a useful result: The age of the debt will be split out into units based on a time interval (i.e., by month, number of days, etc.). Each unit will be assessed a value. That value will determine the weighted variable for AG.

Transforming the amount of the debt into a useful result: The amount of the debt will be split out into units. Example, each $100 unit will be assessed a value. That value will be used to determine the weighted variable for BAL.

Transforming if the debt is part of a deductible into a useful result: If the debt is entirely owed because it is part of a deductible or co-insurance, then it is assigned a value X; if it is not it will be assigned a value of Y. That value will be used to determine the weighted variable for DED.

Transforming if health insurance was in place at the time the debt was incurred into a useful result: If health insurance was in place at the time the debt was incurred, then it is assigned a value X; if it is not it will be assigned a value of Y. That value will be used to determine the weighted variable for HI.

Transforming if the provider was a facility or not into a useful result: If the provider to which the debt is owed is small like a medical office or a physician group, then it is assigned a value X; if it is not it will be assigned a value of Y. That value will be used to determine the weighted variable for FAC.

Transforming the procedure was elective or not into a useful result: If the procedure was elective, then it is assigned a value X, if it is not it will be assigned a value of Y. That value will be used to determine the weighted variable for ELEC.

Transforming the network status into a useful result: If the care was provided by an in-network provider, then it is assigned a value X, if it is not it will be assigned a value of Y. That value will be used to determine the weighted variable for IN. The reason for this is because if a provider is in-network then they are likely getting a lower reimbursement rate from the payer and are bound by contractual obligations between the payer and provider. Further, the patient is the intended beneficiary so the patient too is bound by these contractual obligations/limitations. These contractual obligations make things difficult. In fact, this is why the PODS entity is better served seeking reductions based on billing errors, medical errors, charity care, and things other than the billed charges. In an out-of-network scenario, there are no written contracts and the provider does not have an agreed upon payment price. This means that the PODS entity may, in addition to identifying medical errors, billing errors, charity care, etc., apply case law stating that the billed charges are not fair or reasonable. This makes working out-of-network debts less cumbersome than in-network debt. And if an out-of-network provider makes a patient sign a Financial Responsibility contract, there is little worry as these often fail in court as being non-valid due to duress.

Transforming the geographic region of the provider into a useful result: If the provider is located in a highly populated geographical area or a zip code with a high annual household income as determined by US census data, will be assigned a value X, if it is not it will be assigned a value of Y. That value will be used to determine the weighted variable for GEO.

An alternative method of determining variable GEO is to establish a percent increase paid by Medicare for the zip codes in the United States.

Transforming if the debt has been sent to a collections company into a useful result: If the debt is being managed by the provider, then it is assigned a value X; if it is being handled by an outside collection company it will be assigned a value of Y. If it was being handled by a law firm acting as a collection company it will be assigned the value Z. That value will be used to determine the weighted variable for COL. Note: often law firms will act as collection companies and send dunning notices; this is in contrast to the standard law firm that gives notice to pay the debt then begins litigation.

Transforming if the provider used legal action(s) into a useful result: If legal action(s) was commenced, then it is assigned a value X, if it is not it will be assigned a value of Y. That value will be used to determine the weighted variable for LAW.

Transforming the liability of another insurer into a useful result: If the debt is entirely the liability of another insurance carrier, then it is assigned a value X, if it is partially the responsibility of another insurance carrier it will be assigned a value of Y. If there is no responsibility on the part of another insurance carrier, it will be assigned a value of Z. That value will be used to determine the weighted variable for LIB.

Transforming if the debt is associated with a medical error into a useful result: If the debt is associated with a medical error in some way, then it is assigned a value X, if it is not it will be assigned a value of Y. That value will be used to determine the weighted variable for ME.

Transforming if the claim(s) submitted to the payer for the debt was marked "accept assignment" into a useful result: If the claim sent to the payer was marked "accept assignment" and i) the primary insurer was Medicare or Medicaid; or ii) the state where the care was rendered has case law or a statue that states that by accepting assignment the provider must write-off the balance; or iii) the claim is sent to a commercial insurance company that has a policy that all claims that have "accepted assignment" will be deemed to accept the insurance company's payment as payment in full, will be assigned a value X. If "accept assignment" is not checked, it will be assigned a value of Y. That value will be used to determine the weighted variable for A.

Transforming the Debtor's credit rating into a useful result: Providers, collection companies and other entities use a debtor's credit score to determine if the debtor i) has the means to pay the debt and ii) has a history of paying or defaulting on their debts. Based on this score, creditors will target debtors with high credit scores with aggressive collection efforts because they are more likely to be able to pay and to actually pay the debt. Because of this, the PODS entity knows that a provider or collection company will be more aggressive in collecting on accounts where the debtor has a high credit rating score. The PODS entity also knows that it may charge a debtor with a high credit score more than a debtor with a low credit score because a person with a high credit score is more likely to be motivated to keep a good credit score. The PODS entity also knows that the resistance the provider (or collection company or law firm) will give in settling the debt will increase or decrease based on the Debtor's credit rating. That value will be used to determine the weighted variable for CR.

Transforming if the Debtor is deceased into a useful result: If Debtor is deceased, the value assigned to the variable will be X. If the Debtor is not decease, the value assigned to the variable will be Y. That value will be used to determine the weighted variable for P.

Transforming if the Debtor's is in bankruptcy proceedings into a useful result: If Debtor is in bankruptcy proceedings, the value assigned to the variable will be X. If the Debtor is not in bankruptcy proceedings, the value assigned to the variable will be Y. That value will be used to determine the weighted variable for B and to transform NCB into a result.

Transforming the Payer into a useful result: If the payer is Medicare or Medicaid, it is well known in the industry that the ability to obtain the patient responsibility portion of the debt is unlikely because these patient populations tend to have less money. Further, there are some payers who are known to limit the patient responsibility portions of the bills and these payers will be flagged as it is likely that the payer has already audited the medical bill and because of that, there is are fewer errors and inefficiencies in the medial bill to exploit in order to obtain a reduction. Based on that, if the payer is Medicare or Medicaid, it will be the value assigned to the variable will be X. If not, the value assigned to the variable will be Y.

Transforming a provider discount already given into a useful result: If the provider already gave a discount to the patient, then obtaining another reduction will be difficult. Based on this, PDAG will equal "True" if a discount has already been given and "False" if one has not been given. The basic computation is that if a "PDAG equals True" the provider resistance rating will increase by 3 points.

Transforming if a provider's negative credit ratings into a useful result: If the record has resulted in a negative credit mark at a credit bureau like Equifax or Transunion, then it is assigned a value Y; if it has not, then it is assigned the value N. Further, the data element and computer variable "DNCR" allows the PODS system to calculate when (based on a future date) a negative action will be taken by a provider and what that action will be (i.e. lawsuit, effect credit rating, other).

Note: the PODS entity may assign a value score to be used in its calculation based on each payer.

When the computer executable code is run, the result returned is GA Estimated Settlement [FIG. 9A item 920]. GA will then be stored in computer RAM memory, or on a computer readable storage medium, for use during Post Analysis Reporting per Section V, below.

While calculating the results for GA, the computer code will also calculate the GA Calculated RES [FIG. 9A item 940] by using the following mathematical model embodied in computer code:

$$GA \text{ Calculated } RES = ((DED^*(WV_{80})) + (((BAL-DED)^* (WV_{81}))^*(AG^*(WV_{82}))^*(LAW^*(WV_{83}))^*(COL^* (WV_{84}))^*(IN(WV_{85}))^*(PAY^*(WV_{86}))))$$

An alternative embodiment for out-of-network providers:

$$GA \text{ Calculated } RES = ((AG^*(WV_{90}))^*(BAL^*(WV_{91}))^* (LAW^*(WV_{92}))^*(COL^*(WV_{93}))^*(IV^*(WV_{94}))^* (DED^*(WV_{95}))^*(PAY^*(WV_{96})))$$

Note: The two formulas above calculate the provider resistance (a/ka/ how difficult it will be to obtain a reduction) in negotiating down the outstanding balance.

After the GA Calculated RES is calculated the GA Cost to Work File [FIG. 9A item 952] and the GA Risk Ratio [FIG. 9A item 954] will be determined.

$$GA \text{ Cost to Work File} = ((GA \text{ Calculated } RES \text{ in decimal form})*(\text{average cost to work file})) + (\text{fixed costs} + \text{Risk \%})$$

$$GA \text{ Risk Ratio} = (GA \text{ Calculated } RES/100)$$

If the GA Cost to Work File [FIG. 9A item 952] is greater than the Selling Price minus GA Estimated Settlement [FIG. 9A item 920], then no offer to purchase the debt will be made (said another way, the Selling Price must be greater than the GA Estimated Settlement+GA Cost to Work File). Further, if the GA Risk Ratio [FIG. 9A item 954] is too high, as determined by the PODS entity, then no offer to purchase the debt will be made.

Calculation Method #5—Total ERA Collection Experience Results

The basic premise of this calculation method is to identify the anticipated actions by the provider including an in-house collection letter, sending the file and an outside collection company, affecting the patient's credit rating [FIG. 20 item 2000] or filing a lawsuit against the patient/guarantor. Each action will be based on the age of the debt and the amount of the debt. Based on these results, the PODS entity can determine what adverse actions to expect from a provider based on the age and amount of debt.

Total ERA Collection Experience:

When the temporary Experience Rating Table [FIG. 2 element 126] is created for the "Total ERA" data analysis, the variables COL and LAW will both be sets of the Boolean value of "n" ("n" indicates a value of "no" or "false"). Computer code with the mathematical algorithm described herein will then be run over the new, temporary data table [FIG. 2 element 138] to determine if there is any indication if either variable COL or LAW contains a "y" in the data table. Each instance of a "y" will be calculated and displayed by the computer software [FIG. 9B]. When the collection experience ratings are being analyzed, the PODS software will also make a predictive analysis of the percent probability of an adverse event being made based on the inputted data.

[FIG. 9B item 990] indicates to the PODS entity that there are 137 records in the data table and never, as indicated by the "NO," has the provider caused a negative credit rating for the debtor and never, as indicated in the report, has the provider ever commenced any legal action(s). In such a situation, the PODS entity may be aggressive in demanding a settlement with the provider because the PODS entity knows that historically there are no consequences for not settling the outstanding debt. If, the results read like [FIG. 9B item 995] the PODS entity would know that the provider is very aggressive in their collection activities, and there is a 64% chance of a negative credit rating and an 18% chance of being sued if the dollar amount is over $5,000. Based on such data, the PODS entity would know to actively seek an acceptable settlement amount quickly.

Specific ERA Collection Experience and DMDRA Collection Experience:

The same process as described above would be implemented the only difference being that the temporary data table [FIG. 2 element 138] will be used. In the case of the "Specific ERA Collection Experience" [FIG. 9A item 932] the data from the "Specific ERA" Experience data table would be used. In the case of the "DMDRA. Experience," the data from the "DMDRA ERA" [FIG. 9A item 934] Experience data table would be used.

Specific ERA Cost to Work File [FIG. 9A item 944] and Specific ERA Risk Ratio [FIG. 9A item 946] will be calculated the same way the Total ERA Cost to Work File and the Total ERA Risk Ratio were, the only difference being that the temporary data table [FIG. 2 element 138] for "Specific ERA" Experience data table would be used.

Calculation Method #6—Medicare Allowable Amount Plus Profit

The reference article "Survey of Charges Billed by Out-Of-Network Providers: A Hidden Threat to Affordability. By: America's Health Insurance Plans, January, 2013" illustrates the difference between what providers charge and what Medicare deems to be an appropriate reimbursement rate. Based on that, the basic premise of this calculation method is to identify an acceptable Settlement Price based on the Medicare Allowable Amount. Then added to that are all of the other costs and mathematical models. Note: The Medicare Allowable Amount may be replaced with cost data provided by private companies.

The Settlement Price is based on the formula below, and could hold up in a court of law hut would i) risk bad credit ratings, ii) risk a law suit and iii) risk a monetary loss based on the cost of the lawsuit and any monies awarded to the provider by the court. This implementation is the same basic embodiment but is a floor that would survive scrutiny by a court of law is calculated based on Medicare data followed by a "take it or leave it" offer via a payment.

Companies have forced settlements by calculating the amount the entity is willing to pay the provider at the Medicare Allowable Amount plus a percent profit for the provider. The percent profit (herein "Provider Profit %") is often between twenty percent (20%) and forty percent (40%) of the Medicare rate.

The transformative expansion/adaptation on this model for this calculation utilizing the PODS system is the following:

The amount of "Provider Profit %" is determined by the PODS entity, there is no fixed amount for all entities. A good rule of thumb is twenty percent to forty percent of the Medicare rate.

"Profit to PODS entity" is a minimum percent profit margin the PODS entity uses in establishing the purchase price from the Debtor/Seller.

"Medicare Allowable Amount" (also referred to as the "Medicare rate") is the reimbursement rate that Medicare established for an episode of care (charges are based on CPT codes, HCPCS codes, REV codes, Current Dental Terminology Codes, etc). For care that is not covered by Medicare, the rate is established by independent companies that publish usual and customary reimbursement rate schedules.

The Formula for determining the Settlement Price to the provider:

$$\text{Provider "Settlement Price"} = (\text{Medicare Allowable Amount}) + (\text{Provider Profit \%})$$

Note: The advantage to this calculation is method is that courts have ruled on the validity of basing a calculation on the Medicare Allowable Rates plus a profit. To that end, it builds in legal scrutiny by a court for the PODS entity if there is no settlement and the case proceeds to litigation. The down side to this method is that may not be as profitable a result when compared to an experience rating as described in other calculation methods herein and does not take into account reductions based on the age of the bill, etc. The legal theory behind this is litigation based on The Medicare Allowable Amount plus a profit versus. Case law where the fair market value is determined to be what the provider accepts from insurance companies as payment in full. Because insurance companies often pay less than the Medicare Allowable Amount Plus a profit, money may be lost with this implementation.

Further, the other calculation methods give better predictive assurances that i) the case will not be litigated. ii) The PODS entity will not lose money based on the cost to work the file. iii) The Seller will not be harassed by the provider making the PODS entity a better corporate partner for Sellers. iv) etc.

This calculate may also be used to make a determination whether or not to make an offer to purchase the debt liability from the Seller. Simply, as another financial error control method, if FIG. 9A item 956 plus the cost to work the file is greater than the Selling Price, then no offer will be made to the Debtor/Seller; otherwise an offer will be made.

Calculation Method #7—Medicare Rate vs. Cost-to-Charge Ratio

The basic premise of this calculation method is to identify an acceptable Settlement Price based on the higher of the Medicare Allowable Amount or the provider's cost-to-charge ratio; whichever is greater. Then added to that are all of the other costs and mathematical models. Note: The Medicare Allowable Amount may be replaced with cost data provided by private companies.

Yet another mathematical calculation implementation of the invention described herein is to use the disclosed methods to buy the medical debt from the Seller. Then force a settlement amount[1] (as opposed to reaching a settlement amount that mutually agreeable to both parties), based on the formula below, that would hold up in court but would risk bad credit ratings and a law suit.

Calculation Step 1:

Obtain the actual costs reported to the Centers for Medicare and Medicaid ("CMS") from by the provider, and the ratio of those costs to the charges made to patients and health plans. These cost-to-charge ratios are audited by CMS and they are recognized as an industry standard. Then add the "Provider Profit %" to these Medicare rates and that will determine the "Usual and Customary Rate (a\k\a "UCR")" for this Step 1.

Calculation Step 2: Obtain the Medicare Allowable Amount under the Medicare Fee Schedule for the same services in the geographic area, and add the "Provider Profit 94," to that amount and that will determine the "Usual and Customary Rate" (UCR) for this Step 2.

Calculation Step 3

The Final Usual and Customary Rate (herein "FUCR") to be used in the formula below will be the higher amount identified in Step 1 and Step 2 as described above.

Calculation Step 4

Take the FUCR. rate determined above and apply the following:

The Formula for determining the Settlement Price to the provider:

Provider "Settlement Price"=(FUCR rate)

Note #1: The advantage to this calculation method is that courts have ruled on the validity of basing a calculation on the Medicare Allowable Rates plus a profit. To that end, it builds in legal scrutiny by a court for the PODS entity if there is no settlement and the case proceeds to litigation. The down side to this method is that may not be as profitable a result when compared to negotiations based on an experience rating as described in other calculation methods and does not take into account reductions based on the age of the bill, etc. The legal theory behind this is litigation based on The Medicare Allowable Amount plus a profit vs. case where the fair market value is determined to be what the provider accepts from insurance companies as payment in full. Because insurance companies often pay less than the Medicare Allowable Amount Plus a profit, money may be lost with this implementation.

Further, the other calculation methods give better predictive assurances that i) the case will not be litigated. ii) The PODS entity will not lose money based on the cost to work the file. iii) The Seller will not be harassed by the provider making the PODS entity a better corporate partner for Sellers. iv) etc.

This calculation may also be used to make a determination whether or not to make an offer to purchase the debt liability from the Seller. Simply, if FIG. 9A item 958 plus the cost to work the file is greater than the Selling Price, then no offer will be made to the Debtor/Seller; otherwise an offer will be made.

Calculation Method #8—Average PODS Entity Discount Analysis

The basic premise of this calculation method is to identify an acceptable Settlement Price based on the average of all historic settlements that the PODS entity has. Then added to that are all of the other costs and mathematical models.

The mathematical calculation implementation of the invention described herein is to estimate the provider's settlement amount based on the average discount the PODS entity using this invention obtains, plus money for risk, plus money for the cost to work the file and money for the error margin. The average discount may be calculated for a specific provider, a specific type of entity (i.e., hospital) or the average for all providers.

Sample mathematical formula for an average discount for an average specific provider [FIG. 9A. item 960]:

Average Specific Provider Discount=(((All specific provider settlements in database total debts owed for that specific provider))*100))+(money to compensate for error margin)±Risk %+cost to work file))

Sample mathematical formula for an average discount for a specific type of provider:

Average Specific Provider Type Discount=(((All specific type provider settlements in database/total debts owed for that specific provider))*100))+ (money to compensate for error margin)+Risk %+cost to work file))

Sample mathematical formula for an average discount for all providers:

Average Discount=(((All settlements in database/ total debts owed for that specific provider)) *100))+(money to compensate for error margin)+Risk %+cost to work file))

Calculation Method #9—Average Insurance Payment

The basic premise of this calculation method is to identify an acceptable Settlement Price based on the average of all historic settlements that the PODS entity has for a specific provider [FIG. 2 element 126] based on the payments from private payers.

For every record in the experience database [FIG. 2 element 126], each record will be analyzed for the amount paid by a private payer based on the line item charge, like a CPT code. During this analysis Medicare, Medicaid and Tricare payments will not be used. All valid data will then be placed in a new temporary database [FIG. 2 element 138]. While the data is being stored in a temporary database, it could alternatively be stored in the computer's random access memory [FIG. 17 item 1932]—if enough random access memory is available.

Two calculations will not be performed over the data in the temporary database. The calculations will be calculating the average payment for line item charge (e.g., CPT code), for a specific provider, for in-network payments and a separate calculation for out-of-network payments.

Case law, such as Temple University Hospital, Inc. v. Healthcare Management Alternatives, Inc., 832 A. 2d 501 (2003), states that the fair market value of services is not what the provider charges, but what the provider receives as a standard insurance payment/reimbursement in its community. Based on that, this is a calculation that may be used based on a line item analysis of bills and EOBs.

> In-Network Average Insurance Payment=(IAA) for each line item charge that is in-network [FIG. 9A item 962].
>
> Out-of-Network Average Insurance Payment=(IAA) for each line item charge that is out-of-network [FIG. 9A item 964].

If there is no EOB available then the Average Insurance Payment will be calculated the following way:

> In-network Average Insurance Payment=(*TBC–BAL*) for each line item charge that is in-network [FIG. 9A item 962].
>
> Out-of-network Average Insurance Payment=(*TBC–BAL*) for each line item charge that is out-of-network [FIG. 9A item 964].

Calculation Method #10—Leverage Settlement Method

This disclosure estimates a provider's Settlement Price and then seeks to ensure the Selling Price is greater than that. There are implementations where the Selling Price may be lower than the estimated Selling Price:

- Situation #1: If a PODS entity was to accumulate a mass volume of debt for a single provider (e.g., $1,000,000) then the PODS entity could settle the cases for less than the estimated selling prices based on the negotiating leverage. To that end, the PODS entity could actively accept cases where the Selling Price is equal to, or lower than, the estimated Settlement Price.
- Situation #2: If the PODS entity structured an up-front or back-end fee (e.g., an analysis fee, membership fee, success fee) the PODS entity could use that money for profit margins, operating costs or other. To that end, the PODS entity could actively accept cases where the Selling Price is equal to, or lower than, the estimated Settlement Price.

Calculation Method #11—Charity Care Method

The Affordable Care Act mandated that providers actively offer charity care (also known as financial assistance) to patients. Further, providers know that impoverished patients seldom pay their bills, or even make payments toward their outstanding balances. Based on the charity cared offered by providers, an entity implementing the PODS process may base a decision to accept a debt liability, in exchange for payment (i.e., buy the debt), based on the patient's financial status.

Providers have different criteria for providing charity care to patients. Some providers insist the patient apply for and be denied by Medicaid prior to offering charity care. Other providers simply require that the patient be equal to or below the federal government's published poverty level guidelines; and yet others state that the patient must be below 150% of the poverty guidelines. An exemplary charity care guideline may be found in FIG. 23A and FIG. 23B. Based on these criteria, the PODS entity could determine if the patient/Debtor would qualify for financial during the time the PODS entity performs its calculations and mathematical modeling in determining to make an offer to accept the debt liability from the patient/Debtor.

To facilitate a decision based on charity care, the PODS entity will keep each provider's charity care guidelines in a binary electronic structure stored on computer readable medium (database). This data [FIG. 2 element 152] stores each provider's charity care guidelines, including mandates like the patient must first be denied Medicaid, does the provider require the patient to provide copies of their tax returns, and all other requirements specific to each provider.

To make a determination based on the patient's financial status, a few pieces of information will be needed. The first step is to obtain the amount of the patient's outstanding debt (BAL), the name of the specific provider, annual income [FIG. 1A-7 item 170 or FIG. 1B-7 item 180], the number of people who live in the residence [FIG. 1A-7 item 172 or FIG. 1B-7 item 182], the age of the debt, and any assets owed by the patient [FIG. 1A-7 item 174 or FIG. 1B-7 item 184]. The second step is to query the charity care database for the specific provider's charity care criteria [FIG. 2 element 152]. The final step is to apply a computer program to this data that results in a determination as to whether or not charity care will likely be applied by the specific provider. These results are then reported to the broker/sales agent and/or the PODS entity [FIG. 9A item 970]. These results are also used to make automated decisions on whether or not to purchase the debt (accept the debt liability) from the Debtor/Seller.

Exemplary computer implemented program for determining charity care eligibility:

```
"##" <- these symbols mean this is a comment in the code
"$" <- this symbol before a variable means the variable is being used as a computer variable
###The following code is written that an average person can interpret its meaning
If ((($patient's_annual_income) < ($provider's_poverty_levels_for_charity_care))
        And (($patient's_assets) < ($provider's_charity_care_asset_criteria))
        And ($debt_is_not_in_collections))
    {
        $The_patient_is_eligible_for_charity_care_and_the_Settlement_Price = (BAL*.25)
    }
Elseif ((($patient's_annual_income) < ($provider's_poverty_levels_for_charity_care))
        And (($patient's_assets) < ($provider's_charity_care_asset_criteria))
        And ($debt_is_in_collections) and ($debt < $24_months_old))
        ##   Then statement below
```

```
{
    $The_patient_is_eligible_for_charity_care_and_the_Settlement_Price = ($BAL*.80)
}
Else ($BAL > $24_months_old)
        ##commented   Then begin below
    {
        $Settlement_Price = $BAL
    }
```

Effect of Charity Care on Settlement Price

If the patient is eligible for charity care as based on the calculations made, then the Settlement Price may be reduced by a percent; this percent may be determined by the entity using the PODS system. Note: it is the point of this calculation to allow the Seller to benefit from the charity care offered by the facility then assist the Seller by accepting was is left of the patient responsibility portion of the debt at a reduced fee.

As a general rule:
  i) the Settlement Price may be reduced by seventy five percent (75%) if the debt has not gone to collections. Note: the 75% number may be increased or decreased by the PODS entity based on their experience rating in obtaining charity care.
  ii) If the debt has gone to collections, the Settlement Price may be reduced by twenty percent (20%). The reason for the lesser reduction is that often charity care is not allowed once a bill has been sent to collections. Note: the 20% number may be increased or decreased by the PODS entity based on their experience rating in obtaining charity care.
  iii) If the debt is greater than 24 months old, then no reduction will be applied to the Settlement Price because the possibility of obtaining charity care is not likely. Note: the reduction of 0% may be increased by the PODS entity based on their experience rating in obtaining charity care.

Calculation Method #12—Provider Already Provided a Discount

If the provider already provided a discount [FIG. 1A-1 item 121 or FIG. 1B-1 item 121] then, for each calculation that uses a resistance rating (computer variable "RES"), the resistance rating will be increased by 3 points. This is based on a scale of 0 to 10; the maximum value being 10.

The estimated Settlement Price for the provider will also be increased by X percent (X %). X % is a variable determined by the PODS entity but may be something like 10 percent (10%) Example: if the estimated Settlement Price was $100, then the estimated Settlement Price will be recalculated to be $100+10%=$110 if the provider already gave a discount.

V Post Analysis Reporting:

Reporting to Sales Person, Broker or Intermediary:

FIG. 9A and FIG. 9B are examples of reporting for sales people, brokers and/or intermediaries. in such an implementation, the estimated settlement amount [FIG. 9A; and each item including item 920, item 922, item 924, item 926, item 942, item 956, item 958, item 922, item 960, item 962, item 964, item 970] is reported to the sales person/broker. The sales person/broker may then add the profit margins, commissions and any other variable to the end result and negotiate a final Selling Price with the Debtor/Seller. Of interest is that the different estimated Settlement Prices (i.e., ERA, DMDRA, Medicare calculations, etc) give the sales people a very good indication of a settlement amount based on different approaches; all the sales person has to do is to select a dollar amount and utilize that. Further, FIG. 9A item 956 and FIG. 9A item 958 provide a fallback price upon which the PODS entity may safely use as these settlement amounts will withstand a lawsuit based on current case law.

Also available to the sales person/broker are the calculations provided in the Estimated Selling Prices to the Seller/Debtor as computed in Section XV—entitled "Estimated Selling Point." These calculations may be helpful to the sales person/broker because they contain historical data and algorithms on how to maximize the fee to accept from the Seller/Debtor.

Once a final Selling Price is negotiated between the entity using the PODS system (or an intermediary) and the Debtor/Seller, the final Selling Price is inputted into the system and an agreement [FIG. 3-1 through FIG. 3-6, FIG. 4-1 through FIG. 4-6 or FIG. 5-1 through FIG. 5-6 is created utilizing the data the sales person, broker or intermediary: inputted in FIG. 1A-1 through FIG. 1A-7 or FIG. 1B-1 through FIG. 1B-7. This transformed document would then be sent to the Debtor/Seller via email, displayed by computer software, US mail, facsimile or other method for acceptance of the terms and conditions.

Once one of the agreements [FIG. 3-1 through FIG. 3-6, FIG. 4-1 through FIG. 4-6 or FIG. 5-1 through FIG. 5-6] has been accepted [FIG. 3-6 item 128, FIG. 4-6 item 128 or FIG. 5-6 item 128], electronic documents including instructions for repairing credit [FIG. 10] and a letter accepting liability for the debt [FIG. 6A, FIG. 7A or FIG. 8] would be transformed with the data inputted from [FIG. 1A-1 through FIG. 1A-7 or FIG. 1B-1 through FIG. 1B-7] and sent to the Debtor/Seller via email, displayed by computer software, US mail, facsimile or other method. At this same time, the transformed documents [FIG. 6B, FIG. 6C, FIG. 61), FIG. 6E, FIG. 713, FIG. 7C, FIG. 7D or FIG. 7E] would also be sent to the provider and/or collection company that is owed the debt stating that the debt is owned by the PODS entity.

The purpose of sending [FIG. 6B or FIG. 7B] to the provider/creditor is to create a legal agreement where the PODS entity is now responsible for the outstanding monies and not the patient/debtor. To accomplish this [FIG. 6B or FIG. 7B] is sent stating that unless the provider/creditor objects to the PODS entity being responsible for the outstanding monies within ten (10) business days, then it is mutually agreed that the PODS entity is now responsible for the outstanding money. Further, by sending a nominal payment along with the letter the PODS entity is building a case for contract by assent and/or contract by constructive knowledge. Another way to approach this is by having the provider/creditor sign an agreement/document stating that the provider/creditor agrees to the transfer of liability to the PODS entity [FIG. 6C or FIG. 7C].

Reporting to Seller/Debtor:

FIG. 3-1 through FIG. 3-6, FIG. 4-1 through FIG. 4-6, FIG. 5-1 through FIG. 5-6, and FIG. 15 are examples of post analysis reporting to the Seller/Debtor and a contractual offer to a Seller/Debtor.

The Offer Price to the Seller/Debtor:

If there is no broker, agent or representative to negotiate the Selling Price, then Section XV—entitled "Estimated Selling Point" will be implemented; this implementation is fully automated. The PODS entity will implement a process to determine which Estimated Selling Point calculation to use when determining the Seller/Debtor's final purchase price ("Selling Price") upon completion of Section XV—entitled "Estimated Selling Point."

Once the final Selling Price is computed/decided, it will make this offer to the Seller/Debtor [FIG. 15, FIG. 13-B element 1410]. If the offer is declined, then the PODS entity may offer a lower price. If not accepted, the process is terminated [FIG. 13-B element 1430]. If the Seller/Debtor accepted the offer, then the transformative agreements [FIG. 3-1 through FIG. 3-6, FIG. 4-1 through FIG. 4-6 or FIG. 5-1 through FIG. 5-6] will be presented to the Seller/Debtor. The Selling Price is found in these transformative documents at [FIG. 3-1 item 120, FIG. 4-1 item 120, FIG. 5-1 item 120].

The transformative agreement [FIG. 3-1 through FIG. 3-6, FIG. 4-1 through FIG. 4-6 or FIG. 5-1 through FIG. 5-6] is created using predefined language stored in a physical binary structure stored on computer readable medium (i.e., a computerized database) and when processed, inputs data including Seller's name, address, information on the debt, amount for which the PODS entity is accepting the debt liability, etc., into the transformative agreement. If the offer to the Seller/Debtor is declined [FIG. 13-B element 1470], then the process is terminated. If the agreement is accepted [FIG. 13-B element 1490], then the PODS entity accepts the liability and begins working the debt as outlined in Section VII—"Working the Debt."

An alternative embodiment and formula for estimating the purchase price from the Debtor based off methods described in Calculation Method #6:

Purchase price from Seller ("Selling Price")=((Medicare Allowable Amount for all care)+(Provider Profit %)+(average cost to work file)+(fixed costs)+(Profit to PODS entity)+(Risk %))

An alternative embodiment and formula for estimating the purchase price from the Debtor based off methods described in Calculation Method #7:

Purchase price from Seller ("Selling Price")=((FUCR rate)+(average cost to work file)+(fixed costs)+(profit to PODS emit))+(Risk %))

Actions Based on the Transformative Variables:

The variables "Selling Price," "Settlement Price," "RES," "Cost to Work File" and "Risk Ratio" are used to determine if the PODS entity wants to make an offer to Debtor/Seller for the outstanding debt. If, after applying mathematical modeling to these variables, the PODS entity determines that the risk of monetary loss due to i) risk on part of the provider, ii) risk based on a loss due to the cost of working the file or iii) insufficient profits, then no offer to purchase the debt will be made.

Similarly, the "Selling Price" variable will be used by the Debtor/Seller to determine if Debtor i) wants to sell the debt for the amount offered, ii) can find a better offer elsewhere, or iii) has a tax incentive, or other, that offers a greater incentive than selling the debt at the price offered by the PODS entity.

VI. Transferring the Debt

Discussion on Step-In Entity & Guarantor Implementation:

As a matter of clarification, a "step-in" entity is a legal agreement between the patient and the PODS entity where the PODS entity agrees to step-in and assume all liabilities, legal expenses, penalties and other for the patient/Debtor by acting as the guarantor; then working to settle the accounts at a lesser amount. It is a simple agreement between the two parties that does not need to be acknowledged by the provider/creditor as the agreement is between the patient/Debtor and the PODS entity—it is a private agreement.

While the step-in entity is a private agreement between the patient/Debtor and the PODS entity, the guarantor methodology [FIG. 4-1 through FIG. 4-6] provides notification to the provider/creditor. The point of sending notice under a guarantor implementation is to provide notice and bind the provider to accepting the agreement via assent and identifying, and thereby avoiding, issues like a provider's non-transfer policy and possible tortious interference. This same notice may be made under the step-in entity implementation if the PODS entity wants to implement it.

Discussion on Acknowledging the Transferring Debt:

It is best practices that the provider/creditor acknowledge (i.e., sign a confirming document, acknowledge via email, or other) the transfer of the patient responsibility portion of the debt to the PODS entity [FIG. 6C, FIG. 6E, FIG. 7C or FIG. 7E]. While that is best practices, there are problems with that implementation that include limited time by providers to sign such documents; a new business practice like transferring a patient debt is hard to implement; and providers are generally not in the practice of "follow-up paperwork." Providers generally have patients fill out forms upon arrival, after that time providers send invoices or collection notices but do no other types of paperwork (a/k/a/ follow-up paperwork). Such an example of follow-up paperwork would be an invoice marked "paid in full."

The process of transferring the debt described in this disclosure addresses the provider acknowledging the transfer of debt and other ways to ensure a binding transfer of debt, to a third-party, without the provider having to sign (or an electronic acknowledgement) a legal document allowing the transfer.

Discussion on Language Necessary for the Transformative Legal Agreements (Legal Contracts):

There are necessary requirements, both legally and for operational/practical purposes, with regards to agreement between the PODS entity and the Seller/Debtor [FIG. 3-1 through FIG. 3-6, FIG. 4-1 through FIG. 4-6 or FIG. 5-1 through FIG. 5-6]. They include:
  a) The agreement needs to be in writing; an electronic agreement meets this requirement.
  b) The agreement needs to have a clause that transfers the debt liability from the Seller/Debtor to the PODS entity. This may be by accepting novation of the liability [FIG. 3-1 through FIG. 3-6]; becoming the guarantor of the liability [FIG. 4-1 through FIG. 4-6]; or acting as a step-in entity [FIG. 5-1 through FIG. 5-6].
  c) The agreement needs to have consideration (i.e. money in exchange for transferring the liability and state that there is consideration. This is the Selling Price [FIG. 3-1 item 120, FIG. 4-1 item 120, FIG. 5-1 item 120].
  d) The agreement should have an indemnification clause where the PODS entity indemnifies and holds the Seller/Debtor harmless for the liability associated with the debt. e) The agreement needs to be signed by an authorized party for the PODS entity and the Seller/Debtor. An electronic signature meets this requirement.
  f) The agreement needs to be dated.
  g) The agreement must outline the debt that is the subject of the agreement.

h) The agreement may include an assignment of insurance coverage(s) due from the Seller/Debtor/patient to the PODS entity.
i) The agreement should state that the Seller/Debtor will supply the PODS entity with the needed documents that include the bill, medical records, EOB(s).
j) The agreement should state that the Seller/Debtor will answer questions.
k) The agreement should state that the patient will sign HIPAA consent form as needed allowing the PODS entity access to records, appeals, claims data, provider conversations and other.
l) The agreement should have a hold harmless clause where the Seller/Debtor is held harmless for all liabilities.
m) The agreement must disclose any potential harm to the Debtor/Seller (e.g., negative credit rating).
n) The agreement must meet all requirements to be a binding agreement based on federal and state laws.
o) The agreement should have a "cool down" clause; a 3 day cancelation period.
p) The agreement should state that the PODS entity may gain or lose money on the engagement and that any gain or loss is PODS' gain or loss.
q) An effective date of the agreement.
r) If novation [FIG. 3-1 through FIG. 3-6] is being used then the agreement should state that the patient is discharged from their responsibility(s) under the patient's agreement with the provider. Further the notice to the provider [FIG. 6B, FIG. 6C, FIG. 6D, or FIG. 6E] should indicate that the agreement between the patient and provider is discharged and replaced by a new agreement (where the PODS entity assumes all the liabilities of the old agreement) between the provider and the PODS entity is in effect.
s) State and federal laws and regulations change. Based on that, PODS entity should continually review state and federal requirements to determine if a signature is required to authorize the a novation [FIG. 3-1 through FIG. 3-6]. If a signature is required, the PODS entity should not use FIG. 6B or FIG. 6D; it should only use FIG. 6C or FIG. 6E.

Discussion on Negative Consequences:

As discussed herein, one advantage to the patient/Debtor is that when a debt is novated and all liabilities transferred to the PODS entity is done properly, the patient/Debtor is immune from negative consequences of the debt. Negative consequences include, but are not limited to, actions such as lawsuits, negative credit marks on their credit report and attempts from collection companies to collect the debt. The avoidance of such negative consequences is a benefit, especially when combined with paying the liability at a reduced rate. When the PODS entity is acting as the guarantor [FIG. 4-1 through FIG. 4-6] or step-in entity [FIG. 5-1 through 5-6], the patient/Debtor is not immune from the negative consequences, though a legal defense is supplied by the PODS entity. It is only when the debt is transferred via novation [FIG. 3-1 through FIG. 3-6] that the patient/Debtor is protected from negative consequences.

Discussion on the Methods of Transferring Debt

The PODS entity's software as described in FIG. 30 and Appendix D will select which legal agreement to use when accepting liability for the debt (novation [FIG. 3-1 through FIG. 3-6], guarantor [FIG. 4-1 through FIG. 4-6] or step-in entity [FIG. 5-1 through FIG. 5-6]) based on data inputs which may include the financial status of potential clients (i.e., Debtor/Seller), the regulations and laws in a specific state, and other business interests. lithe PODS entity's computer system determines that Medicaid, charity care or a private grant is available (see: Calculation Method #11—Charity Care Method) then the only agreements that may be used to accept the debt liability is via being the "Guarantor" [FIG. 4-1 through FIG. 4-6] or the "step-in entity" [FIG. 5-1 through FIG. 5-6]. The reason for this is because if the PODS entity accepted novation of the debt [FIG. 3-1 through FIG. 3-6], it could not benefit from the Medicaid, charity care or private grant that is intended for the patient. In short, if PODS acts simply as the "primary guarantor" [FIG. 4-1 through FIG. 4-6] or the step-in entity [FIG. 5-1 through FIG. 5-6] these programs (i.e. charity care, private grant) to cover or reduce the bill still exist as the natural person (a/k/a patient) may still apply for the grants.

The methods of transferring debt include novation, acting as the guarantor or acting as the step-in entity. Each method has benefits to its implementation and drawbacks to its implementation depending on the circumstances. Below, will detail which implementation is best based on a limited number of circumstances.

A. Novation

Transferring debt liability by way of novation works best in certain situations. One situation is when the Seller wants to be free of all liabilities associated with the debt in exchange for payment. This becomes important for issues like credit ratings, mortgage applications, settling an estate after a death and the like. This is also important for sales in that people would rather be rid of all the liabilities in exchange for payment than face the possibility of negative consequences if the debt settlement between the PODS entity and the provider/creditor is not handled well.

The second situation is a provider/creditor that does not want to settle the debt at a reduced amount. The reason novation works in this circumstance is because the PODS entity can take legal actions, regulatory actions and other actions without fear of harm to the patient and/or guarantor in terms of being named in a lawsuit or suffering other negative consequences. Stated another way, the PODS entity can take any action(s) it desires without fear of the patient and/or guarantor being entangled in the unpleasantness or having the patient\Debtor take legal action against the PODS entity from the damages the patient\Debtor suffered as a result of being caught-up in the dispute.

The third situation when this method is best suited is when the debt is for an out-of-network provider or is for a denial of insurance coverage and therefore becomes patient responsibility.

B. Guarantor and Step-In Entity

Transferring debt liability by acting as the guarantor or step-in entity works well when the patient is near the poverty line or when a provider/creditor denies a transfer via novation. Providers offer charity care (patient financial assistance) to people who cannot afford to pay their debt. Providers have different formulas for determining if a patient qualifies for charity care. These formulas include 150% above the poverty rate and an income/debt ratio that is calculated based on the patient's income, assets and the amount of debt owed.

There are two distinct advantages to using the guarantor or step-in entity method of transferring debt. First, charity care is still an option as the patient is still technically responsible for the bill. The PODS entity may apply for charity care and the result may be a reduced bill based on a charity care grant. This further assist the patient, over the novation method of transferring debt, because the fee the patient/Seller pays the PODS entity may be reduced based on an anticipated debt reduction based on the charity care grant.

This method is also best suited when the debt is for care that was received by an in-network provider or the Seller is eligible for charity care.

Discussion on Novelty and Technological Improvement:

This disclosure, and the software, process, and system in which the debt liability is transferred, contains new patentable matter and technological improvements in its implementation. Some of the novelties include i) The system, software and process employed to determine the type of agreement to be used [FIG. 3-1 through FIG. 3-6—alternative embodiments in FIG. 4-1 through FIG. 4-6 and FIG. 5-1 through FIG. 5-6] and the process and techniques by which the transfer is implemented [FIG. 30, Appendix D] and ii) The calculations and software used are unique to transferring debt liability in an effort to profit from buying debt.

Implementation of Debt Transfer:

There are various processes to transfer patient/Debtor liability to the PODS entity; best practices for these methods change based on the situation (i.e. guarantor vs novation vs payer implemented method of debt transfer).

The manner in which to implement the transfer of the debt is outlined in the flowchart [FIG. 30] and computer code to make the computerized implementation is described in Appendix D.

The Steps are as Follows:

Step 1: [FIG. 30 item 3000] Seller wants to sell/transfer the debt to PODS entity and PODS entity wants to accept the debt liability based on a defined price paid to PODS entity.

Step 2: [FIG. 30 item 3002] When the Seller submits the materials requested but the PODS entity, the PODS entity will investigate with the Seller or the patient's payer to determine if the patient had a form of health insurance (a/k/a payer) and if so, does the patient's payer implement a transfer of debt methodology for the patient responsibility portion of the debt, like that described in the "Payer Implementation of Debt Transfer?" This may also be an automated process by tracking the payers that do implement a debt transfer policy in their plan documents.

If the patient is not covered by a payer that implements a method similar to the "Payer Implementation of Debt Transfer" as described in this disclosure, then proceed to FIG. 30 item 3008. If the patient is covered by a payer that implements a method similar to the "Payer Implementation of Debt Transfer" as described in this disclosure, then proceed to FIG. 30 item 3031.

Step 3: [FIG. 30 item 3031] the PODS entity's software [Appendix D] will use a computer algorithm to determine which agreement [FIG. 3-1 through FIG. 3-6—alternative embodiments in FIG. 4-1 through FIG. 4-6 and FIG. 5-1 through FIG. 5-6] is best suited for its needs. The computer algorithm is updated based on patient financial status, case law and business decisions and will be updated as business decisions and case law change. The Seller will execute the agreement to transfer the debt liability to the PODS entity. Note: execution of the agreement may be via an electronic signature/consent agreement or a written signature.

Step 4: [FIG. 30 item 3034] The PODS entity will then notify the provider/creditor of the transfer of the patient's/Debtor's medical debt to the PODS entity. One reason to send notification of the debt transfer is to ensure that the provider/creditor does not have a non-transfer policy and if the creditor/provider does, to provide a legal argument to overcome the policy if the provider/creditor objects to the debt transfer. Notes: i) if the PODS entity is acting as a step-in entity [FIG. 5-1 through 5-6], then there is no need to send correspondence. ii) When sending the notice, the PODS entity should send a check with a nominal payment to indicate a contract by the legal theory of contract by assent and/or constructive knowledge.

If a novation agreement was used [FIG. 3-1 through FIG. 3-6], then the PODS entity will send notice to the creditor that novation has occurred. Best practices is to obtain a signature with the notice to the creditor [FIG. 6E]. Alternative implementation includes sending notification like FIG. 6D, with proof of mailing/faxing/emailing, as these notifications bind the creditor to the transfer of debt by the legal theory of assent. Further, by sending a nominal payment along with the letter [FIG. 6D] the PODS entity is building a case for contract by assent and/or contract by constructive knowledge.

If a guarantor agreement was used [FIG. 4-1 through FIG. 4-6], then the PODS entity will send notice to the creditor that PODS entity is the primary guarantor of the debt. Best practices is to obtain a signature with the notice to the creditor [FIG. 7E]. Alternative implementation includes sending notification like FIG. 7D, with proof of mailing/faxing/emailing, as these notifications bind the creditor to the transfer of debt by the legal theory of assent. Further, by sending a nominal payment along with the letter [FIG. 7D] the PODS entity is building a case for contract by assent and/or contract by constructive knowledge.

Step 5: [FIG. 30 item 3035] If the provider does not object to the transfer, then the go to Step 8. If the provider does object to the transfer, then the go to Step 6.

Step 6: [FIG. 30 item 3036] If the provider does object to the transfer then the PODS entity will have to determine if current case law supports that the transfer was a proper legally binding transfer or not. If the PODS entity determines there is a legally binding transfer of debt, then the PODS entity ignores the provider/creditor's rejection. Then continue to Step 7.

Step 7: [FIG. 30 item 3038] If the PODS entity determines there is not a legally binding transfer of debt via novation, then the agreement [FIG. 3-1 through FIG. 3-6] will default to that of a guarantor agreement [FIG. 4-1 through FIG. 4-6] per the clause in FIG. 3-2 item 124, or to a step-in entity [FIG. 5-1 through 5-6] agreement based on the clause in FIG. 3-2 item 124. Continue to Step 8.

Step 8: That is the end of the transfer of debt implementation [FIG. 30 item 3080]. Begin working the case.

Step 9: [FIG. 30 item 3008] Use the non-payer implementation. Go to step 10.

Step 10: [FIG. 30 item 3010] The PODS entity's software [Appendix D] use a computer algorithm to determine which agreement [FIG. 3-1 through FIG. 3-6—alternative embodiments in FIG. 4-1 through FIG. 4-6 and FIG. 5-1 through FIG. 5-6] is best suited for its needs. The computer software is updated based on patient financial status, case law and business decisions and will be updated as business decisions and case law change. The Seller will execute the agreement to transfer the debt liability to the PODS entity. Note: execution of the agreement may be via an electronic signature/consent agreement or a written signature.

The PODS entity will then notify the provider/creditor of the transfer of the patient's/Debtor's medical debt to the PODS entity. One reason to send notification of the debt transfer is to ensure that the provider/creditor does not have a non-transfer policy and if the creditor/provider does, to provide a legal argument to overcome the policy if the provider/creditor objects to the debt transfer. Notes: i) if the PODS entity is acting as a step-in entity [FIG. 5-1 through 5-6], then there is no need to send correspondence. ii) When sending the notice, the PODS entity should send a check with a nominal payment to indicate a contract by the legal theory of contract by assent and/or constructive knowledge.

If a novation agreement was used [FIG. 3-1 through FIG. 3-6], then the PODS entity will send notice to the creditor that novation has occurred. Best practices is to obtain a signature with the notice to the creditor [FIG. 6C]. Alternative implementation includes sending a notification like FIG. 6B, with proof of mailing/faxing/emailing, as these notifications bind the creditor to the transfer of debt by the legal theory of assent.

If a guarantor agreement was used [FIG. 4-1 through FIG. 4-6], then the PODS entity will send notice to the creditor that novation has occurred. Best practices is to obtain a signature with the notice to the creditor [FIG. 7C]. Alternative implementation includes sending a notification like, FIG. 7B, with proof of mailing/faxing/emailing, as these notifications bind the creditor to the transfer of debt by the legal theory of assent.

Step 11: [FIG. 30 item 3014] If the provider does not object to the transfer, then the go to Step 14. lithe provider does object to the transfer, then the go to Step 12.

Step 12: [FIG. 30 item 3016] lithe provider does object to the transfer then the PODS entity will have to determine if current case law supports that the transfer was a proper legally binding transfer or not. If the PODS entity determines there is a legally binding transfer of debt, then the PODS entity ignores the provider/creditor's rejection. Then continue to Step 13.

Step 13: [FIG. 30 item 3020] If the PODS entity determines there is not a legally binding transfer of debt via novation, then the agreement [FIG. 3-1 through FIG. 3-6] will default to that of a guarantor agreement [FIG. 4-1 through FIG. 4-6] per the clause in FIG. 3-2 item 124, or to a step-in entity [FIG. 5-1 through 5-6] agreement based on the clause in FIG. 3-2 item 124. Continue to Step 14.

Step 14: That is the end of the transfer of debt implementation [FIG. 30 item 3080]. Begin working the case.

Payer Implementation of Debt Transfer:

Payers are in a unique situation to ensure the patient/Debtor may transfer the patient responsibility portion of the debt. The reason is the payer's plan documents become a binding agreement between the provider and the payer; the patient/Debtor benefits from the provider-payer agreement.

To ensure the patient/Debtor may transfer the debt, the payer should implement Step A, Step Band Step C below. Though all three (3) steps (Step A, Step B, Step C) is a best practices approach, the payer is safe implementing just one step. Full guidance on this point of how many steps must be implemented will be instructed based on case law.

Step A—Provider Notification

To ensure the implementation methods described in Section VI entitled "Transferring the Debt" meets legal requirements and are enforceable in court, payers, unions, groups and individuals will implement a notice to a provider. On all membership cards there will be notice to the provider. An exemplary notice would read "The patient reserves right to novate or transfer patient responsibility portion of the claim."

Step B—Plan Documents

A payer will include a section on "patient responsibility" in the payer's plan documents. This section of the plan documents will indicate that the patient (a/k/a member or insured) has the right to novate or otherwise transfer the patient responsibility portion of the medical bill.

Exemplary language:

Section I—Patient Responsibility Portion of the Claim: The insured reserves the right to novate otherwise transfer the patient responsibility portion of the claim. Novate or transfer of the patient responsibility portion of the debt may be made solely by notice from the person/entity that assumed the debt to the provider.

Step C—Payment with Notice

If a payer remits payment directly to the provider for the portion of the bill that is the payer's responsibility, the payer's computer system will include a statement on the remittance notice stating that by cashing the check (or notice accompanying an electronic payment), the provider agrees to allow the patient/Debtor to transfer the patient responsibility portion of the debt owed.

Exemplary Language:

By cashing this check, provider [provider name] agrees to allow the patient/Debtor to novate or otherwise transfer the patient responsibility portion of the bill/debt. Novation or transfer of the patient responsibility portion of the debt may be made/effected solely by notice from the person/entity that assumed the debt to the provider.

Note: if this implementation fails for any reason the agreement between the Seller and PODS entity will default to that of a step-in entity as described in the paragraph entitled "Discussion on Step—In Entity & Guarantor Implementation" based on the clause [FIG. 3-2 item 124; or FIG. 4-2 item 124 if a guarantor agreement is used] in the Seller/PODS agreement.

Step D—Transfer

Step A through C detailed above layout a method to allow the patient/Debtor to transfer the debt without the provider having to acknowledge their consent to the transfer. The PODS entity must notify the provider/creditor of the novation or transfer [FIG. 6D, FIG. 6E, FIG. 7D, FIG. 7E] once the Seller and PODS entity have agreed on the transfer.

VII. Working the Debt

Bonded: It would be beneficial if The PODS entity was bonded for the following reasons. i) The purpose for this is to ensure that the Debtor's money is not stolen by unscrupulous people. ii) Case law has not been established for this invention. In order to show a court that the PODS entity is sincere in having the debt transferred to it, the PODS entity will be bonded proving to the court that all actions are in good faith.

Financial Reserves: Insurance companies must maintain financial reserves to ensure claims payments as outlined by state and federal laws. Because case law and governmental regulations have not been established, the PODS entity should maintain financial reserves in the amount of several months of settlements to ensure provider bills will be settled. This is in an effort to show a court of law that the PODS entity is credible and acting in good faith.

When to begin working the debt: The PODS entity must be alert for negative credit ratings or lawsuits based on the age of the debt. To ensure no negative consequences are suffered, the PODS entity takes action prior to a provider/creditor's historical timeline for employing negative actions. To assist with this, the following computer code is used:

Variables:
Note: When determining the difference in dates or days between dates, the dates being compared are converted to their Julian days, then the match is applied to those Julian dates.

$days_from_dos is a computer variable. It is the result of calculating the number of days between today's date and the date of service by converting the variable to its Julian day. Example: if today was 1/30/15 and the date of service was 1/1/15, then the variable $days_from_dos would equal 29. The data field in FIG. 19A through FIG. 19C that would be used is the DOS data field.

To Determine the Number of Days Before a Credit Rating is Affected:

$avg_days_negative_credit is a computer variable. It is the result of averaging the number of days between the date of service (DOS) and the date of that the provider/creditor filed a negative credit rating (DNCR) on its patients for every record where in Table #1 [FIG. 19A through FIG. 19C]:

Step 1 the provider name in FIG. 19A through FIG. 19C matches the inputted provider name.

Step 2 the data in the TYPE column [FIG. 19C] matches "CREDIT".

Step 3 average the number of days between the DOS and the DNCR variables by adding the total number of days for all the records matched in the query, by the number of records used.

Step 4 the result of this calculation will allow the PODS entity to forecast when the specific provider will effect the member's credit rating.

In an alternative embodiment, the amount owed "BAL in FIG. 19A" may also be matched during the data query allowing the PODS entity to determine with greater accuracy when the event will occur based on the outstanding balance owed.

To Determine the Number of Days Before a Lawsuit is Filed:

$avd_days_lawsuit is a computer variable. It is the result of averaging the number of days between the date of service (DOS) and the date of that the provider/creditor filed a negative credit rating (DNCR) on its patients for every record where in Table #1 [FIG. 19A through FIG. 19C]:

Step 1 the provider name in FIG. 19A through FIG. 19C matches the inputted provider name.

Step 2 the data in the TYPE column [FIG. 19C] matches "LAW".

Step 3 average the number of days between the DOS and the DNCR. variables by adding the total number of days for all the records matched in the query, by the number of records used.

Step 4 the result of this calculation will allow the PODS entity to forecast when the specific provider will file a lawsuit.

In an alternative embodiment, the amount owed "BAL in FIG. 19A" may also be matched during the data query allowing the PODS entity to determine with greater accuracy when the event will occur based on the outstanding balance owed.

The steps listed above "To Determine the Number of Days Before a Lawsuit is Filed" may be used to determine how long before the provider will not treat the patient (variable NOTREAT [FIG. 19C]; how long before a collection company will call or send a dunning notice (variable OUTCOL or INCOL [FIG. 19C]). To accomplish this, the PODS entity would query the data using the variables "INCOL" or "OUTCOL" or "NOTREAT" in place of "LAW" in Sep #2.

$call_action is a procedure call determined by the PODS entity. The procedure call may be a routine to i) send payment and settlement terms that day. ii) file a lawsuit against the provider. iii) have a lawyer contact the provider/creditor to stop any action while the debt is resolved. iv) do nothing based on the amount of the outstanding debt.

The variable "$days_from_dos" is computed by subtracting the date of service "DOS" from today's date.

If (($days_from_dos+30)>=($avg_days_negative_credit)) or (($days_from_dos+30)>=($avg_days_negative_credit))
{
$call_action;
}
end of procedure above The PODS entity will begin working the debt after it is finished obtaining insurance reimbursement and has determined that all insurance companies have met their responsibilities irrespective if a denial is given or not. The reasons for this include i) if the debt is lowered to the amount covered by the patient's deductible, then the insurance company does not have to pay any portion of the claim. Because the insurance payment would then not be paid, the provider will likely settle the debt at a higher amount of money thereby causing the PODS entity to lose money. ii) If the settlement occurs after the insurer(s)' payment, then all amounts being settled, or refunded, are considered "patient responsibility" because providers are more concerned with settling the outstanding balances on the accounts than crediting and debiting insurance companies and patients based on settlement amounts.

Working the debt: First, the PODS entity would have the patient execute a HIPAA consent form so that the PODS entity could request data and discuss the claims with the payer, provider, or other entity. Note: this would generally be done when the agreement between the Seller and the PODS entity is executed but may also be done later.

Second, the PODS entity would seek insurance coverage and, if needed, appeal any denial of coverage with the payer(s) responsible for the debt. An outline of how to appeal a payer is found in Appendix B, which is incorporated herein by reference.

Third, the PODS entity would seek to settle the outstanding amount with the provider/creditor. An outline of how to settle an outstanding bill is found in Appendix A, which is incorporated herein by reference.

VIII. Methods to Settle the Outstanding Balance Owed to the Provider/Creditor Settlement Method #1:

Payment is sent to an authorized person (e.g., director, VP, CFO) at the provider facility using the settlement amount determined by the PODS entity [FIG. 9A] or an automated amount may be implemented based on one of the calculation methods [FIG. 9A], with a letter stating that the enclosed is full payment for the debt and by cashing the check, it is mutually agreed that this is payment in full.

Exemplary language: "Based on the [variable: identify a reason for disputing the bill] identified and desire to settle the debt, we have enclosed payment in the amount of $1,500 (check #343) for account #7362. By cashing this check it is mutually agreed that this is payment in full and the balance will be written off You further agree to release and hold PODS entity harmless for any legal torts or other causes of action. If these terms are not acceptable, please return the check and [PODS entity] will seek to redress this matter in a different manner."

In this implementation there is a possibility that the provider/creditor will initiate a lawsuit to collect the monies owed. This is anticipated in a number of cases and is why a small amount of money is set aside (Risk.%) on all cases to cover the cost of legal fees for the small number of cases that are litigated.

Settlement Method #2:

When the PODS entity is working the debt as described in Section VII, it will contact an authorized person at the provider/creditor's office (e.g., director, VP, CFO) via a letter, email, phone call, facsimile or other, to assert the reason the provider should allow a discount. At this time, offer and acceptance terms are agreed to between the PODS entity and the provider/creditor.

If an agreement is reached, a. formal written agreement will be sent with payment to the authorized person at the provider/creditor.

Exemplary language: "Based on the [variable: identify a reason for disputing the bill] identified and our discussions dated [date] it is mutually agreed that a payment in the amount of $11,200 will be "payment in full" and all balances will be written off for account #4332 and account #7473. You further agree to release and hold PODS entity harmless for any legal torts or other causes of action. Please sign and date below and return this document."

If an agreement cannot be made between the PODS entity and the provider/creditor, then Settlement Method #1 above will be used.

If the provider/creditor will not accept the settlement offer then the PODS entity will:

Step 1: Have the patient/guarantor dispute any negative credit event with a credit bureau if adverse events are reported to a credit bureau for said charges or hire a law firm to assist the patient/guarantor. Further, the PODS entity will consider helping the patient/guarantor with legal actions against the provider and/or collections company for filing a negative credit rating.

Step 2: If a lawsuit is filed, the PODS entity will supply a legal defense for the PODS entity and the patient/guarantor/Seller. The money for the legal defense is taken from the Risk % pool of money that has been set aside for legal defense.

IX. Medicare and Discounting

Medicare has guidelines that all providers who participate in the Medicare program must follow. Such guidelines include i) a provider may allow a discount to uninsured patients and ii) a provider must try to obtain all deductibles and co-insurances. Similarly, private insurers have "favored nations" clauses. The invention allows the PODS entity to obtain greater reductions from providers because the debt will be owed by a company and not by a "natural person." The greater reduction in the amount owed come from the fact that a settlement on the amounted owed is not dictated by Medicare guidelines therefore, greater bargaining power exists. Further, because the PODS entity is identifying billing errors, the PODS entity may state that it is not "negotiating the bill" but found "billing errors" that allow the amount to be reduced.

X. Post Settlement Data

All data collected, along with the post settlement data which includes the variables STL, DS, M (previously described in this disclosure) and any other variables are entered into the experience rating data table [FIG. 2 element 126] that is stored on readable computer storage medium, in a physical binary structure, for use with future analysis and/or other use.

In addition to the information found on the medical bills, EOBs and settlement data, the PODS entity will also seek dunning letters from collection companies, adverse credit rating reports and information on lawsuits from the Sellers that contact the PODS entity. The PODS entity may also collect the dunning letter information, adverse credit report information and lawsuit information from other sources to ensure the experience data [FIG. 2 element 126] has an adequate amount of data.

XI. Financial Protections

The steps below may also be used by the PODS entity to obtain additional income by charging for the document or action as promised by the entity using the PODS system.

If FIG. 1A-7 item 124 or FIG. 1B-7 item 124, regarding lawsuits, is checked "yes," then additional language [FIG. 3-4 item 130, FIG. 4-5 item 130 or FIG. 5-5 item 130] will be added into the agreement between the Seller/patient and the PODS entity. This language states that the PODS entity will pay for all legal costs if the Seller/patient is named in a lawsuit for the debt specified. Note: the legal language and defense of the Debtor/patient should be standard. This implementation is simply a way to obtain an additional fee.

If FIG. 1A-7 item 126 or FIG. 13-7 item 126, regarding credit repair, is checked "yes," then instructions on how to remove a bad credit mark like that illustrated in [FIG. 10] will be presented via computer software or sent via email (and may be sent via US mail). In an alternative embodiment, the PODS entity could contact the credit bureau and have the negative credit mark removed but the PODS entity would first have to meet the regulatory requirements of a credit repair company. It is because of this that instructions are sent [FIG. 10].

XII. Improvement Over Negotiating Bills

The PODS system is fully automated whereas traditional systems are manually implemented.

Advocacy companies have been negotiating provider bills for a flat fee and on a contingency fee basis. The average contingency fee is 30% of the savings. This means that if the advocacy company saved the Debtor $100, the advocacy company's fee would be $30.

The PODS method described herein is an improvement over the negotiating method because it i) builds in guaranteed financial protections for the Debtor; ii) uses the psychological phenomena of fear of lawsuit or credit that causes a Debtor to want to immediately sell their Debt; iii) uses the documented psychological phenomena of loss to result in a greater profit (e.g., studies have shown that people fear losing the money they have more than they seek the reward of gaining more money. Based on this, the PODS system works based on psychological factors.); iv) it allows the Debtor to be rid of the debt thereby not having to worry about it or spend resources servicing the debt (i.e., dealing with the creditors, collection agencies, credit bureaus, lawyers and other); v) there is no maximum payment limit placed on the PODS entity when there often is with a patient advocacy company; vi) allows for a "known" savings and not an estimated savings at the time of contracting with the entity that is negotiating the bills, vii) companies that negotiate bills are unable to make or sustain profit margins on small bills. The PODS entity can make a sustainable profit margin with bills that have a small outstanding balance, viii) because the debt is purchased, there are no hidden fees so the Seller has better financial protections, ix) A monetary advantage is that the PODS system maximizes its profit by maximizing the Selling Price the Debtor/Seller is willing to pay to settle the debt and the Settlement Price the provider/creditor is willing accept to settle the debt. This delta (difference in the two prices) maximizes the PODS entity's profits, and x) it allows the PODS entity a greater profit as illustrated in these examples:

I. Example: Anne owes $150,000 for a treatment that was denied by Humana®. Anne is willing to pay $88,500 to settle the medical bill but the hospital will accept $20,000. PODS entity's_profits: $68,500. An advocate's fee if the bill had been negotiated (30% contingency fee): $39,000.
  II. Example: Mark owes $30,128 for a neurosurgery bill. He is willing to settle for $20,000. The hospital is willing to settle for $8,000. PODS Entity's profits: $12,000. An advocate's fee if the bill had been negotiated (30% contingency fee): $6,638.
  III. Example: Paul has a $14,000 dental bill from an accident. He is willing to settle the bill for $10,000 and the dentist is willing to accept $7,000. PODS Entity's profits: $3,000. An advocate's fee if the bill had been negotiated (30% contingency fee): $900.

As discussed above, the contingency fees paid to advocacy companies are often capped at a maximum. Example, the patient advocacy or patient billing company will received 30% of the savings up to a maximum of $3,000. These maximums are in place because consumer's often feel cheated when a company takes such a large part of the money. When an entity uses the PODS system, there is no maximum profit cap as the maximum profit is capped solely by the PODS entity's ability to i) obtain a maximum insurance payment, ii) have the debt reduced, iii) maximize the fee the Seller is willing to pay the PODS entity in exchange for accepting liability for the debt.

Another advantage the PODS system has is "double dipping." Specifically, a 2007 Harvard University study stated "Harvard researchers say 62% of all personal bankruptcies in the U.S. in 2007 were caused by health problems—and 78% of those filers had insurance." In such situations it is often the case where the payer denied payment on the claim. This invention allows the PODS entity to have the insurance benefit assigned to it, while it also reduces the balance due.

So how does the PODS entity double dip? Advocacy companies work cases on a contingency fee for a percentage of the recovery. If the medical debt is purchased, the revenue margins increase dramatically. First, have the Seller assign his/her health insurance benefits to the PODS entity, the PODS entity may then seek reimbursement from the payer allowing a 2x (two fold) return on the investment when compared to strictly working the claim on a contingency fee basis. Second, at the same time, there is profit made when negotiating the debt with the provider.

Example:
  Mary has a $40,000 bill from a medical procedure that was denied by the insurance company. An advocacy company that fought the insurance company for reimbursement and won would be paid 30% of the savings, equaling $12,000. If the PODS entity purchased the debt liability at a reduced cost for $25,000, and settled the bill with the provider for $20,000, and fought the payer for the full $40,000, the PODS entity profit would be $45,000. Additional value to the patient is that once they transferred via novation the liability to the PODS entity, they had no more financial exposure, potential bad credit ratings, or other.

While assigning insurance benefits is not new, the difference (or improvement) in some cases is that there are no insurance benefits being assigned. In these instances, the payer denied payment so there is no insurance benefit associated with the claim. Instead, the PODS entity is going to have to create value in the denied claim in order to obtain payment from a payer.

Another improvement over negotiating bills is the Collection Experience Rating. In a negotiating or bill auditing environment, the advocacy company is forced to work with the provider and reach a settlement otherwise the advocacy company and/or patient risks a lawsuit if the Debtor suffers any adverse consequences (i.e., FIG. 20 item 2000 is an exemplary embodiment of a collection company notifying a Debtor that their account has been reported to a credit bureau for being in default). If the debt is novated then the creditor cannot take any negative action against the patient. If the debt is transferred to the PODS entity as a guarantor or step-in entity, then i) the PODS entity will supply a defense for the patient and ii) the Collection Experience Rating system may be employed.

Example: An advocacy company must reach a settlement with the provider to ensure the Debtor does not suffer any adverse consequences. In this same situation, the PODS entity would look at the Collection Experience Rating and determine that the provider's history indicates that the provider does not affect debtors' credit ratings and the provider does not commence legal actions against debtors. In this example, the PODS entity may offer a very small monetary settlement and if the provider does not accept it, then the PODS entity has a statistical basis to conclude that no adverse action will follow. Further, if there is an adverse action, it would be against the PODS entity and not the Debtor.

Another improvement over negotiating bills relates to the legal theory of arbitrary and capricious. If the PODS entity simply determines a settlement amount and sends payment as outlines in Section VIII entitled "Methods to Settle the Outstanding Balance Owed to the Provider/Creditor" then providers/creditors could claim the settlement amounts are arbitrary and capricious. But because the settlement amounts are based determined by mathematical calculations run over experience ratings or Medicare rates, it would be difficult for a provider/creditor to win on the legal theory of arbitrary and capricious.

XIII. Subrogation Calculation

The possibility for subrogation via a/the payer is determined via calculation and variables. When using this implementation, the final results displayed via software would include the potential for monetary gain by way of the payer paying the claim(s) and the final result displayed would be calculated to reflect that.

Mathematical Model #1 for Subrogation Calculation Potential:
  If DEN is "true" then DEN variable is set to "0.50" in the formulas below.
  If DEN is "false" then DEN variable is set to "1" in the formulas below.
  If APL is "true" then APL variable is set to "0" in the formulas below.
  If APL is "false" then APL variable is set to "1" in the formulas below.

$$PFS=(100*(DEN*APL))$$

Note: If DEN is true means there was a denial. If DEN is false means no denial was given. If APL is true means the appeals process has been used. If APL is false means the appeals process has not been used.

Mathematical Model #2 for Subrogation Calculation Potential:
  If DEN is "true" then DEN variable is set to "0.50" in the formulas below.
  If DEN is "false" then DEN variable is set to "1" in the formulas below.
  If APL is "true" then APL variable is set to "0" in the formulas below.
  If APL is "false" then APL variable is set to "1" in the formulas below.
  The "Provider" variable (Table #1 [FIGS. 19A-19C]) is used in conjunction with the DEN and APL variables (Table #1 [FIGS. 19A-19C]) to determine an experience rating with an insurance company's denials for a specific provider. This is based on the fact that insurance companies often target specific providers for denials based on how hard the provider tights, or does not fight, for reimbursement from the payer. The purpose of this algorithm is to determine how likely the PODS entity will be in overturning the insurer's denial of coverage based on historic denial and appeals data.

$$PPS=(((100*(DEN*APL))*(Provider(WV_{100}))))$$

XIV. Third Party Issues

Providers, payers, and other entities are instituting polices and/or declaring that they do not work or interact with third parties. These entities will only work with the patient. These entities do so because it ensures the entity's relationship with the patient. Also, when it comes to reducing a medical bill, the entities know that they will settle the bill for more money from a lay person (a.k.a. the patient) than from a professional. Because of this, they alienate the third party and declare that they will only work with the patient.

Because the PODS entity has accepted novation, or is acting as the guarantor, or as step-in entity, or has allowed the debt to be transferred to the PODS entity, the issues of only working with third parties has been alleviated.

XV. Estimated Selling Point

The result of the calculations for the Estimated Selling Point result in the "Selling Price."

When working with the Debtor over the Selling Price or if the medical bills are on an auction site like E-bay, then there are two computerized mathematical models that will be employed to determine the amount for which Debtor is willing to sell the bill to the PODS entity. They are the "Calculated Estimate of Seller's Selling Point" (herein "CESSP") and the "Experience Rating of Seller's Selling Point" (herein "ERSSP"). Variables for use in such calculations include:
  USID refers to the unique id in the data table for the Debtor
  BAL refers to the original outstanding balance of the bill
  SOLD refers to the price for which the Debtor sold the medical bill
  ZIP refers to the average annual household income for the Debtor's zip code based on U.S. Census data. The annual income will be converted into a weighted variable where high income zip codes will cause the calculation to result in a higher estimated Selling Price whereas a low income zip code would result in a lower estimated Selling Price.
  G refers to gender
  CR refers to the Debtor's credit rating (i.e., Transunion, Experian, Equifax, FICO score). If the Debtor has a good credit rating then the variable for good create ratings will cause the calculation to result in a higher estimated Selling Price whereas a low credit rating would result in a lower estimated Selling Price. The reason is that people with good credit are incentivized to keep a good credit rating and therefore, are likely to pay more to the PODS entity.
  WV is a weighted variable determined by the entity using the PODS system.
  PPM refers to a predetermined profit margin as determined by the PODS entity.
  Age of Bill is converted in a result where the older the bill, the newer the bill, the higher estimated Selling Price whereas an older bill would result in a lower estimated Selling Price.
  Some of the variables above, such as ZIP, represent demographics of the Debtor.
  Other variables above, such as G and CR represent personal information about the Debtor.

Calculated Estimate of Seller's Selling Point:

Step 1—Computer software will be used to produce a mathematical model of the CESSP value. The computer software will run a formula [FIG. 2 element 130] in the computer's random access memory using the following variables and mathematical operand. If an experience rating for the provider exists then the computer will run software with the following instruction set:

$$CESSP=(TOTAL\ ERA*CR(WV_{110})*ZIP(WV_{111})\\*PPM*(Age\ of\ Bill(WV_{112})))$$

Step 2—If an experience rating for the provider does not exist then the computer will run software with the following instruction set:

$$CESSP=(GA*CR(WV_{120})*ZIP(WV_{121})*PPM)$$

Step 3—Experience Rating of Seller's Selling Point:

A data table (a physical binary structure stored on computer readable medium) that is stored on computer readable medium [FIG. 2 element 142] will be stored for every Debtor/Seller/patient that uses the system. When a Debtor/Seller/patient agrees to sell the debt to the PODS entity, the ERSSP data table will be updated with the terms of the sale so that an experience rating for the Debtor/Seller/patient may be determined in the future. Further, the Debtor/Seller/patient's zip code and gender are also stored so that predictive modeling may be used in the future based on these variables.

TABLE #4

| USID-Debtor | BAL | SOLD | G | ZIP |
|---|---|---|---|---|
| 1-Mark Harris | $323 | $180 | male | 08051 |
| 2-Mark Harris | $12,121 | $6,232 | male | 08051 |
| 3-Mark Harris | $4,643 | $2,411 | male | 08051 |
| 4-Robert Black | $6,233 | $4,543 | male | 08051 |
| 5-Robert Black | $3,234 | $2,732 | male | 08051 |

If an experience rating for the Seller/Debtor/patient does exist then the computer will run software with the following instruction sets. Every record in the ERSSP [FIG. 2 element 142] where the USID is for the Debtor/Seller/patient currently selling the bill will be copied into a temporary data table. Then computer software will be run over each record in the data with the following instruction set ((SOLD/BAL) *100); each result will then be stored in Random Access Memory. Once the percentage for which the bill was sold is calculated for each record, all results will be averaged and stored in random access memory in the variable AVG-SOLD %. Stated another way, AVG-SOLD % represents the average reduction the PODS entity took to accept the liability for the bill. Example, if the bill was $1,000 and the AVG-SOLD % was 25%, then the Selling Price would be $750.

Calculation #1
Sample Computer Code:

If $((BAL*(AVG\text{-}SOLD\ \%))<(TOTAL\ ERA*PPM))$
then $(ERSSP=(TOTAL\ ERA*PPM))$ Else $ERSSP=(BAL*(AVG\text{-}SOLD\ \%)$ Calculation #2
Sample computer code:

If $((BAL*(AVG\text{-}SOLD\ \%))<((GA*PPM))$ then
$(ERSSP=(GA*PPM))$

Else $ERSSP=(BAL*(AVG\text{-}SOLD\ \%))$

No matter which Estimated Selling Point calculation is used, the PODS entity it will implement an error algorithm where the offer to the Seller/Debtor/patient must always be equal to or greater than the outstanding amount plus operating costs, plus a profit margin and plus a Risk %, less any anticipated insurance payments. This error check helps to ensure the PODS entity's financial viability.

app C is an alternative method and software to determine a Selling Price based on specific data variables, predictive analytics and algorithms.

XVI. Credit Repair

When a Debtor wishes to repair their credit score, also commonly referred to as a FICO score, the Debtor may sell the debt liability to the PODS entity. As discussed earlier in this disclosure, the PODS entity will produce a transformative document stating that the PODS entity is liable for the debt [FIG. 6A, FIG. 7A or FIG. 8] and provide instructions on how to fix it [FIG. 10].

The Debtor takes the document produced by the PODS entity and sends it to the credit rating bureau (like Transunion®, Equifax®, Experian®) with a dispute letter stating that the negative credit mark is no longer the responsibility of the Debtor, but that of the PODS entity and to mark the debt as paid.

If the credit rating bureau (i.e., Transunion, Equifax, Experian) refuses to mark the debt as paid prior to the PODS entity settling the debt with the provider, the Debtor may request that the credit rating bureau make a notation on the Debtor's credit report that the debt has been transfer to the PODS entity. Such a notation on a credit report (i.e., FIG. 20 element 2000) can assist Debtors as companies reviewing credit reports for hiring purposes, new loan purposes or other will see that the Debtor made proactive steps to settle the debt and is not trying to simply run away from the debt without paying.

Note: If a novation agreement is used, the debt is that of the PODS entity. if a guarantor agreement or Step-in Entity agreement is used, then the patient does still have liability for the debt but may argue that they debt is truly that of the PODS entity's.

XVII—A. How the PODS System is Used by a Debtor

Figure 13B:
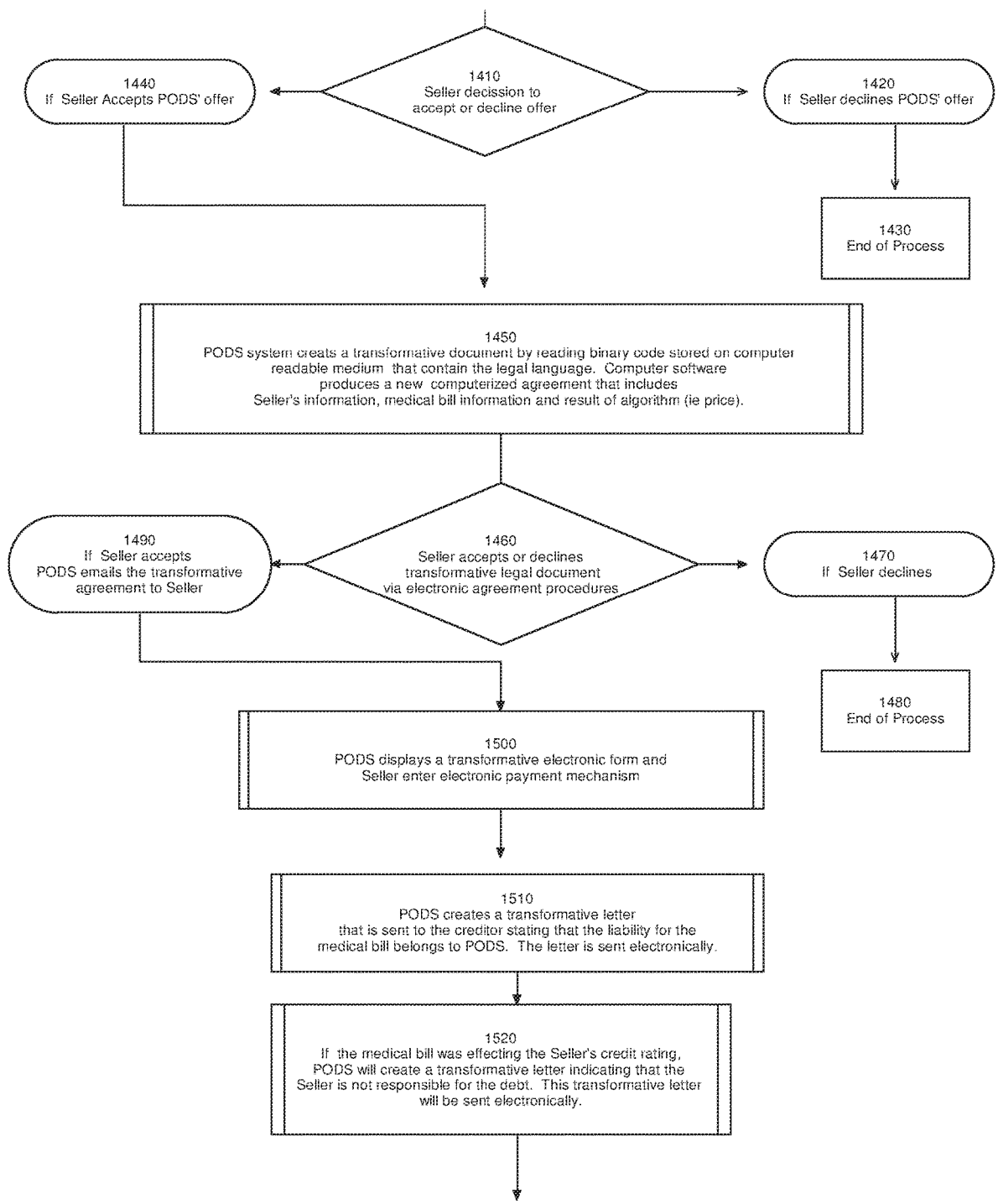

In an exemplary embodiment as illustrated in FIG. 13A through FIG. 13C, the invention includes computer implemented methods, mathematical models and algorithms, computer systems, and computer readable storage media including instructions that when processed by a processor enable the processor to implement methods for an entity using the PODS system to realize a financial gain by purchasing debt at specific price and then obtaining insurance reimbursement and/or obtaining a lower Settlement Price with the provider/creditor an a timely manner based on the provider's/creditor's anticipated negative events (e.g., affecting credit ratings, starting lawsuits, etc). In exemplary embodiments, such method includes the steps of:

the Seller accessing the software via the Internet or PODS network [FIG. 13A element 1310];

the Seller enters information into software via an application programming interface [FIG. 13A element 1320; FIG. 1A-1 through FIG. 1A-7 or FIG. 1B-1 through FIG. 1B-7];

the Seller uploads a scanned image of the medical bill and insurance statement (EOB) to the PODS computer system [FIG. 13A element 1330];

the PODS computer system stores the entered information in a physical binary structure that is stored on a computer readable storage medium as a PODS database [FIG. 13A element 1340] Note: the information may also be stored in the computer's random access memory if enough memory exists;

the PODS computer system then scans the medical bill and EOB and populates the PODS database with this data [FIG. 13A element 1340]; and the PODS computer system executes queries that contain mathematical models and algorithms over the data stored in the PODS database and results are produced [FIG. 13A element 1350]. Automated actions are then determined and made based upon these results.

In the exemplary embodiment, execution of the mathematical models and algorithms [FIG. 2 element 130] includes executing computer code that processes historical data of past settlements [FIG. 2 element 126] in order to predict the provider's Settlement Price. This query returns a few different results (each based on a different mathematical model) so that the PODS computer system may evaluate the predicted Settlement Price in different ways. Execution of the mathematical models and algorithms also includes executing computer code that processes the data inputted by the Seller to predict the provider's Settlement Price. This second method is strictly a mathematical model [FIG. 2 element 130] and does not use historic data. Based on the processing of the computer algorithms, a mathematical model and result is determined. The mathematical result is compared to pre-determined criteria to determine if the PODS computer system desires to purchase the debt liability based on pre-established criteria. The queries and calculations are outlined in Section IV. Entitled "Transformative Analysis of the Data."

At element 1360 [FIG. 13A], the PODS computer system processes the estimated Selling Price by the methods outlined in Section XV—entitled "Estimated Selling Point." The PODS system then returns a result determining whether or not the PODS computer system wants make an offer to purchase the debt or not. If the PODS computer system does not want to make an offer to purchase the debt, it will state this on the computer display screen [FIG. 13A element 1370] and the process ends [FIG. 13A element 1380]. However, if the PODS computer system does want to make an offer to purchase the debt [FIG. 13A element 1390], an appropriate indication will be displayed on the computer display screen [FIG. 13A element 1400, FIG. 15]. Note: FIG. 15 is populated with the Selling Price; it is important to note that the decision to make an offer is based on the Settlement Price being lower than the Selling Price and that the Selling Price is what is used in making an offer to the Seller/Debtor [FIG. 15].

The Seller/Debtor may then choose to accept or decline the offer [FIG. 13B element 1410, FIG. 15]. If the Seller declines the offer [FIG. 1313 element 1420], then that is the end of the process [FIG. 13B element 1430]. If the Seller chooses to accept the offer [FIG. 13B element 1440], then the PODS computer system will query the physical PODS database for the legal language and then make a transformative document inputting the Seller's information, the medical bill information, and the purchase price that was determined by the mathematical models [FIG. 13B element 1450]. The transformative document [e.g., FIG. 3-1 through FIG. 3-6; FIG. 4-1 through FIG. 4-6, or FIG. 5-1 through FIG. 5-6; FIG. 2 element 120] will be populated with the Seller/Debtor details; details of the debt; the Selling Price will be inserted at FIG. 3-1 item 120, FIG. 4-1 item 120 or FIG. 5-1 item 120 and all other fields populated and displayed via a computer display [FIG. 13B element 1460], and the Seller must decide whether he/she wants to decline or accept the offer to purchase the debt made by the PODS computer system. If the Seller/Debtor declines the offer (transformative documents containing legal language) [FIG. 13B element 1470], then that is the end of the process [FIG. 13B element 1480]. If the Seller/Debtor does accept the offer made by the PODS computer system [FIG. 13B element 1490], then the PODS computer system will display payment information [FIG. 13B element 1500]. This will be a software display where the Seller may enter his/her credit card or electronic checking information.

After payment is made by the Seller/Debtor, the PODS computer system will create a transformative letter (e.g., as illustrated in FIG. 6A through FIG. 6C, FIG. 7A through FIG. 7C, or FIG. 8) that will be sent electronically to the creditor (the letter may also be faxed or mailed) stating that the user of the PODS computer system has assumed the liability for the debt [FIG. 13B element 1510]. If the Seller's credit rating was affected by the outstanding medical bill, then the PODS computer system will generate a transformative letter by inputting specific data from the Seller's contact information and pre-determined contract language and email this letter to the Seller, or to the credit bureau (i.e. TransUnion®, Equifax®, Experian®) [FIG. 1313 element 1520].

In a fully automated embodiment [FIG. 13C element 1530], the PODS computer system would commence with the error checking calculations as described in Section IV. entitled "Transformative Analysis of the Data." Upon completion, the PODS computer system would implement the Calculation Methods To Determine an Estimated Settlement Price as described in Section IV. entitled "Transformative Analysis of the Data" to determine a final Settlement Price. After the processing of calculations the PODS computer would automate the settlement of the outstanding debt with the provider by a method as described in Section entitled "Methods to Settle the Outstanding Balance Owed to the Provider/Creditor."

In an embodiment that is automated but employs manual steps [FIG. 13C element 1530], the PODS entity will utilize its skill to i) seek reimbursement from a payer, negotiate with the creditor to accept a lower offer, obtain a grant or charity care to help lower or pay the medical bill, audit the medical bill for errors, identify another payer (i.e. malpractice carrier, homeowners), and/or find other ways to lower the debt [FIG. 13C element 1530]. These methods are outlined in Section VII, entitled "Working the Debt."

The results of the Seller's/Debtor's payment price and demographic details are entered into the PODS database [FIG. 13C element 1540, FIG. 2 element 142]. The results of the settlement of the medical debt are entered into the PODS database [FIG. 13C element 1550, FIG. 2 element 126] and process is then complete [FIG. 13C element 1560].

XVIII-B. How the PODS System is Implemented as a Service Bureau

This disclosure has been directed at how an entity may profit from implementing the PODS system. This Section XVIII-B, entitled "How the PODS System Is Implemented as a Service Bureau" describes how the PODS system may be implemented as a service bureau and used by the Debtor/Seller/patient to obtain a reduction on their outstanding debt. Absent is a third party accepting liability of the outstanding debt liability then working and settling said debt liability.

Figure 17:
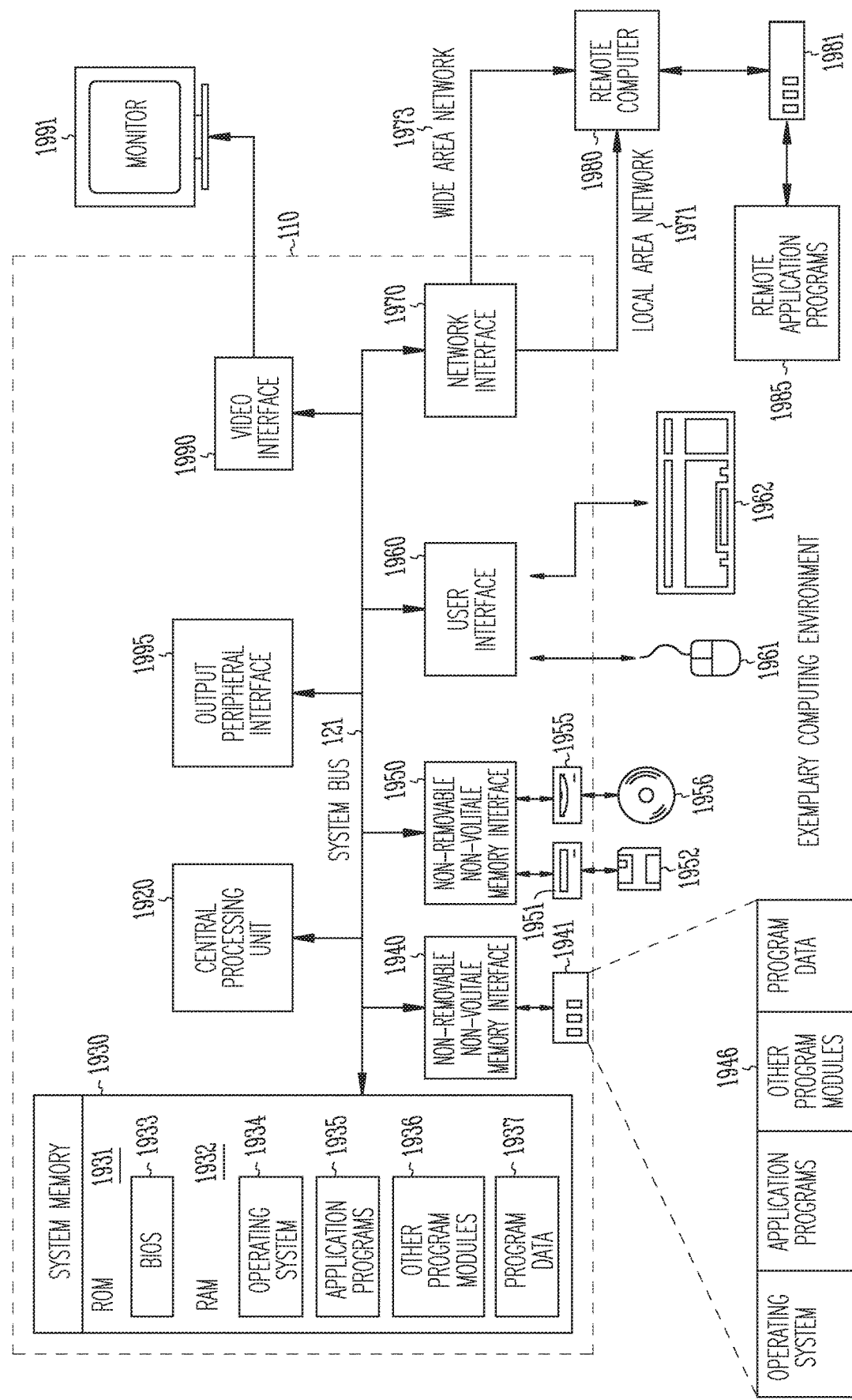
FIG. 17 is a sample of a specific device/computing environment used in the system of FIG. 2.
Figure 18:
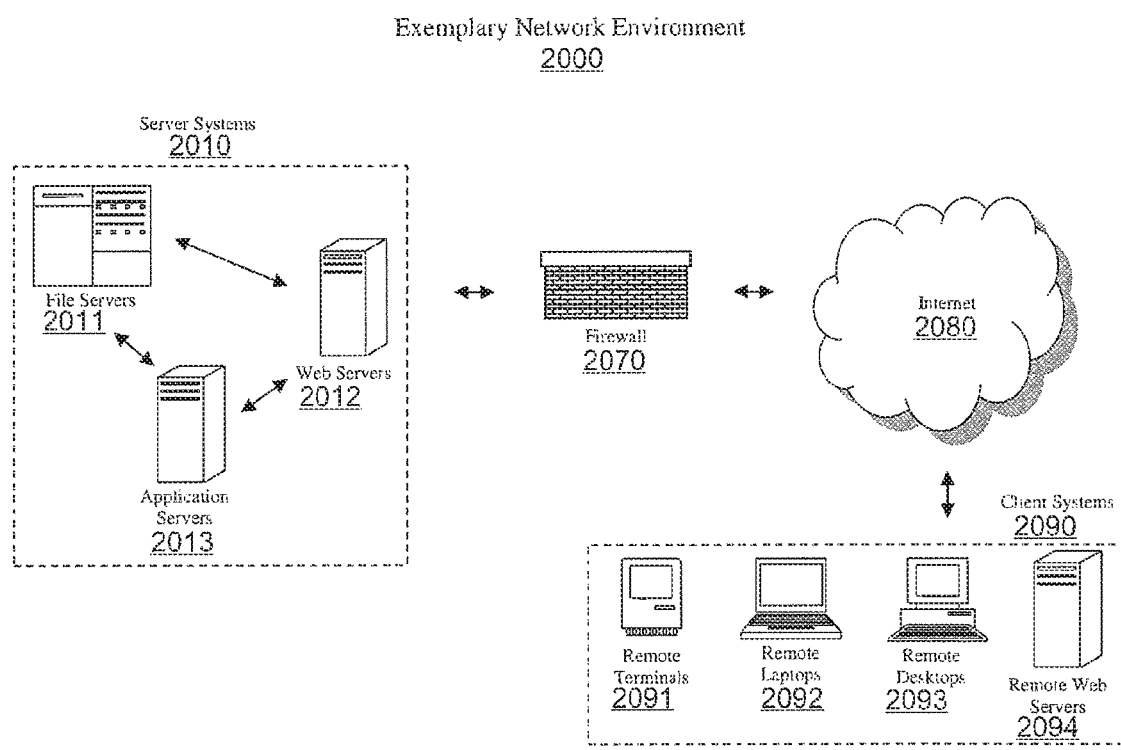
FIG. 18 is a sample computing network environment used in the system of FIG. 2.

In an exemplary embodiment as illustrated in FIG. 29, the invention includes computer implemented methods, transformative documents [FIG. 2 element 120], mathematical models and algorithms [FIG. 2 element 130], computer systems [FIG. 2, FIG. 17, FIG. 18], and computer readable storage media including instructions that when processed by a processor enable the processor to implement methods for an entity using the PODS system to realize a financial gain by purchasing debt at specific price and obtaining insurance reimbursement or obtaining a lower settlement amount with the creditor. In exemplary embodiments, such method includes the steps of:

the Seller accessing the software via the Internet or PODS network [FIG. 29 element 3110; FIG. 18 item 2080];

the Seller enters information into software via an application programming interface [FIG. 29 element 3120; FIG. 1A-1 through FIG. 1A-7 or FIG. 1B-1 through FIG. 1B-7];

the Seller uploads a scanned image of the medical bill and insurance statement [FIG. 27] (i.e., EOB) to the PODS computer system [FIG. 29 element 3130];

the PODS computer system stores the entered information in a physical binary structure that is stored on a computer readable storage medium as a PODS database [FIG. 29 element 3140];

the PODS computer system then scans the medical bill and EOB and populates the PODS database with this data [FIG. 29 element 3140];

the steps that are skipped with regard to FIGS. 13A-13C are the steps where the PODS entity makes an offer to accept the debt liability and the steps related thereto, namely, FIGS. 13A-13C element 1360 through element 1540; and the PODS computer system executes queries that contain mathematical models and algorithms [FIG. 2 element 130] over the data stored in the PODS database [FIG. 2 element 126; FIG. 29 element 3150] and results are produced as exemplified in FIGS. 9A-9C [FIG. 29 element 3160, FIG. 29 element 3165].

In the exemplary embodiment, execution of the mathematical models and algorithms includes executing computer code that processes historical data of past settlements [FIG. 2 element 126] in order to predict the provider's Settlement Price. This query returns a few different results (each based on a different mathematical model) as outlined in Section IV, entitled "Transformative Analysis of the Data" so that the PODS computer system may evaluate the predicted Settlement Price in different ways. Execution of the mathematical models and algorithms also includes executing computer code that processes the data inputted by the Seller to predict the provider's Settlement Price; a final value is then used/implemented. The, second methods, are strictly mathematical models and do not use the historic experience data [FIG. 2 element 126]. Based on the processing of the computer algorithms [FIG. 2 element 130], a mathematical model and results are determined [FIG. 9A, FIG. 9B, FIG. 9C].

In a step processing environment [FIG. 29 element 3160], the results that are determined [FIG. 9A, FIG. 9B, FIG. 9C] may then be presented to the PODS user and that user may select the calculation method they determine to be best to meet the Debtor's needs or, the PODS system will be implemented to automatically select the calculation that resulted in the greatest amount. This is done to help ensure the PODS user will obtain a reduction without a significant amount of resistance from the provider/creditor. FIG. 9C is a sample communication to the Debtor that includes the anticipated amount for which the creditor will settle the debt. The sample communication will also be accompanied by the information which provides instructions on how to interface with the payer and creditor as described in Appendix A and Appendix B [FIG. 29 element 3170].

The user of the PODS system will then i) seek reimbursement from a payer as outlined in Appendix B. Then ii) negotiate with the provider/creditor to accept a lower offer as outlined in Appendix A and/or find other ways to lower the outstanding debt. The user of the PODS computer system will then settle the debt [FIG. 29 element 3180] by the process described in Section VIII, entitled "Methods to Settle the Outstanding Balance Owed to the Provider/Creditor." In the automated implementation [FIG. 29 element 3165] the PODS entity determines a Settlement Price via a calculation method as described in the section entitled "Calculation Methods To Determine an Estimated Settlement Price" described in this disclosure. With these results the user/debtor settles the debt with the provider as outlined Section VIII entitled "Methods to Settle the Outstanding Balance Owed to the Provider/Creditor" in this disclosure.

The results of the Seller's/Debtors/patient's settlement with the provider/creditor will be sent to the PODS entity where the details/data will be entered into the PODS database [FIG. 2 element 126; FIG. 29 element 3190]. The process is then complete [FIG. 29 element 3195].

As a fee implementation for the PODS system, the PODS entity could sell advertising to pay for costs so it would not have to collect a fee from the Debtor/Seller.

XIX. How the PODS System is Implemented as a Collection Company

For the purpose of this disclosure, we will consider a collection company to be any entity seeking to collect a debt owed whether it be an in-house collection company, an outside collections company or a law firm acting as a collections company.

Figure 22:
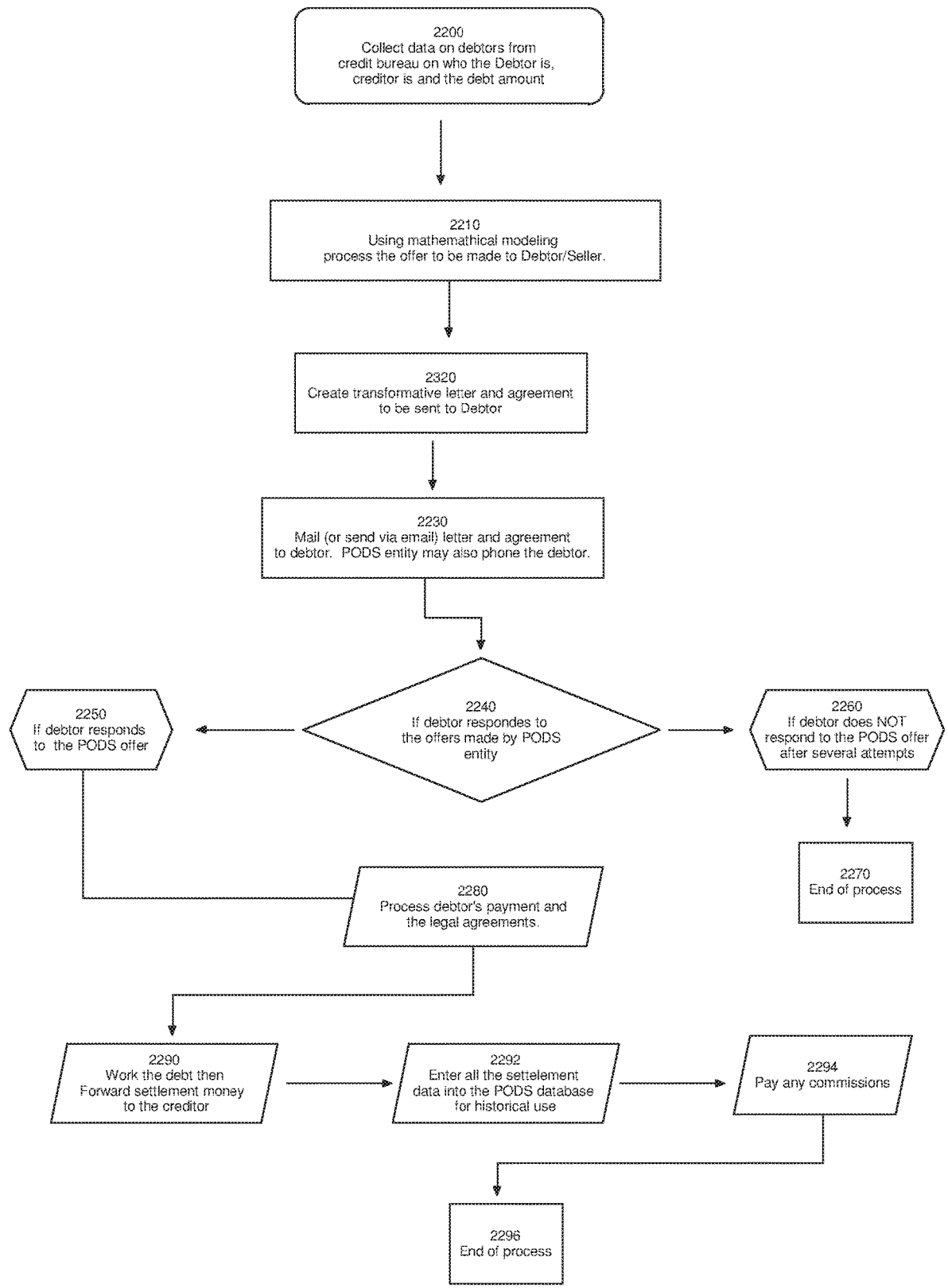
FIG. 22 is an exemplary flowchart of how the PODS system would be used by a creditor or collection company and in conjunction/tandem with a traditional collection company.

The process to act as a collections company consists of the following steps;

the step of contacting a credit bureau or creditor for a listing of debts then importing the collections data (debtor name, debtor contact information, creditor information, amount of debt, etc) into the PODS entity's database [FIG. 22 element 2200].

Note: in an alternative embodiment, the collection company's computer system may perform the algorithms and mathematical modeling [FIG. 2 element 130] using the PODS Entity's data [FIG. 2 element 126, FIG. 2 element 120, FIG. 2 element 142]. In such an embodiment, the PODS entity would supply the required databases and transformative materials (via database or via an Internet connection) to the payer's computer system so that the payer's computer system could perform all of the calculations, process the transformative documents, obtain payment, produce creditor letters, etc.

the step of determining a Settlement Price that the PODS entity is willing to accept from the Debtor as payment in full [FIG. 22 element 2210]. This may be accomplished by one of the following ways:

a) Using a historical database and calculations [FIG. 2 element 126, FIG. 2 element 130] like those described in Section IV, entitled "Transformative Analysis of the Data," calculate an estimated Settlement Price for the outstanding debt.

b) Using calculations like those in Section XV entitled "Estimated Selling Point [FIG. 2 element 130]," determine a proper Selling Price. Note, the Selling Price must be greater that the estimated Settlement Price, plus Cost to Work File, plus PODS profit, plus money to compensation for error margin.

Sample computer code:

if ($Selling_Price)<(($Settlement_Price)+($Cost_
   to_Work_File)+(SPODS_Profit)+(Smiley
   to_compensate_for_error_margin)) Exit; if then
   end process.

the step of processing the transformative letter(s) and agreements [FIG. 3-1 through FIG. 3-6, FIG. 4-1 through FIG. 4-6, or FIG. 5-1 through FIG. 5-6; and FIG. 21; and FIG. 22 element 2320] then mailing them via US Mail or email to the Seller/Debtor/patient/guarantor [FIG. 22 element 2230]. In addition to contacting the Seller/Debtor/patient/guarantor by mail or email, the PODS entity may also contact the Seller/ patient/guarantor by telephone and follow-up on the offer. FIG. 21 is an exemplary embodiment of a PODS collection offer letter.

The PODS entity must then wait to see if the Debtor/Seller responds to the offer [FIG. 22 element 2240]. If the Debtor/Seller does not respond [FIG. 22 element 2260], then that is the end of the process [FIG. 22 element 2270]. If the Seller/Debtor responds to the offer [FIG. 22 element 2250], then the PODS entity will process the Seller/Debtor's payment, scan the signed agreement(s) [FIG. 3-1 through FIG. 3-6, FIG. 4-1 through FIG. 4-6, or FIG. 5-1 through FIG. 5-6] in the PODS database and archive all the paper documents [FIG. 22 element 2280].

The step of working the debt [FIG. 22 element 2290] is outlined in Section VII, entitled "Working the Debt."

the step of sending the monies paid by the Seller/Debtor to the creditor is achieved via sending a check, wiring the monies owed, to the creditor [FIG. 22 element 2290].

the step of placing the settlement data into an electronic database that resides on computer readable medium, and that is stored in a physical binary structure and may be read by a computer [FIG. 22 element 2292].

the step of paying referral fees and commissions [FIG. 22 element 2294].

the process is now completed [FIG. 22 element 2296].

Implementing PODS in Tandem with a Traditional Collection Company

There are advantages to using the PODS collection system in tandem with a traditional collection company. In hunting terms, it is known as driving the hunted to the hunter. Essentially what occurs is the traditional collection company proceeds as normal with its collections efforts. Once the traditional collection company has made contact with the Debtor, the PODS collection efforts will being after a pre-determined time period (e.g., 1 week). The traditional collections company will then continue on with its standard processes and the PODS entity will continue on as described in FIG. 22. The reasoning is that the traditional collections company will scare the Debtor and when the "soft collections practices" of the PODS entity are offered, there will be a greater conversation rate (more collections made) than if the traditional collections company or the PODS Collections entity worked alone. In short, it is the same implementation as just described above [FIG. 22] but the PODS collection entity times its mailings and phone calls to begin shortly after that of the traditional collections company's efforts. The time period (i.e., delay) is determined by the PODS collections entity.

Paving Referral Fees and Commissions

Once the debt has been settled with the creditor commissions must be paid [FIG. 22 element 2294] to the referring entities. This is accomplished by sending payment with an accompanying accounting statement that the debt has been settled and the commission is $xx based on the profit made on the transaction and the terms of the agreement between the PODS entity and the referring entity.

Improvement Over Current Collections Practices a) Collection companies often offer discounts to debtors in exchange for paying off the amount due. Based on that, what is the advantage to buying the debt from the debtor vs a creditor, collection company or law firm accepting a lesser amount to settle the debt?

The current invention allows for the psychological perception of the debtor benefiting from paying off the debt at a lesser rate than dealing with the creditor or debt collection company.

b) Debtors often fear collection companies and go to great lengths to avoid contact with collection companies. Part of the reason is that collection companies make threatening calls, send threatening letters [FIG. 20], affect the debtor's credit rating [FIG. 20 item 2000], allude to lawsuits and wage garnishment, etc. The PODS entity has a different approach in that it simply offers to accept liability for the debt, at a reduced fee, and to that end, is not threatening to the debtor. And because there is no threat, the debtor is more likely to work. with the PODS entity than with a collection company.

c) Collection companies are regulated by the state and are subject to laws like the Fair Debt Collections Practices Act. Because the PODS entity is not acting as a collection company but as an entity that will accept liability for the debt in exchange for a reduced payment, it is not subject to the laws and regulations that collections companies are.

Alternative Embodiments as Related to Collection Companies

This disclosure is directed at medical debt. The fact is, the same software, system and methods may be used to track and anticipate the collections activities of any creditor. Examples include law firms, plumbers, credit card companies, contractors, casinos and all other entities that allow loans or credit.

XX. How the PODS System is Implemented by a Debt Settlement Company or Consumer Credit Counseling Service Debt settlement or debt resolution companies work by negotiating a lower payment on the debtor's outstanding debt. To accomplish this, the debtor makes monthly payments into an escrow account and once there is enough money in the escrow account, outstanding debts are settled at a reduced amount.

These debt companies have a problem, they are well suited to work with credit card debt, school loan debt, mortgages, etc. These companies are not well suited for medical debt and per a 2009 study in the American Journal of Medicine 62% of all bankruptcies included medical debt. This means that debt settlement and counseling companies need to address medical debt.

A way for a debt company to rapidly solve a debtor's outstanding medical debt is for the PODS entity to accept liability for the medical debt once the debtor has the funds in their escrow account to pay the PODS entity. This simple transaction allows the debtor to lower their outstanding debt quickly, the debt settlement/resolution company to supply their clients with a quick turnaround time, and the debt settlement company to realize an immediate commission/fee from its client based on having settled an outstanding debt.

Best Practices by a Debt Settlement/Debt Resolution Company:

When a debt settlement/resolution company takes a case with the intent to lower the amount owed the best practices, with regard to medical debt, include the following steps:

Step 1: Investigate if there is an insurance company that is liable for the debt. Examples include health insurance, workers compensation, homeowners insurance, auto coverage, etc. If there is insurance coverage, implement it and continue to step 2 below for any outstanding balances. If there is no coverage available, continue to step 2 below.

Step 2: Investigate if payment for the debt by Medicaid is an option. The company may use its standard practices to make this determination. If Medicaid is an option, implement it and continue to step 3 below for any balances due. If Medicaid is not an option, continue to step 3 below.

Step 3: Investigate if there are any charity care funds available from the provider or grants, from any source, that will cover the cost of the care. If there is charity care or a grant, implement it and continue to step 4 below with any balances. If there is no charity care or grants available, continue to step 4 below.

Step 4: Implement the PODS system as outlined in this disclosure.

An alternative embodiment is to simply allow the PODS entity assume the liability because the PODS entity will go through Steps 1 through Steps 4 on its own.

XXI. How the PODS System is Implemented by a Payer

The Medical Loss Ratio [FIG. 26C] was placed into effect under the federal Affordable Care Act and it limited the profitability of payers. Payers may implement the PODS system creating a new revenue stream that works with their current operating model(s) and the new revenue is not currently regulated under the Affordable Care Act (Medical Loss Ratio laws). FIG. 26A and FIG. 26B are exemplary financial projects for payers that implement the PODS system.

An additional advantage to payers implementing the PODS system is member satisfaction. By assisting their member in controlling the patient responsibility portion of the bills, payers are lowering attrition and building member loyalty.

Figure 14A:
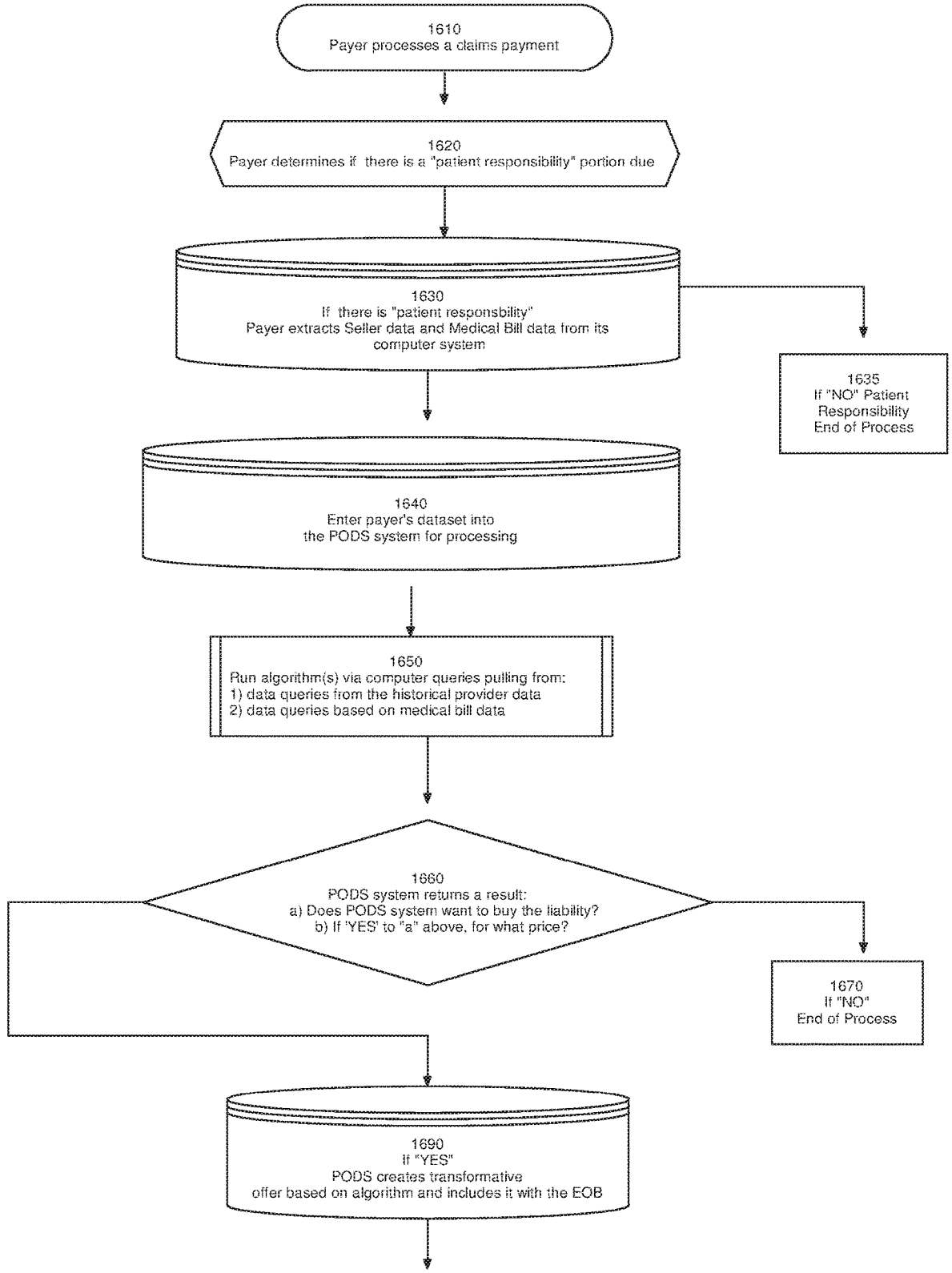

In an exemplary embodiment illustrated in FIGS. 14A-14C, a payer would utilize the PODS system in the following manner as this embodiment provides efficiencies, speed, increased knowledge as the payer already has the required information stored in its computer system. Of note is that the payer may implement the PODS system or the PODS system may be operated by an independent company utilizing the payer's EOB [FIG. 27] and reporting mechanism, and its claims data, as a sales channel:

Step 1: [FIG. 14A element 1610] A payer will process claims data, and determine the payer responsibility portion of the bill, the patient responsibility portion of the bill and any provider write-offs utilizing the payers normal processing methodologies.

Step 2: [FIG. 14A element 1620] The payer will run a mathematical algorithm over the claims data to determine if there is a "patient responsibility" portion due on the claim(s).

Step 3: [FIG. 14A. element 1630] If there is a "patient responsibility" due, the payer's computer system will run a computer query over the data to extract the Seller's contact information, all claims details, whether or not the provider is in-network or out-of-network and all other variables as described in Section IV entitled "Transformative Analysis of the Data," Table #1 [FIGS. 19A-19C]. If there is no patient responsibility, end of process [FIG. 14-A element 1635].

Step 4: [FIG. 14A element 1640] If there is patient responsibility, the payer's computer system will establish an electronic communication with the PODS system. The PODS computerized system inputs the information extracted from the payer's dataset into the PODS computerized system for processing to determine if there should be an offer to purchase the debt and if so, what type of agreement should be used [Appendix D, FIG. 3-1 through FIG. 3-6, FIG. 4-1 through FIG. 4-6, FIG. 5-1 through FIG. 5-6], and what the Selling Price is.

Note: In an alternative embodiment, the payer's computer system may perform the algorithms and mathematical modeling [FIG. 2 element 130] using the PODS entity's data [FIG. 2 element 126, FIG. 2 element 120, FIG. 2 element 142, Appendix D]. In such an embodiment, the PODS entity would supply the required databases and transformative materials (via database or via an Internet connection) to the payer's computer system so that the payer's computer system could perform all of the calculations, process the transformative documents, obtain payment, produce creditor letters, etc.

Step 5: [FIG. 14A element 1650] The PODS system executes computer queries that contain mathematical models and algorithms over its historic data for the specific provider(s) and amount(s) owed listed in the payers' dataset and results are produced [FIG. 2 element 126, FIG. 2 element 138, FIG. 2 element 120, FIG. 2 element 130]. Computer code is executed over the physical binary data structure that contains historical data of past settlements [FIG. 2 element 126 and FIGS. 19A-19C] in order to predict the provider's Settlement Price. This process is outlined in Section IV entitled "Transformative Analysis of the Data."

Step 6: [FIG. 14A element 1660] The PODS system will decide whether or not the PODS entity wants to purchase the debt bases on mathematical modeling and rules based decision making. If the PODS entity does not want to make an offer to purchase the debt, that is the end of the process [FIG. 14A element 1670].

Step 7: [FIG. 14A element 1690] If the PODS entity does want to make an offer to purchase the debt, it will create a transformative document [FIG. 2 element 120] based on the information extracted from the claims data and the results of the mathematical modeling and incorporate that into a new document that may be sent to the patient or member via the payer's electronic claims system or incorporated with the payer's paper EOB [FIG. 27] that is sent via US Mail. An example of such a document may be found in [FIG. 11 and FIG. 28]. The documents in FIGS. 11 and 28 are thus examples of communications to the Debtor/Seller that include the debt obligation of the Debtor/Seller and the offer to the Debtor/Seller to have the PODS entity fully assume the Debtor's/Seller's debt obligation.

An exemplary model of an electronic EOB offer via an electronic/web portal:

| OUT-OF-NETWORK CLAIM SEARCH RESULTS FOR JOHN DOE | | | | | |
|---|---|---|---|---|---|
| Claim No. | Date of Service | Provider | Insurance Paid | Patient Responsibility | PODS Offer* |
| 5435 | Jan. 3, 2014 | Dr Paul | $564 | $120 | $82 |
| 4565 | Feb. 4, 2014 | Dr Mary | $34,645 | $3,894 | $2,643 |
| 8678 | Feb. 15, 2014 | Dr Phil | $6,732 | $2,382 | $1,435 |
| 6443 | Mar. 2, 2014 | Dr Abby | $5,455 | $1,837 | $1,112 |

-continued

| OUT-OF-NETWORK CLAIM SEARCH RESULTS FOR JOHN DOE | | | | | |
|---|---|---|---|---|---|
| Claim No. | Date of Service | Provider | Insurance Paid | Patient Responsibility | PODS Offer* |

*all offers subject to questionnaire first
Click on the PODS offer link to be taken to the terms and agreement page Note: what is essentially occurring is that the PODS entity is incorporating an offer to accept liability for the debt when it sends its EOBs [FIG. 27] via mail or displays the claims information via the payer's web portal. This offer is made under "PODS Offer*" Note: The calculations performed in Section XV. Estimated Selling Point is what is used to determine the "PODS Offer*."

Step 8: The Seller may then choose to accept or decline the offer [FIG. 1413 element 1710]. If the Seller declines the offer [FIG. 14B element 1720] then that is the end of the process. If the Seller chooses to accept the offer [FIG. 14B element 1740], and is in the payer's web portal, the Seller will click a link to taking the Seller to area to accept the agreement [FIG. 3-1 through FIG. 3-6, FIG. 4-1 through FIG. 4-6 or FIG. 5-1 through FIG. 5-6] and make payment. If the offer was made via a paper EOB [FIG. 27], then the Seller will follow the instructions on the EOB on binding the agreement and making payment [FIG. 11 and FIG. 28].

Note: in an alternative embodiment the payer may incorporate the transformative agreement and a payment mechanism (as described in Step 9 below) in with the EOB that was mailed to the patient/member.

Step 9: The PODS entity will query the physical binary data structure for the legal language [FIG. 2 element 120] and then make a transformative document inputting the Seller's information, the medical bill information, and the purchase price that was determined by the mathematical models [FIG. 14B element 1750]. Examples of the transformative document may be found in FIG. 3-1 through FIG. 3-6, FIG. 4-1 through FIG. 4-6 or FIG. 5-1 through FIG. 5-6.

Step 10: [FIG. 14B element 1760] The transformative document will be displayed via a computer display to the Seller and the Seller must decide whether he/she wants to decline or accept the terms of the agreement [FIG. 3-1 through FIG. 3-6, FIG. 4-1 through FIG. 4-6 or FIG. 5-1 through FIG. 5-6] made by the PODS entity. If the Seller declines the offer (transformative documents containing legal language) [FIG. 1413 element 1770] then that is the end of the process [FIG. 14B element 1780]. If the Seller accepts the terms of the agreement [FIG. 3, FIG. 4 or FIG. 5] made by the PODS entity or the payer implementing the PODS system [FIG. 14B element 1790], then the PODS computer system will send an electronic copy of the agreement to the Seller. The PODS software will then display the electronic payment mechanism where the Seller may enter his/her credit card or electronic checking information [FIG. 1413 element 1800].

Step 11: After payment is made by the Seller, the PODS computer system will create a transformative letter [FIG. 1413 element 1810] that will be sent electronically to the creditor stating that the PODS entity has assumed the liability for the debt. An example of such a letter may be found in FIG. 6A, FIG. 7A or FIG. 8.

Figure 14C:
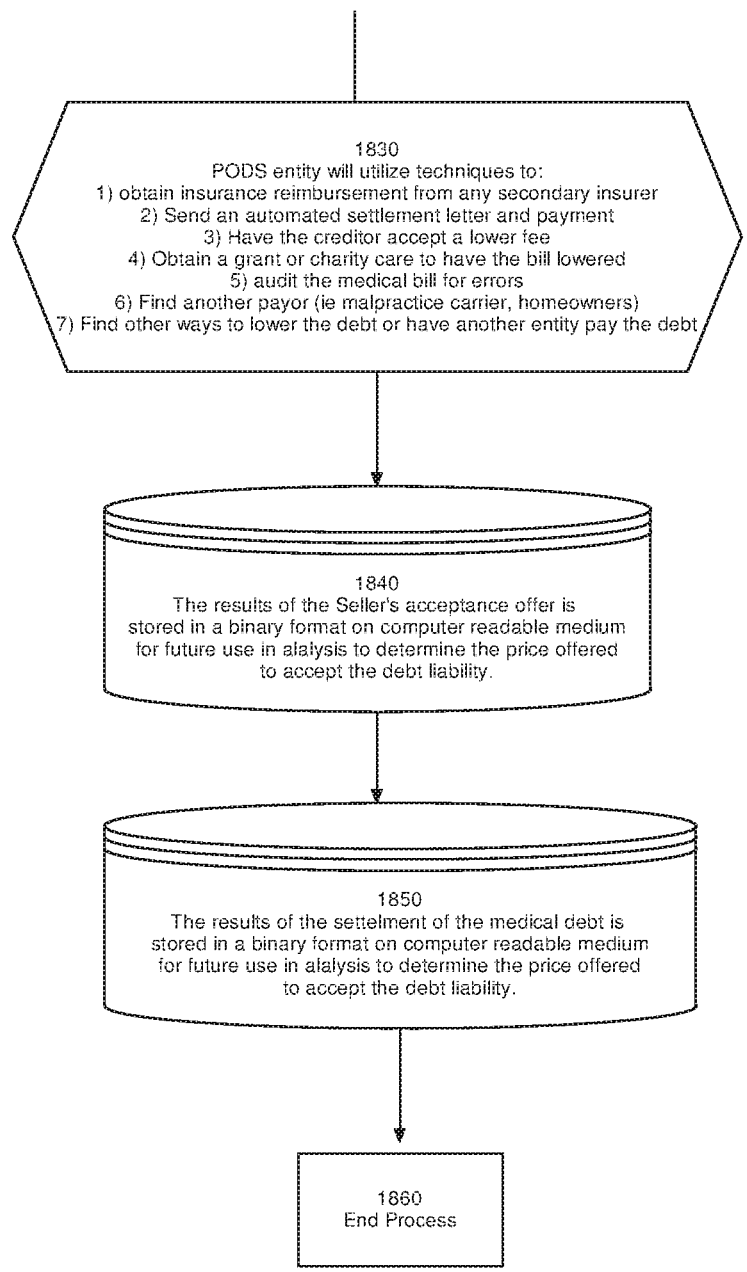

Step 12: [FIG. 14C element 1830] Next, in a fully automated embodiment [FIG. 14C element 1830], the PODS computer system would commence with the error checking calculations as described in Section IV. entitled "Transformative Analysis of the Data." Upon completion, the PODS computer system would implement the Calculation Methods To Determine an Estimated Settlement Price as described in Section IV. entitled "Transformative Analysis of the Data" to determine a final Settlement Price. After the processing of calculations the PODS computer would automate the settlement of the outstanding debt with the provider by a method as described in Section entitled "Methods to Settle the Outstanding Balance Owed to the Provider/Creditor."

In an embodiment that is automated but employs manual steps [FIG. 14C element 1830], the PODS entity will utilize its skill to seek reimbursement from any secondary payers, negotiate with the creditor to accept a lower offer, obtain a grant or charity care to help lower or pay the medical bill, audit the medical bill for errors, use Calculation Method #6 or Calculation Method #7 as described in Section VII (entitled "Working the Debt"), identify another payer (i.e., malpractice carrier, homeowners), and/or find other ways to lower the debt. In short, the payer will work the debt as describe in Section VII entitled "Working the Debt" of this disclosure and incorporate any additional leverage they have as a payer (i.e., incentives to join the payers network or other). Once the debt has been worked, it will be settled as described Section VIII entitled "Methods to Settle the Outstanding Balance Owed to the Provider/Creditor."

Step 13: [FIG. 14C element 1840] The results of the price the Debtor/Seller/patient finally paid to the PODS entity and demographic details are entered into the PODS historical database that is stored in a physical binary data structure on the computer readable medium [FIG. 2 element 126].

Step 14: [FIG. 14C element 1850] the results of the settlement of the medical debt are entered into the PODS historical database [FIG. 2 element 126, FIG. 19A through FIG. 19C] that is stored in a physical binary data structure on computer readable medium (i.e., computerized database). The process is then complete [FIG. 14C element 1860].

Note: This Section XXI entitled "How the PODS System is Implemented by a Payer" will addresses a payer's electronic explanation of benefits reporting process. In addition to payers, companies like Intuit's Health Expense Tracker (or HealthTrio Connect™ portal) integrate with payers to make EOBs available to members and to import the data from the EOB into the company's financial software products. The PODS system may be integrated with them in a similar manner. The PODS system may also be incorporated with employee care management tools like Castlight Health's Price Quality Comparison tool. Castlight Health's toll allows a prospective estimate of costs incurred for an episode of care and the PODS system would allow for a retrospective resolution for high patient responsibility (money owed by the patient/guarantor) portion of medical bills.

Advantage Over Companies Like MultiPlan and Global-Claim Service

When plan members go out-of-network they are subjected to balance billing by the provider. These providers may charge whatever fee they desire and that creates member dissatisfaction. The reason for the member dissatisfaction is that members expect their health plan to cover them when needed in exchange for paying their premiums. So when a member pay their plan premiums and is then expected to pay a provider's balance bill, which is often a significant amount of money, plan members become angry and member satisfaction deteriorates.

To protect members from balance billing and to increase member satisfaction, payers employ companies like MultiPlan and GlobalClaim Services to negotiate the out-of-network care fee prior to, or after the episode of care is provided [FIG. 24 and FIG. 25]. Because the cost of care is negotiated, the member ends up with a smaller patient responsibility portion of the bill then had it not be negotiated. There are problems with this implementation. First, payer must pay these negotiating companies for their services. Second, the provider does not have to accept the negotiated rate leave the patient vulnerable. Third, companies like MultiPlan often negotiate via fax so no leverage is used in the negotiation process. The process used is must akin to a simply offer and acceptance process with no additional tools or leverage being used by the negotiating companies.

The PODS process has many advantages. First, the PODS implementation audits the provider's charges for proper billing, proper standard of care, etc. as previously outlined in this disclosure. Auditing of the bill provides leverage not offered by companies that simply "negotiate bills". Second, the PODS process allows the payer to profit from the "patient responsibility portion" of the bill/claim. This then becomes a profit center when the PODS process is implemented. Third, the PODS implementation will generally be done by a well financed sophisticated entity that is able to fight providers whereas patients generally have fewer resources and are less sophisticated. Forth, Sellers will know that exact reduction they are getting on a medical bill before 'working the bill' is done. Claims companies and advocates cannot tell the Seller the discount after the work is done and that creates problems with taxes, and other things. Fifth, is the bill is novated, the Seller/patient/guarantor are insulated from negative consequences like credit ratings and lawsuits. Sixth, the PODS system automates the Selling Price, Payment Price and sends payment along with settlement terms.

How the PODS System Works with the Internal Revenue Services' 1099-C Requirement The Internal Revenue Service (IRS) requires that financial institutions file a cancelation of debt form (a 1099-C) on a person when all or part of a debt owed is written-off (See: http://www.irs.gov/pub/irs-pdf/i1099ac.pdf). The purpose of this is so that the IRS may tax the person on the amount of debt that is written-off as the IRS considers the forgiveness of a debt a taxable event.

The IRS mandates that financial institutions must file a 1099-C and some payers may be governed by the reporting requirements for a 1099-C. An advantage of the current invention is that it allows a forgiveness of debt to be passed onto the member without having to file a 1099-C with the IRS because the entity using the invention may not fall under the guidelines of a "financial institution." Further, because the negotiations between the entity using this invention and the provider are based on medical errors, fair market value and alike, the patient may not have to file a 1099-C because the write-off is based on an adjustment to the debt based on bringing the debt owed for services rendered in compliance with the fair market value of services and is therefore, not a true forgiveness of debt. Keep in mind, that providers may charge any fee they wish and that these fees are generally not the fair market value of the services rendered.

Taxpayers (i.e., the Debtor/patient) must always file a 1099-C for a forgiveness of debt. Whether or not their specific case qualifies as a forgiveness of debt or an adjustment to the fair market value is a determination the Debtor/patient must make with the advice of a tax professional.

Alternative Embodiments for Implementation by a Payer

A) The current disclosure describes a process that uses a healthcare payer's EOB statements [FIG. 27] as way to induce patients/members to transfer their outstanding debt obligations to the payer. This same process may also be accomplished with a payer's denial letters, appeals responses and/or other correspondence from the payer to the member/patient.

B) The PODS entity may be implemented by a viatical settlement company with great success. A viatical settlement is "An arrangement in which someone with a terminal disease sells his or her life insurance policy at a discount from its face value for ready cash. The buyer cashes in the full amount of the policy when the original owner dies. Also referred to as a Life Settlement." Viatical transactions generally occur during a person's end of life era. And because these event are at the end of life, large medical bills are generally incurred by the patient.

A viatical settlement company (or accident policy, limited benefits policies, emergency room policy, cancer policy, or similar policies AFLAC sells such policies as listed herein) may implement the PODS system in two ways. First, the viatical settlement company would estimate the amount of money it would pay for the life insurance policy. It would then add up all the medical bills that are outstanding. The viatical settlement company would then offer to pay the outstanding medical bills and give a lump sum cash payment to the patient. The point of this is "perceived value" to the patient.

EXAMPLE

Patient Profile:
1) Life insurance policy worth $1,000,000 upon death of the patient.
2) $200,000 in outstanding medical bills.

Viatical Company #1 Offer:
Cash payment to the patient for $500,000 for the insurance policy.

Viatical Company #2 Offer:
Cash payment to the patient for $400,000 for the insurance policy.
Assumption of all medical bills total $200,000

It is clear that the better value above is the offer from Viatical Company #2 for it offers a combined benefit of $600,000. But the reality is that Viatical Company #2 is only paying $500,000, the same as the offer from Viatical Company #1, but because Viatical Company #2 is using the PODS system, it benefits from a cost savings. By implementing the system in this manner, Viatical Company #2 has a competitive advantage over its competitors and offers the patient a better value for their money.

XXII. Social Policy

Politicians and healthcare industry leaders all agree on one point. That the Commonwealth of Massachusetts insurance mandate and the Affordable Care Act both allowed Americans access to care but failed on the point of controlling medical costs. While this invention cannot control medical malpractice litigation and the costs charged by providers, pharmaceutical companies and alike, it is the first step at controlling provider costs for end users (aka the patient/guarantor). By allowing a patient/debtor to transfer their debt liabilities to a sophisticated and sovereign entity that can resolve matters when faced with unscrupulous billing practices and mounting patient debt, patients/Debtors now have a valuable mechanism to control medical costs avoiding financial hardships and bankruptcy. All while ensuring the provider/creditor receives payment.

XXIII. Alternative Methods and Embodiments For the Full Disclosure

A) Some of the processes in this application may be altered. For example, FIG. 1A-1 through FIG. 1A-7 is used in situations where the patient/Debtor has already exhausted the payer (insurance) benefit, while FIG. 1B-1 through FIG. 1B-7 is used when a debtor wants to sell the debt prior to the insurance benefit being exhausted. The invention addresses novating the debt, acting as a guarantor, and acting as a step-in agent; however, other options include assignment are intended to be within the scope of the invention.

As another example, U.S. Pat. No. 5,446,653 describes a method of financial protection based on the data inputted in FIG. FIG. 1A-1 through FIG. 1A-7 or FIG. 1B-1 through FIG. 1B-7. (Note: the following implementations refer to FIG. 3-1 through FIG. 3-6, FIG. 4-1 through FIG. 4-6 and FIG. 5-1 through FIG. 5-6 depending on the implementation the PODS entity chose to use.)

1) If [FIG. 1A-7 item 124 or FIG. 1B-7 item 124], regarding lawsuits, is checked "yes" then the following text will be inserted at Section 6(B)(ii) in [FIG. 3-4 item 130, FIG. 4-5 item 130 or FIG. 5-5 item 130]. If it is checked "no" then the text will not be inserted in [FIG. 3-4 item 130, FIG. 4-5 item 130 or FIG. 5-5 item 130].
The text:
"(ii) If legal action by the provider is initiated for nonpayment of the bill(s) accepted by PODS entity (in Section 1) against Seller, PODS entity agrees to indemnity, defend and hold harmless ("assume the defense") Seller in the legal action. This clause is void if the legal action involves fraud, misrepresentation(s), a retracted payment by a payer, a breach of an agreement between the plaintiff and Seller, or other action that is not for the exclusive reason of payment of the medical bill."
2) If FIG. 1A-7 item 126 or FIG. 1B-& item 126, regarding credit repair, is checked "yes", then FIG. 10 will be sent to the Debtor via an electronic means (i.e., email, facsimile). If it is checked "no" then FIG. 10 will not be sent to the Debtor.

B) This disclosure cites entering data provided by the Seller and then the settlement data entered by the entity using the PODS system. In an alternative embodiment, data on collections procedures, lawsuits, credit ratings may be imported from data files provided by credit reporting agencies (for tracking of credit reporting issues), Nexus-Lexis or Westlaw (for tracking of lawsuits), collection companies (for tracking of outside collection activities) or even obtained from a provider's written policies.

C) This disclosure is directed at tracking the provider's collections activities. The activities of the collections companies are included in the tracking of the provider's activities. Further, Table 41 also includes tracking the collections activities of each collections company so this disclosure may be used to track the collections activities of specific collections companies.

D) An alternative embodiment for this invention is for Debtors to post their medical bills on a site like eBay but where all of the relevant data exists for a PODS entity to accurately determine an offer price. Namely, all of the facts on the bill including the provider name, amount, date of service, insurance payments, reasons for insurance denials (if any), if the patient was uninsured, the billing codes, the diagnostic codes, etc. exist. The PODS entity cold then use the same methods described herein to bid on the bill posted on the eBay-Like auction site.

The auction site profits the traditional ways that auction sites do by charging for posting the medical bill to be purchased by the auction site.

E) The PODS system may be used by estate planners to shorten the length of a probate period. This is because when a person dies, all of the person's liabilities are to be paid by the estate prior to the beneficiaries receiving the estates inheritance. By having the PODS entity assume all liability for the medical bills, the estate has settled its liabilities quickly and may move to distributing the assets of the estate to the heirs.

XXIV. Example Computing Environment

FIG. 17 and the following discussion are intended to provide a brief general description of a suitable computing environment in which an example embodiment of the invention may be implemented. It should be understood, however, that handheld, portable, and other computing devices of all kinds are contemplated for use in connection with the present invention. While a general purpose computer is described below, this is but one example. The present invention also may be operable on a thin client having network server interoperability and interaction. Thus, an example embodiment of the invention may be implemented in an environment of networked hosted services in which very little or minimal client resources are implicated, e.g., a networked environment in which the client device serves merely as a browser or interface to the World Wide Web.

Although not required, the invention can be implemented via an application programming interface (API), for use by a developer or tester, and/or included within the network browsing software which will be described in the general context of computer-executable instructions, such as program modules, being executed by one or more computers (e.g., client workstations, servers, or other devices). Generally, program modules include routines, programs, objects, components, data structures and the like that perform particular tasks or implement particular abstract data types. Typically, the functionality of the program modules may be combined or distributed as desired in various embodiments. Moreover, those skilled in the art will appreciate that the invention may be practiced with other computer system configurations. Other well-known computing systems, environments, and/or configurations that may be suitable for use with the invention include, but are not limited to, personal computers (PCs), server computers, hand-held or laptop devices, multi-processor systems, microprocessor-based systems, programmable consumer electronics, network PCs, minicomputers, mainframe computers, and the like. An embodiment of the invention may also be practiced in distributed computing environments where tasks are performed by remote processing devices that are linked through a communications network or other data transmission medium. In a distributed computing environment, program modules may be located in both local and remote computer storage media including memory storage devices.

FIG. 17 thus illustrates an example of a suitable computing system environment 1900 in which the invention may be implemented, although as made clear above, the computing system environment 1900 is only one example of a suitable computing environment and is not intended to suggest any limitation as to the scope of use or functionality of the invention. Neither should the computing environment 1900 be interpreted as having any dependency or requirement relating to any one or a combination of components illustrated in the exemplary operating environment 1900.

With reference to FIG. 17, an example system for implementing the invention includes a general purpose computing device in the form of a computer 110. Components of the computer 110 may include, but are not limited to, a processing unit 1920, a system memory 1930, and a system bus 121 that couples various system components including the system memory to the processing unit 1920. The system bus 121 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, Peripheral Component Interconnect (PCI) bus (also known as Mezzanine bus), and PCI-Express bus.

The computer 110 typically includes a variety of computer readable storage media. Computer readable storage media can be any available media that can be accessed by the computer 110 and includes volatile and nonvolatile, removable and non-removable media. By way of example, and not limitation, computer readable storage media includes volatile and nonvolatile, removable and non-removable storage media implemented in any method or technology for storage of information such as computer readable instructions, data structures, program modules or other data. Computer readable storage media includes, but is not limited to, random access memory (RAM), read-only memory (ROM), Electrically-Erasable Programmable Read-Only Memory (EEPROM), flash memory or other memory technology, compact disc read-only memory (CDROM), digital versatile disks (DVD) or other optical disk storage, magnetic cassettes, magnetic tape, magnetic disk storage or other magnetic storage devices, or any other medium which can be used to store the desired information and which can be accessed by the computer 110. Combinations of any of the above should also be included within the scope of computer readable storage media.

The system memory 1930 includes computer storage media in the form of volatile and/or nonvolatile memory such as ROM 1931 and RAM 1932. A basic input/output system 1933 (BIOS), containing the basic routines that help to transfer information between elements within computer 110, such as during start-up, is typically stored in ROM 1931. RAM 1932 typically contains data and/or program modules that are immediately accessible to and/or presently being operated on by the processing unit 1920. By way of example, and not limitation, FIG. 17 illustrates operating system 1934, application programs 1935, other program modules 1936, and program data 1937. RAM 1932 may contain other data and/or program modules.

The computer 110 may also include other removable/non-removable, volatile/nonvolatile computer readable storage media. By way of example only, FIG. 17 illustrates a hard disk drive 1941 that reads from or writes to non-removable, nonvolatile magnetic media, a magnetic disk drive 1951 that reads from or writes to a removable, nonvolatile magnetic disk 1952, and an optical disk drive 1955 that reads from or writes to a removable, nonvolatile optical disk 1956, such as a CD ROM or other optical media. Other removable/non-removable, volatile/nonvolatile computer storage media that can be used in the example operating environment include, but are not limited to, magnetic tape cassettes, flash memory cards, digital versatile disks, digital video tape, solid state RAM, solid state ROM, and the like. The hard disk drive 1941 is typically connected to the system bus 121 through a non-removable memory interface such as interface 1940, and magnetic disk drive 1951 and optical disk drive 1955 are typically connected to the system bus 121 by a removable memory interface, such as interface 1950.

The drives and their associated computer readable storage media discussed above and illustrated in FIG. 17 provide storage of computer readable instructions, data structures, program modules and other data for the computer 110. In FIG. 17, for example, the hard disk drive 1941 is illustrated as storing operating system 1934, application programs 1945, other program modules 1946, and program data 1947. Note that these components can either be the same as or different from operating system 1934, application programs 1935, other program modules 1936, and program data 1937. Operating system 1934, application programs 1935, other program modules 1936, and program data 1937 are given different numbers here to illustrate that, at a minimum, they are different copies. A user may enter commands and information into the computer 110 through input devices such as a keyboard 1962 and pointing device 1961, commonly referred to as a mouse, trackball or touch pad. Other input devices (not shown) may include a microphone, joystick, game pad, satellite dish, scanner, or the like. These and other input devices are often connected to the processing unit 1920 through a user input interface 1960 that is coupled to the system bus 121, but may be connected by other interface and bus structures, such as a parallel port, game port or a universal serial bus (USB).

A monitor 1991 or other type of display device is also connected to the system bus 121 via an interface, such as a video interface 1990. In addition to monitor 1991, computers may also include other peripheral output devices such as speakers and a printer (not shown), which may be connected through an output peripheral interface 1995.

The computer 110 may operate in a networked environment using logical connections to one or more remote computers, such as a remote computer 1980. The remote computer 1980 may be a personal computer, a server, a router, a network PC, a peer device or other common network node, and typically includes many or all of the elements described above relative to the computer 110, although only a memory storage device 1981 has been illustrated in FIG. 17. The logical connections depicted in FIG. 17 include a local area network (LAN) 1971 and a wide area network (WAN) 1973, but may also include other networks. Such networking environments are commonplace in offices, enterprise-wide computer networks, intranets and the Internet.

When used in a LAN networking environment, the computer 110 is connected to the LAN 1971 through a network interface or adapter 1970. When used in a WAN networking environment, the computer 110 typically includes means for establishing communications over the WAN 1973, such as the Internet. In a networked environment, program modules depicted relative to the computer 110, or portions thereof, may be stored in the remote memory storage device. By way of example, and not limitation, FIG. 17 illustrates remote application programs 1985 as residing on a memory device 1981. Remote application programs 1985 include, but are not limited to web server applications such as Microsoft® Internet Information Services (IIS)® and Apache HTTP Server which provides content which resides on the remote storage device 1981 or other accessible storage device to the World Wide Web. It will be appreciated that the network connections shown are exemplary and other means of establishing a communications link between the computers may be used.

One of ordinary skill in the art can appreciate that a computer 110 or other client devices can be deployed as part of a computer network. In this regard, the present invention pertains to any computer system having any number of memory or storage units, and any number of applications and processes occurring across any number of storage units or volumes. An embodiment of the present invention may apply to an environment with server computers and client computers deployed in a network environment, having remote or local storage. The present invention may also apply to a standalone computing device, having programming language functionality, interpretation and execution capabilities.

XXV. Example Network Environment

FIG. 18 illustrates an embodiment of a network environment in which an embodiment of the present invention can be implemented. The network environment 2000 contains a number of server systems 2010, which may include a number of file servers 2011, web servers 2012, and application servers 2013. These servers are in communication with a wider area network such as the Internet 2080 though typically some network security measures such as a firewall 2070. A number of client systems 2090 that are in communication with the server systems 2010. The client computer systems can be a variety of remote terminals 2091, remote laptops 2092, remote desktops 2093, and remote web servers 2094. Service requests are sent by client systems 2090 to the server systems 2010 via the network 2080. The server systems 2010 process the service requests, and return the results to the client systems via the network 2080.

FIG. 18 illustrates an exemplary network environment. Those of ordinary skill in the art will appreciate that the teachings of the present invention can be used with any number of network environments and network configurations.

These and other advantages of the present invention will be apparent to those skilled in the art from the foregoing specification. For example, the system and process of the invention provide a way to repair a negative credit remark on a person's credit history by way of novating the debt to another entity/person then submitting proof of liability for the debt. In an another embodiment, the PODS system may estimate the lowest amount to bid to purchase medical debt in an inverse auction, or a buy it now auction like that run by E-bay.com.

Accordingly, it will be recognized by those skilled in the art that changes or modifications may be made to the above-described embodiments without departing from the broad inventive concepts of the invention. It should therefore be understood that this invention is not limited to the particular embodiments described herein, but is rather intended to include all changes and modifications that are within the scope and spirit of the invention.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

I claim:

1. A computer-implemented method of resolving a Debtor's debt obligation to a creditor, wherein the creditor is a medical provider, an entity acting on behalf of the medical provider, or an owner of the Debtor's debt obligation, the method comprising:

receiving, by a processor, data relating to the Debtor's debt obligation from at least one of a medical bill, medical claim, or insurance statement of the Debtor, wherein the Debtor's debt obligation includes results from at least one of an insurance company's explanation of benefits, one or more medical bills, or one or more medical claims;

determining, by a rating algorithm implemented by the processor, an anticipated amount for which the creditor will settle the debt as a greater of a cost-to-charge ratio of the creditor or a percentage of a Medicare allowable amount for a medical debt owed by the Debtor, the rating algorithm using predictive analytics to determine the anticipated amount based on the data relating to the Debtor's debt obligation and historical settlement data of the creditor;

calculating, by the processor, a debt purchase amount to be offered to the Debtor to have a third-party entity fully assume the Debtor's debt obligation, the debt purchase amount being based on at least:

(i) the anticipated amount for which the creditor will settle the debt, and (ii) operating costs of the third-party entity and profit margin for the third-party entity;

automatically electronically generating and sending, by the processor, a communication to the Debtor via a communications network, the communication including an offer to the Debtor to have the third-party entity fully assume the Debtor's debt obligation for the debt purchase amount;

automatically electronically generating and sending, by the processor, a document via the communications network to the third-party entity, the document indicating that the Debtor has agreed to transfer the Debtor's debt obligation to the third-party entity pursuant to terms of the offer; and automatically electronically generating and sending, by the processor, a notification via the communications network to the creditor, the notification notifying the creditor that the third-party entity has assumed responsibility for the Debtor's debt obligation, wherein the third-party entity resolves the Debtor's debt obligation to the creditor.

2. The method of claim 1 wherein determining the anticipated amount comprises performing a total experience rating analysis comprising determining an average historical debt reduction given by the creditor and determining an expected cost for the third-party entity to obtain a settlement with the creditor.

3. The method of claim 1 wherein determining the anticipated amount comprises performing a specific experience rating analysis comprising determining an experience rating comprising an historical debt reduction for a given dollar amount of debt and an adjustment for a delta dollar amount paid by the third-party entity.

4. The method of claim 1 wherein determining the anticipated amount comprises performing a direct match debt amount rating analysis comprising determining an historical reduction for a given dollar amount by the creditor.

5. The method of claim 1 wherein determining the anticipated amount comprises performing a global analysis comprising assigning a weighted value to each variable of the medical debt.

6. The method of claim 1 wherein determining the anticipated amount comprises performing an experience rating analysis based on historical collection activities by the creditor.

7. The method of claim 1 wherein determining the anticipated amount comprises identifying an average of historic discounts provided by the creditor in settlements plus an expected cost for the third-party entity to obtain a settlement with the creditor.

8. The method of claim 1 wherein determining the anticipated amount comprises identifying an average of historic settlement amounts paid to the creditor by at least one of the third-party entity or other entities.

9. The method of claim 1 wherein determining the anticipated amount comprises estimating the anticipated amount for which the creditor will settle the debt based on a charity care status of the Debtor relative to the medical debt.

10. The method of claim 1 wherein electronically generating and sending the communication to the Debtor which includes the offer to the Debtor to have the third-party entity fully assume the Debtor's debt obligation comprises including the offer in the communication when the amount of the offer is greater than the anticipated amount for which the creditor will settle the debt.

11. The method of claim 1 wherein electronically generating and sending the document comprises:

electronically entering an indication of the Debtor's acceptance of the offer into the processor; and automatically generating, by the processor, the document, the document indicating that the Debtor's debt obligation is fully assumed by the third-party entity.

12. The method of claim 1 wherein the third-party entity is (i) a receiver entity of the Debtor's debt obligation which receives a novation of the Debtor's debt obligation, (ii) a guarantor of the Debtor's debt obligation, or (iii) a step-in entity of the Debtor's debt obligation.

13. The method of claim 1 wherein the data relating to the Debtor's debt obligation includes characteristics of the medical bills or billing statements including the Debtor's responsibility portion of the medical debt.

14. The method of claim 1 wherein determining the anticipated amount comprises applying characteristics of the creditor to the rating algorithm, the rating algorithm rating the creditor based on the creditor's historical willingness to settle debt.

15. The method of claim 1 wherein calculating the debt purchase amount comprises basing the offer on at least one of demographics and personal information about the Debtor.

16. The method of claim 1 wherein the Debtor's debt obligation includes a patient responsibility amount shown with or on an explanation of benefits communication or a medical claim denial letter.

17. The method of claim 1 wherein electronically generating and sending the communication to the Debtor which includes the offer to the Debtor to have the third-party entity fully assume the Debtor's debt obligation comprises including the communication to the Debtor with or on an explanation of benefits statement.

18. The method of claim 1 wherein the data relating to the Debtor's debt obligation comprises data from a credit bureau.

19. The method of claim 1 wherein the third-party entity is the Debtor's medical insurance company, payer, or health plan sponsor.

20. The method of claim 1 further comprising automatically checking for medical errors and billing errors in the data relating to the Debtor's debt obligation using the rating algorithm.

21. The method of claim 1 further comprising generating, by the processor, an explanation of benefits statement and sending the communication and the explanation of benefits statement to the Debtor including the offer to the Debtor to have the third-party entity fully assume the Debtor's debt obligation.

* * * * *